(12) United States Patent
La Riviere et al.

(10) Patent No.: US 11,647,975 B2
(45) Date of Patent: May 16, 2023

(54) RADIOTHERAPY APPARATUS AND METHODS FOR TREATMENT AND IMAGING USING HYBRID MEV-KEV, MULTI-ENERGY DATA ACQUISITION FOR ENHANCED IMAGING

(71) Applicants: Accuray, Inc., Sunnyvale, CA (US); The University of Chicago, Chicago, IL (US)

(72) Inventors: Patrick La Riviere, Chicago, IL (US); Daniel Gagnon, Twinsburg Heights, OH (US); Zhicong Yu, Highland Heights, OH (US); Julian Bertini, Chicago, IL (US); Phillip Vargas, Chicago, IL (US)

(73) Assignees: Accuray, Inc., Sunnyvale, CA (US); The University of Chicago, Chicago, IL (US)

( * ) Notice: Subject to any disclaimer, the term of this patent is extended or adjusted under 35 U.S.C. 154(b) by 55 days.

(21) Appl. No.: 17/339,319

(22) Filed: Jun. 4, 2021

(65) Prior Publication Data
US 2022/0395243 A1    Dec. 15, 2022

(51) Int. Cl.
*A61N 5/00* (2006.01)
*A61B 6/00* (2006.01)
(Continued)

(52) U.S. Cl.
CPC ............ *A61B 6/482* (2013.01); *A61B 6/0407* (2013.01); *A61B 6/4007* (2013.01);
(Continued)

(58) Field of Classification Search
CPC ...................... A61N 2005/1061; A61N 5/1081
See application file for complete search history.

(56) References Cited

U.S. PATENT DOCUMENTS

| 4,190,773 A | 2/1980 | Braden et al. |
| 5,615,279 A | 3/1997 | Yoshioka et al. |

(Continued)

FOREIGN PATENT DOCUMENTS

| DE | 102006007058 A1 | 7/2007 |
| DE | 102012200150 A1 | 7/2013 |

(Continued)

OTHER PUBLICATIONS

Anas, et al., High-quality 3D correction of ring and radiant artifacts in flat panel detector-based cone beam volume CT maging, Phys. Med. Biol., 2011, pp. 6495-6519, vol. 56.

(Continued)

*Primary Examiner* — Dani Fox
(74) *Attorney, Agent, or Firm* — Caifee, Halter & Griswold LLP

(57) ABSTRACT

A radio therapy system includes a first x-ray source. The first x-ray source is configured to produce first x-ray photons in a first energy range suitable for imaging and project the first x-ray photons onto an area designated for imaging. The system includes a second x-ray source configured to produce second x-ray photons in a second energy range higher energy than the first energy range, produce third x-ray photons in a third energy range higher energy than the first energy range, project the second x-ray photons onto the area designated for imaging, and project the third x-ray photons onto an area designated for treatment. The system includes an analytical portion configured to collect and combine data to create a composite output including at least one image, the combining based in part on a spectral analysis.

18 Claims, 17 Drawing Sheets

(51) Int. Cl.
    *A61N 5/10*     (2006.01)
    *A61B 6/04*     (2006.01)
    *G21K 5/04*     (2006.01)

(52) U.S. Cl.
    CPC .......... *A61B 6/4435* (2013.01); *A61B 6/5235* (2013.01); *A61N 5/1081* (2013.01); *G21K 5/04* (2013.01); *A61N 2005/1091* (2013.01)

(56) References Cited

U.S. PATENT DOCUMENTS

| | | |
|---|---|---|
| 6,233,478 B1 | 5/2001 | Liu |
| 6,307,909 B1 | 10/2001 | Flohr et al. |
| 7,050,528 B2 | 5/2006 | Chen |
| 7,108,421 B2 | 9/2006 | Gregerson et al. |
| 7,302,038 B2 | 11/2007 | Mackie et al. |
| 7,336,759 B2 | 2/2008 | Nukui |
| 7,660,380 B2 | 2/2010 | Boese et al. |
| 8,116,430 B1 | 2/2012 | Shapiro et al. |
| 8,467,497 B2 | 6/2013 | Lu et al. |
| 8,588,363 B2 | 11/2013 | Flohr |
| 9,400,332 B2 | 7/2016 | Star-Lack et al. |
| 11,337,668 B2 | 5/2022 | Yu et al. |
| 2003/0007601 A1 | 1/2003 | Jaffray et al. |
| 2003/0076927 A1 | 4/2003 | Nakashima et al. |
| 2004/0068169 A1 | 4/2004 | Mansfield et al. |
| 2004/0091079 A1 | 5/2004 | Zapalac |
| 2004/0102688 A1 | 5/2004 | Walker et al. |
| 2004/0202360 A1 | 10/2004 | Besson |
| 2005/0053188 A1 | 3/2005 | Gohno |
| 2005/0251029 A1 | 11/2005 | Khamene et al. |
| 2006/0109954 A1 | 5/2006 | Gohno |
| 2006/0262894 A1 | 11/2006 | Bernhardt et al. |
| 2007/0127621 A1 | 6/2007 | Grass et al. |
| 2007/0189444 A1 | 8/2007 | Van Steven-Daal et al. |
| 2008/0103834 A1 | 5/2008 | Reiner |
| 2008/0112532 A1 | 5/2008 | Schlomka |
| 2009/0080603 A1 | 3/2009 | Shukla et al. |
| 2009/0135994 A1 | 5/2009 | Yu et al. |
| 2009/0161826 A1 | 6/2009 | Gertner et al. |
| 2009/0225932 A1 | 9/2009 | Zhu et al. |
| 2009/0283682 A1 | 11/2009 | Star-Lack et al. |
| 2009/0304142 A1 | 12/2009 | Ruimi et al. |
| 2010/0046819 A1 | 2/2010 | Noo et al. |
| 2010/0142791 A1 | 6/2010 | Tsuji |
| 2010/0208964 A1 | 8/2010 | Wiegert et al. |
| 2011/0142312 A1 | 6/2011 | Toth et al. |
| 2011/0176717 A1 | 7/2011 | Siren et al. |
| 2011/0255656 A1 | 10/2011 | Star-Lack et al. |
| 2011/0255657 A1 | 10/2011 | Noordhoek |
| 2012/0014582 A1 | 1/2012 | Schaefer et al. |
| 2012/0121157 A1 | 5/2012 | Irie et al. |
| 2012/0207370 A1 | 8/2012 | Fahimian et al. |
| 2012/0263360 A1 | 10/2012 | Zhu et al. |
| 2012/0294504 A1 | 11/2012 | Kyriakou |
| 2013/0004052 A1 | 1/2013 | Chen et al. |
| 2013/0101082 A1 | 4/2013 | Jordan et al. |
| 2013/0294570 A1 | 11/2013 | Hansis |
| 2014/0018671 A1 | 1/2014 | Li et al. |
| 2014/0086383 A1 | 3/2014 | Huwer et al. |
| 2014/0169652 A1 | 6/2014 | Vic et al. |
| 2015/0297165 A1 | 10/2015 | Tanaka et al. |
| 2015/0305696 A1 | 10/2015 | Yamakawa et al. |
| 2016/0005194 A1 | 1/2016 | Schretter et al. |
| 2016/0016009 A1 | 1/2016 | Manzke et al. |
| 2016/0120486 A1 | 5/2016 | Goto et al. |
| 2016/0220844 A1 | 8/2016 | Paysan et al. |
| 2016/0262709 A1 | 9/2016 | Siewerdsen et al. |
| 2017/0000428 A1 | 1/2017 | Goto |
| 2017/0197098 A1 | 7/2017 | Hirasawa et al. |
| 2017/0205360 A1 | 7/2017 | Cinquin et al. |
| 2017/0278277 A1 | 9/2017 | Morf et al. |
| 2017/0332982 A1 | 11/2017 | Koehler et al. |
| 2018/0028143 A1 | 2/2018 | Wiggers et al. |
| 2018/0070894 A1 | 3/2018 | Osaki et al. |
| 2018/0192978 A1 | 7/2018 | Naylor et al. |
| 2018/0345042 A1 | 12/2018 | Voronenko et al. |
| 2019/0099149 A1 | 4/2019 | Li |
| 2020/0016432 A1* | 1/2020 | Maolinbay ........... A61N 5/1081 |
| 2020/0121267 A1 | 4/2020 | Deutschmann |
| 2020/0402644 A1 | 12/2020 | Zhou et al. |
| 2021/0165122 A1 | 6/2021 | Morton |

FOREIGN PATENT DOCUMENTS

| | | |
|---|---|---|
| EP | 1062914 A1 | 12/2000 |
| EP | 2383702 A1 | 11/2011 |
| JP | 09218939 A | 8/1997 |
| JP | 2004136021 A | 5/2004 |
| JP | 2008036275 A | 2/2008 |
| WO | 2005112753 A2 | 12/2005 |
| WO | 2006078386 A2 | 7/2006 |
| WO | 2010014288 A1 | 2/2010 |
| WO | 2010099621 A1 | 9/2010 |
| WO | 2015103184 A1 | 7/2015 |
| WO | 2018156968 A1 | 8/2018 |
| WO | 2018183748 A1 | 10/2018 |

OTHER PUBLICATIONS

Bootsma, et al., Spatial frequency spectrum of the x-ray scatter distribution in CBCT projections, Med. Phys., Nov. 2013, pp. 111901-1-111901-15, vol. 40, No. 11.
International Search Report and Written Opinion from PCT/US2021/039824 dated Mar. 4, 2022.
International Search Report and Written Opinion from PCT/US2021/042906 dated Mar. 21, 2022.
Rührnschopf, et al., A general framework and review of scatter correction methods in cone beam CT. Part 2: Scatter estimation approaches, Med. Phys. Sep. 2011, pp. 5186-5199, vol. 38, No. 9.
Yang, et al., Scattering estimation for cone-Beam CT Using Local Measurement Based on Compressed Sensing, IEEE transactions on Nuclear Science, Mar. 2018, pp. 941-949, vol. 65, No. 3.
Office Action from U.S. Appl. No. 16/694,161 dated Sep. 13, 2021, 18 pages.
Wang, Ge, X-Ray micro-CT with a displaced detector array, Medical Physics, Jul. 2002, pp. 1634-1636, vol. 29, No. 7.
Wertz, et al., Fast kilovoltage/megavoltage (kVMV) breathhold cone-beam CT for image-guided radiotherapy of lung cancer, Physics in Medicine and Biology, 2010, pp. 4203-4217, vol. 55.
Wu, et al., Metal artifact correction for x-ray computed tomography using kV and selective MV imaging, Medical Physics, Dec. 2014, pp. 121910-1-121910-15, vol. 41, No. 12.
Yu, et al., Radiation dose reduction in computed tomography: techniques and future perspective, Imaging Med., Oct. 2009, pp. 65-84, vol. 1.
Zamyatin, et al., Helical cone beam CT with an asymmetrical detector, Medical Physics, Oct. 2005, pp. 3117-3127, vol. 32, No. 10.
Zbijewski, et al., Efficient Monte Carlo Based Scatter Artifact Reduction in Cone-Beam Micro-CT, IEEE Transactions on Medical Imaging, Jul. 2006, pp. 817-827, vol. 25, No. 7.
Zhu, et al., Scatter Correction Method for X-ray CT Using Primary Modulation: Theory and Preliminary Results, IEEE Transactions on Medical Imaging, Dec. 2006, pp. 1573-1587, vol. 25, No. 12.
Zhu, et al. Noise suppression in scatter correction for cone-beam CT, American Association of Physicists in Medicine, 2009, pp. 741-752, vol. 36, No. 3.
Invitation to Pay Additional Fees from PCT/US2022/035500 dated Oct. 13, 2022, 14 pages.
Alvarez, et al., Energy-selective Reconstructions in X-ray Computerized Tomography, Physics in Medicine and Biology, 1976, pp. 733-744, vol. 21, No. 5.
Clackdoyle, et al., Data consistency conditions for truncated fanbeam and parallel projections, Med. Phys. Feb. 2015, pp. 831-845, vol. 42, No. 2.
Defrise, et al., A solution to the long-object problem in helical cone-beam tomography, Physics in Medicine and Biology, 2000, pp. 623-643, vol. 45.

(56) References Cited

OTHER PUBLICATIONS

Hsieh, et al., A novel reconstruction algorithm to extend the CT scan field-of-view, Med. Phys., Sep. 2004, pp. 2385-2391, vol. 31, No. 9.
International Search Report and Written Opinion from PCT/US2019/063071 dated Mar. 18, 2020.
International Search Report and Written Opinion from PCT/US2019/063073 dated Apr. 3, 2020.
International Search Report and Written Opinion from PCT/US2019/063074 dated Mar. 23, 2020.
International Search Report and Written Opinion from PCT/US2019/063076 dated Mar. 16, 2020.
International Search Report and Written Opinion from PCT/US2019/063077 dated Mar. 16, 2020.
International Search Report and Written Opinion from PCT/US2019/063078 dated Oct. 8, 2020.
International Search Report and Written Opinion from PCT/US2019/063080 dated Mar. 16, 2020.
International Search Report and Written Opinion from PCT/US2019/063083 dated Mar. 16, 2020.
International Search Report and Written Opinion from PCT/US2019/063085 dated Mar. 16, 2020.
International Search Report and Written Opinion from PCT/US2019/063086 dated Nov. 16, 2020.
International Search Report and Written Opinion from PCT/US2019/063087 dated Apr. 3, 2020.
Invitation to Pay Additional Fees from PCT/US2019/063086 dated Mar. 26, 2020.
Jeon, et al., Generation of hybrid sinograms for the recovery of kV-CT images with metal artifacts for helical tomotherapy.
Johnson, Thorsten, Dual-Energy CT: General Principles, American Journal of Roentgenology, Nov. 2012, pp. S3-S8, vol. 199.
Kang, et al., Accurate positioning for head and neck cancer patients using 2D and 3D image guidance, Journal of Applied Clinical Medical Physics, Mar. 2011, pp. 1-14, vol. 12, No. 1.
Katsevich, A., An improved exact filtered backprojection algorithm for spiral computed tomography, Advances in Applied Mathematics, 2004, pp. 691-697, vol. 32.
Kudo, et al., Exact and approximate algorithms for helical cone-beam CT, Physics in Medicine and Biology, 2004, pp. 1-26, vol. 49, No. 13.
Kunze, et al., Cone beam reconstruction with displaced flat panel detector, 10th International Meeting on Fully Three-Dimensional Image Reconstruction in Radiology and Nuclear Medicine, 2009, pp. 138-141.
Li, et al., Scatter kernel estimation with an edge-spread function method for cone-beam computed tomography imaging, Physics in Medicine and Biology, pp. 6729-6748, vol. 51.
Lindsay, et al., Investigation of combined kV/MV CBCT imaging with a high-DQE MV detector, Med. Phys., Feb. 2019, pp. 563-575, vol. 46, No. 2.
Liu, et al., X-Ray micro-CT with a displaced detector array: Application to helical cone-beam reconstruction, Medical Physics, Oct. 2003, pp. 2758-2761, vol. 30, No. 10.
Maslowski, et al., Acuros CTS: A fast, linear Boltzmann transport equation solver for computed tomography scatter—Part I: Core algorithms and validation, Med. Phys., 2018, pp. 1-15.
Myronakis, et al., Spectral imaging using clinical megavoltage beams and a novel multi-layer imager, Physics in Medicine and Biology, Nov. 2018, pp. 9127-9139, vol. 62, No. 23.
Ning, et al., X-ray scatter correction algorithm for cone beam CT imaging, Med. Phys., May 2004, pp. 1195-1202, vol. 31, No. 5.
Noo, et al., A new scheme for view-dependent data differentiation in fan-beam and cone-beam computed tomography, Physics in Medicine and Biology, 2007, pp. 5593-5414, vol. 52.
Notice of Allowance from U.S. Appl. No. 16/694,190 dated Jun. 23, 2021, 8 pages.
Office Action from U.S. Appl. No. 16/694,202 dated Apr. 9, 2021, 12 pages.
Office Action from U.S. Appl. No. 16/694,145 dated Mar. 17, 2021, 10 pages.
Office Action from U.S. Appl. No. 16/694,190 dated Mar. 26, 2021, 9 pages.
Office Action from U.S. Appl. No. 16/694,192 dated Jun. 10, 2021, 10 pages.
Office Action from U.S. Appl. No. 16/694,218 dated Apr. 15, 2021, 7 pages.
Office Action from U.S. Appl. No. 16/694,230 dated Apr. 1, 2021, 6 pages.
Pearson, et al., Dual-energy (MV/kV) CT with probabilistic attenuation mapping for IGRT applications, Physics of Medical Imaging, 2015, pp. 1-9, vol. 9412.
Ramamurthi, et al., Region of Interest Cone Beam Tomography With Prior CT Data, Conference Record of the 37th Asilomar Conference on Signals, Systems, & Computers, Nov. 2003, pp. 1924-1927, vol. 2.
Restriction Requirement from U.S. Appl. No. 16/694,210 dated Jun. 10, 2021, 6 pages.
Schäfer, et al., Cone-beam filtered back-projection for circular X-ray tomography with off-center detector, 10th International Meeting on Fully Three-Dimensional Image Reconstruction in Radiology and Nuclear Medicine, 2009, pp. 86-89.
Schäfer, et al., FBP and BPF reconstruction methods for circular X-ray tomography with off-center detector, Med. Phys., Jul. 2011, pp. S85-S94, vol. 38, No. 7.
Siewerdsen, et al., A simple, direct method for x-ray scatter estimation and correction in digital radiography and cone-beam CT, Med. Phys., Jan. 2006, pp. 187-197, vol. 33, No. 1.
Spearman, et al., Effect of Automated Attenuation-based Tube Voltage Selection on Radiation Dose at CT: An Observational Study on a Global Scale, Radiology, Apr. 2016, pp. 167-174, vol. 279, No. 1.
Sun, et al., Improved scatter correction using adaptive scatter kernel superposition, Physics in Medicine and Biology, Oct. 2010, pp. 6695-6720, vol. 55.
Tang, et al., A sinogram extrapolation method for CT field of view extension, Proceedings of the Fifth CT Meeting, 2018, pp. 206-209.
Wang, et al., A General Cone-Beam Reconstruction Algorithm, IEEE Transactions on Medical Imaging, Sep. 1993, pp. 486-496, vol. 12, No. 3.
Notice of Allowance from U.S. Appl. No. 17/383,740 dated Mar. 15, 2023, 11 pages.

* cited by examiner

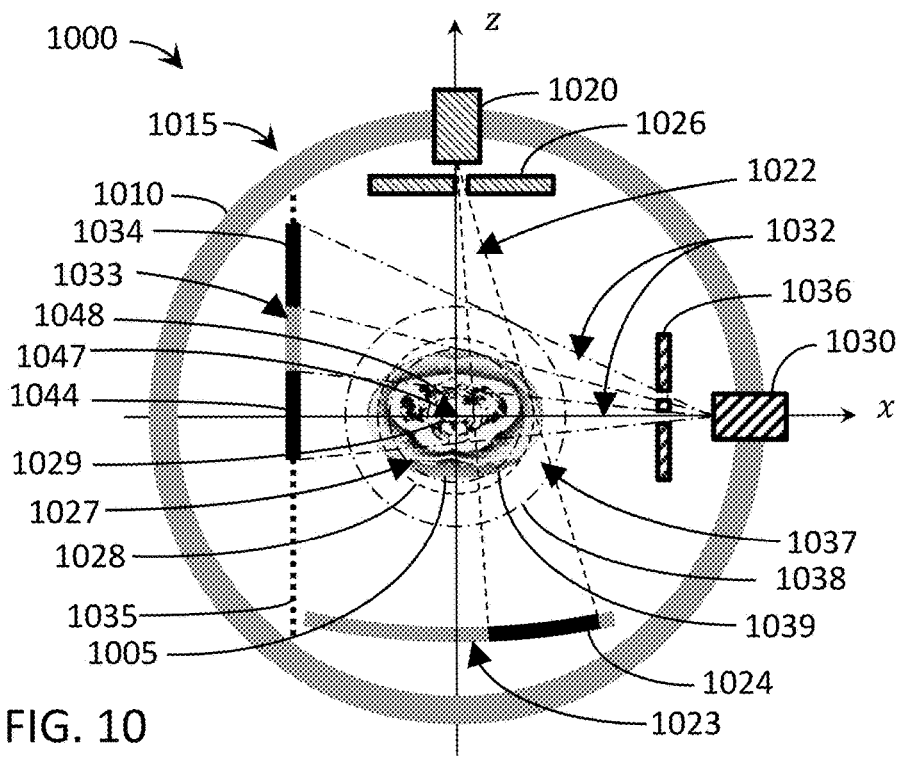
FIG. 10
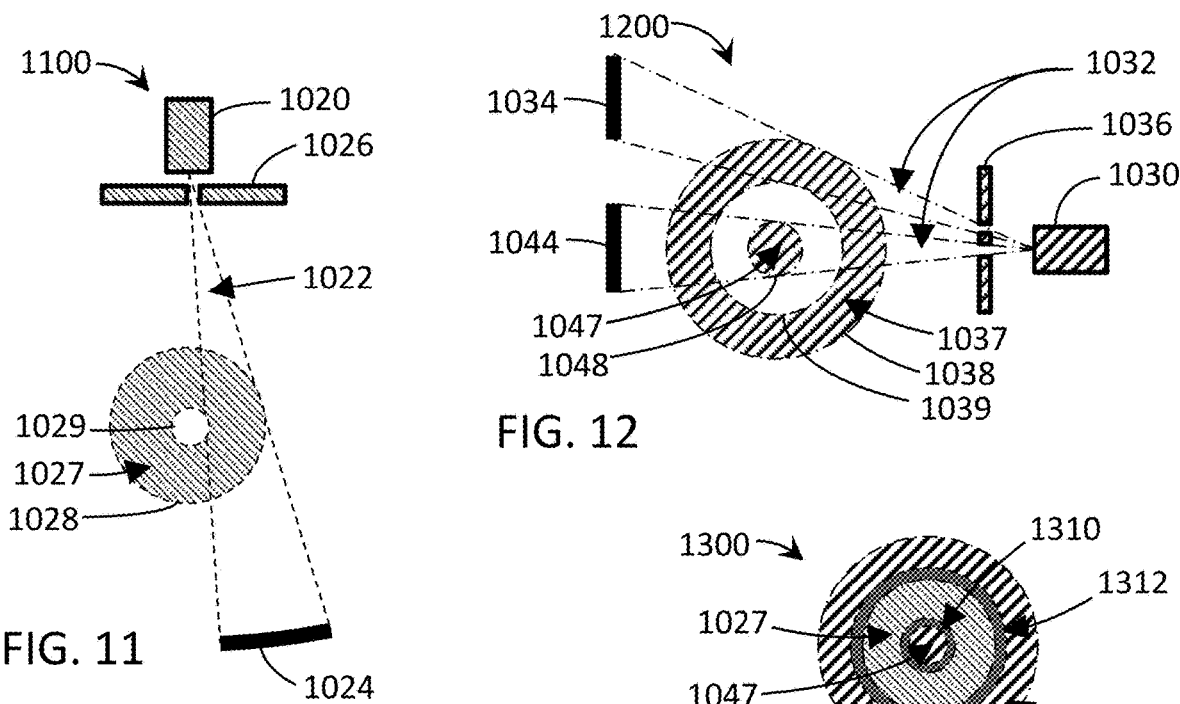
FIG. 11
FIG. 12
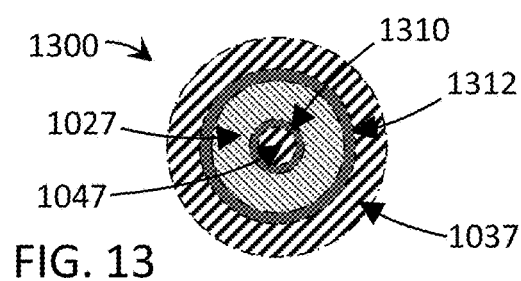
FIG. 13

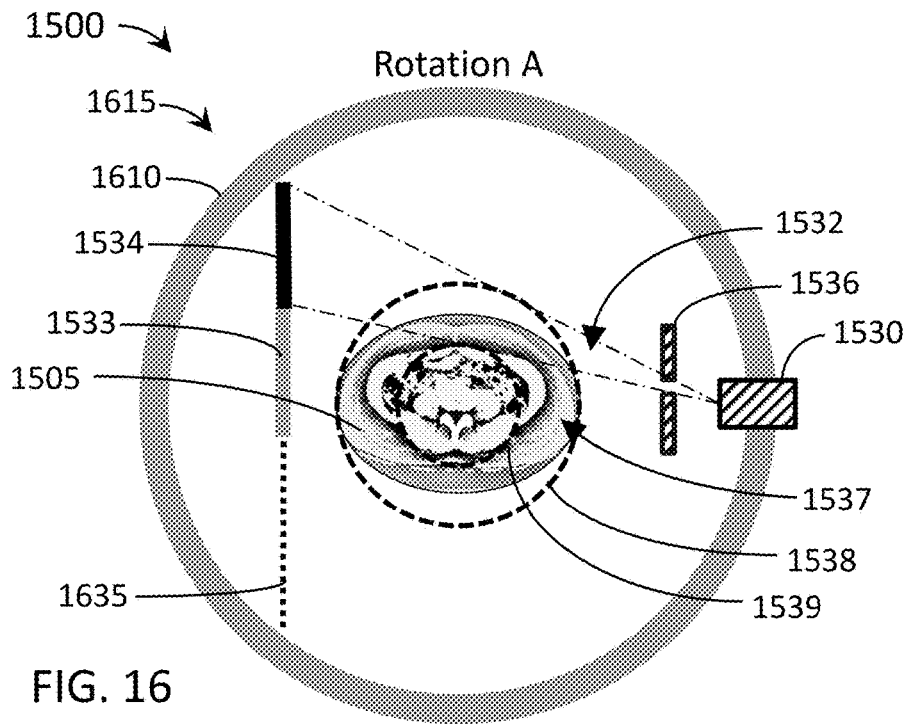
FIG. 16
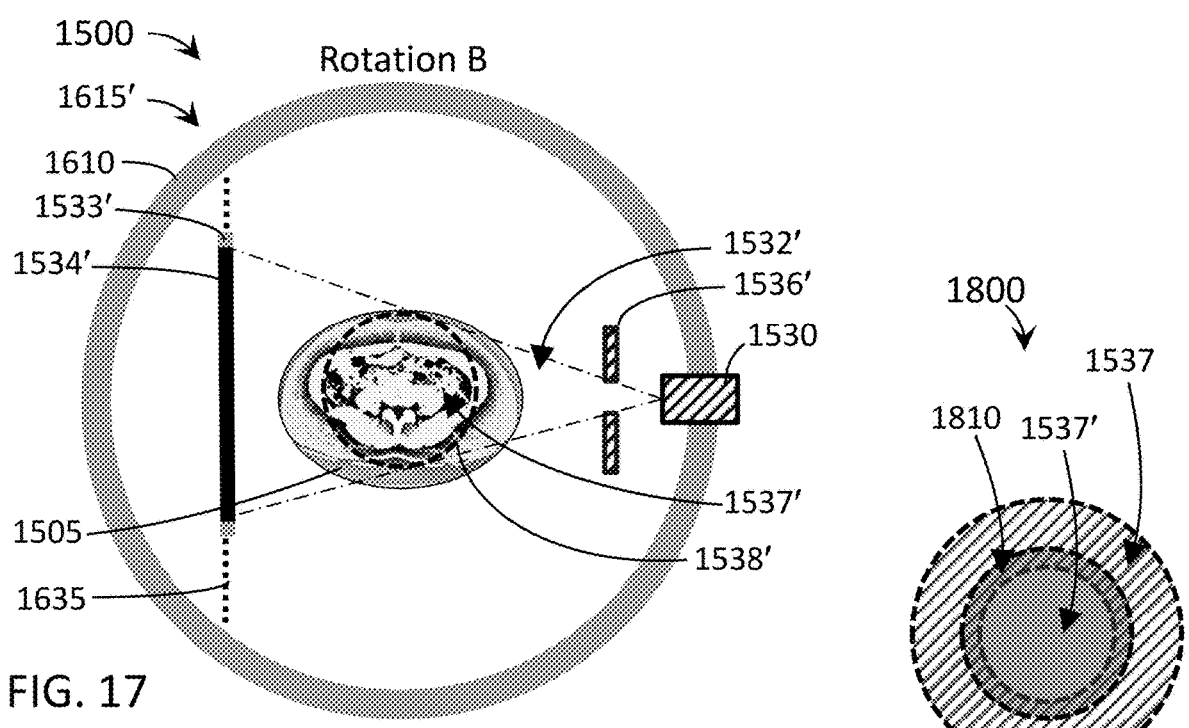
FIG. 17
FIG. 18

RADIOTHERAPY APPARATUS AND METHODS FOR TREATMENT AND IMAGING USING HYBRID MEV-KEV, MULTI-ENERGY DATA ACQUISITION FOR ENHANCED IMAGING

CROSS-REFERENCE TO RELATED APPLICATIONS

This application is related to U.S. patent application Ser. No. 16/694,148, to D. Gagnon et al., "APPARATUS AND METHODS FOR SCALABLE FIELD OF VIEW IMAGING USING A MULTI-SOURCE SYSTEM," filed on Nov. 25, 2019. This application also relates to eleven U.S. provisional patent applications, including Ser. No. 62/773,712, filed Nov. 30, 2018; Ser. No. 62/773,700, filed Nov. 30, 2018; Ser. No. 62/796,831, filed Jan. 25, 2019; Ser. No. 62/800,287, filed Feb. 1, 2019; Ser. No. 62/801,260, filed Feb. 5, 2019; Ser. No. 62/813,335, filed Mar. 4, 2019; Ser. No. 62/821,116, filed Mar. 20, 2019; Ser. No. 62/836,357, filed Apr. 19, 2019; Ser. No. 62/836,352, filed Apr. 19, 2019; Ser. No. 62/843,796, filed May 6, 2019; and Ser. No. 62/878,364, filed Jul. 25, 2019. This application is also related to ten non-provisional U.S. patent applications filed on Nov. 25, 2019, including Ser. No. 16/694,145, entitled "MULTIMODAL RADIATION APPARATUS AND METHODS," now U.S. Pat. No. 11,154,269; Ser. No. 16/694,161, entitled "INTEGRATED HELICAL FAN-BEAM COMPUTED TOMOGRAPHY IN IMAGE-GUIDED RADIATION TREATMENT DEVICE," now U.S. Pat. No. 11,375,970; Ser. No. 16/694,166, entitled "COMPUTED TOMOGRAPHY SYSTEM AND METHOD FOR IMAGE IMPROVEMENT USING PRIOR IMAGE," now U.S. Pat. No. 11,337,668; Ser. No. 16/694,177, entitled "OPTIMIZED SCANNING METHODS AND TOMOGRAPHY SYSTEM USING REGION OF INTEREST DATA," now U.S. Pat. No. 11,364,007; Ser. No. 16/694,190, entitled "HELICAL CONE-BEAM COMPUTED TOMOGRAPHY IMAGING WITH AN OFF-CENTERED DETECTOR," now U.S. Pat. No. 11,179,132; Ser. No. 16/694,192, entitled "MULTI-PASS COMPUTED TOMOGRAPHY SCANS FOR IMPROVED WORKFLOW AND PERFORMANCE," now U.S. Pat. No. 11,357,467; Ser. No. 16/694,202, entitled "METHOD AND APPARATUS FOR SCATTER ESTIMATION IN CONE-BEAM COMPUTED TOMOGRAPHY," now U.S. Pat. No. 11,160,526; Ser. No. 16/694,210, entitled "ASYMMETRIC SCATTER FITTING FOR OPTIMAL PANEL READOUT IN CONE-BEAM COMPUTED TOMOGRAPHY," now U.S. Pat. No. 11,324,471; Ser. No. 16/694,218, entitled "METHOD AND APPARATUS FOR IMPROVING SCATTER ESTIMATION AND CORRECTION IN IMAGING," now U.S. Pat. No. 11,224,396; and Ser. No. 16/694,230, entitled "METHOD AND APPARATUS FOR IMAGE RECONSTRUCTION AND CORRECTION USING INTER-FRACTIONAL INFORMATION," now U.S. Pat. No. 11,191,511. The contents of all above-identified patent application(s) and patent(s) are fully incorporated herein by reference.

FIELD OF THE INVENTION

Aspects of the disclosed technology relate to utilizing multimodal radiation for imaging, and, more particularly, utilizing lower-energy radiation (e.g., kilo-electron volt x-rays (keV)) and higher-energy radiation (e.g., mega-electron volt x-rays (MeV)) in combination for improved imaging and image interpretation, including for scalable fields-of-view during computed tomography (CT) scans.

BACKGROUND

External beam radiation therapy provides a non-invasive alternative to riskier, more invasive surgery. It can treat pathological anatomies (e.g., tumors, lesions, vascular malformations, nerve disorders, etc.) with x-rays generated by a therapeutic radiation source, such as a linear accelerator (LINAC). Typically, a source directs x-ray beams at a tumor site from multiple angles. Careful control of the source's orientation can insure that each x-ray beam passes through the same tumor site, but through a different area of neighboring healthy tissue. This keeps the cumulative radiation dose at the tumor high while keeping the dose in healthy tissue relatively low.

"Radiosurgery" refers to applying radiation to a target region at doses sufficient to necrotize a pathology more quickly than radiotherapy. It applies higher radiation doses per fraction (e.g., 500-2000 centigray) and hypo-fractionation (e.g., one to five fractions or treatment days). In contrast, radiotherapy may use 100-200 centigray and hyper-fractionation (e.g., 30 to 45 fractions). X-ray sources for radiotherapy and radiosurgery tend to be in MeV range. This is higher energy than x-ray sources for imaging, which tend to be in the keV range. The terms "radiation treatment" and "radiation therapy" are used interchangeably herein to mean radiosurgery and/or radiotherapy unless otherwise noted, for convenience in contrasting these two MeV techniques with imaging techniques using keV x-rays. Note that, herein, "MV" and "MeV" x-rays and sources are referred to interchangeably, as are "kV" and "keV" x-rays and sources per convention. When x-ray and source energies are specifically referred to, "MeV" and "keV" are used.

Image-guided radiation therapy (IGRT) systems combine keV and MeV sources for imaging and treatment. IGRT systems are typically classified by how they mount and move the therapeutic x-ray sources. In gantry IGRTs, a gantry rotates the therapeutic radiation source around an axis passing through an "isocenter," or point of intersection of x-ray beams. The results in x-ray beam intersection in a 3D volume in the shape of a sphere or ellipsoid. Different types of gantries mount and move x-ray sources differently. C-arm gantries mount the therapeutic radiation source in a cantilever and rotate it about an axis passing through the isocenter. Ring gantries mount the therapeutic source to a toroidal or ring shaped element. The patient's body extends through the hole in the toroid or ring. The toroid or ring rotates about an axis passing through the isocenter. In robotic arm-based systems, mounting the therapeutic radiation source on a robotic arm gives its motion more degrees of freedom. The robotic arm extends over and around the patient. It can provide at least five degrees of freedom to deliver therapeutic radiation from multiple out-of-plane directions. In contrast, ring or C-arm systems deliver therapeutic radiation with a set angle defined by the rotational trajectory of the radiation source.

X-ray imaging systems can be incorporated into radiation therapy systems to guide radiation delivery. They can also track in-treatment target motion. MeV imaging systems can place a detector opposite the therapeutic source to image the patient for setup and in-treatment images. Other approaches use distinct, independent image radiation source(s) and/or detector(s) for patient set-up and in-treatment images. Comparing in-treatment images to prior or pre-treatment image information allows tracking of the target during treatment.

Pre-treatment image information may comprise, for example, CT data, cone-beam CT (CBCT) data, magnetic resonance imaging (MRI) data, positron emission tomography (PET) data or 3D rotational angiography (3DRA) data, and any information obtained from these imaging modalities (for example and without limitation, digitally reconstructed radiographs (DRRs)).

As discussed above, typically, keV x-ray sources are used for imaging. keV sources tend to provide good contrast with most kinds of soft tissue. However, keV systems do not perform as well when the imaging zone includes more dense tissue (e.g., thick bones, calcified arteries, etc.). When tissue of interest lies within the same irradiated area as these dense materials, keV images can suffer defects caused by the interactions of the keV x-rays and the dense material. Streak artifacts may obscure or darken areas of interest. Metal (e.g., in dental fillings, implants, or stents) along an x-ray path can cause photon starvation, obscuring regions of interest. Scattering errors and other issues may cause additional problems. Another significant problem is "beam hardening," where certain portions of the body "see" a different x-ray photon spectrum due to selective absorption in other portions of the body.

MeV x-ray sources primarily used for treatment can also generate images. However, the contrast-to-noise ratio (CNR) in MeV images can be low. There are indeed some tissues whose native contrast is better in the keV range and others where it is better in the MeV. But at matched dose, which is a key factor in patient imaging, there will be fewer MeV x-rays. Also, MeV x-rays are more difficult to detect, leading to higher noise in those measurements. This makes MeV CNR generally worse for all tissues.

Crude MeV x-rays images are often used to determine the location of the MeV treatment beam with respect to the patient. Yet there is untapped potential for more ambitious MeV imaging applications. In particular, combining keV and MeV x-ray imaging in a single therapeutic device can use the complimentary advantages of both energy ranges. For example, contrast from MeV x-rays could fill in gaps in keV images where denser tissue degrades keV imaging contrast. Therefore, refined and improved techniques for combining information from both types of images are disclosed below.

BRIEF SUMMARY

According to aspects of the present disclosure, a radio therapy system may comprise a first x-ray source. The first x-ray source may be configured to produce first x-ray photons in a first energy range suitable for imaging and project the first x-ray photons onto an area designated for imaging. The system may comprise a second x-ray source configured to produce second x-ray photons in a second energy range higher energy than the first energy range, produce third x-ray photons in a third energy range higher energy than the first energy range, project the second x-ray photons onto the area designated for imaging, and project the third x-ray photons onto an area designated for treatment. The system may comprise an analytical portion configured to collect first data relating to the transmission of the first x-ray photons through the area designated for imaging, collect second data relating to the transmission of the second x-ray photons through the area designated for imaging, and combine the first and second data to create a composite output including at least one image, the combining based in part on a spectral analysis of at least one of the first and second data.

The first energy range may be between 40 keV and 150 keV. The second energy range may be between 400 keV and 6 MeV. The combining the first and second data may comprise at least one of sorting the second data into at least two categories based on a detected energy of the second x-ray photons, and identifying a material in the at least one image based on the at least two categories. The area designated for imaging and the area designated for treatment may overlap. The identifying a material may be based on analyzing a lower energy category of the at least two categories. The lower energy category may overlap with an energy range relating to the photoelectric effect.

The combining the first and second data may comprise at least one of sorting the first data and second into at least two categories based on a detected energy of the first x-ray photons and a detected energy of the second x-ray photons, determining a relative proportion of Compton effect and photoelectric effect range photons represented by the at least two categories, and identifying a material in the at least one image based on the relative proportion of Compton effect and photoelectric effect range photons. Collecting second data relating to the transmission of the first x-ray photons may comprises determining an energy for each of the detected second x-ray photons, and building a first histogram representing the number of detected photons within segments of the second energy range. Collecting first data relating to the transmission of the first x-ray photons may comprise determining an energy for each of the detected first x-ray photons, and building a second histogram representing the number of detected photons within segments of the first energy range. The first and second x-ray sources may be positioned such that they project the first x-ray photons at an angle that differs from the projected second x-ray photons by approximately 90 degrees. The first and second x-ray sources may be coplanar. The first and second x-ray sources may be apart in the axial direction.

Aspects of the present disclosure may further comprise a multimodal imaging apparatus. The apparatus may comprise a rotatable gantry system positioned at least partially around a patient support, a first radiation source coupled to the rotatable gantry system, the first radiation source configured for imaging radiation, a first beamformer configured to adjust a shape of a first radiation beam emitted by the first radiation source, a second radiation source coupled to the rotatable gantry system, the second radiation source configured for imaging radiation and therapeutic radiation, wherein the second radiation source may comprise an energy level more than the first radiation source, a second beamformer configured to adjust a shape of a second radiation beam emitted by the second radiation source, and at least one radiation detector coupled to the rotatable gantry system and positioned to receive radiation from at least one of the first radiation source or the second radiation source.

The apparatus may be configured to acquire first measured projection data associated with a first region of a patient from the first radiation source and second measured projection data associated with a second region of the patient from the second radiation source during a scan, and combine the first and second measured projection data to create a composite output including at least one image, the combining based in part on a spectral analysis of at least one of the first and second measured projection data. The first source of radiation may comprise a kilo-electron volt peak photon energy (keV) up to 150 keV and the second source of radiation may comprise a mega-electron volt peak photon energy (MeV) of 1 MeV or greater. The combining the first and second measured projection data may comprise at least one of sorting the second measured projection data into at least two categories based on a detected energy of x-ray photons contributing to the second measured projection data, and identifying a material in the at least one image based on the at least two categories. The identifying a material may be based in part on at least one of determining a relative proportion of Compton effect and photoelectric effect range photons represented by the at least two categories, Aspect of the present disclosure may include a method of acquiring projection data from a multimodal imaging apparatus. The method may comprise receiving first measured projection data associated with a first region of a patient from a first radiation source, the first radiation source configured for imaging radiation, receiving second measured projection data associated with a second region of the patient from a second radiation source, the second radiation source configured for imaging radiation and therapeutic radiation, wherein the second radiation source may comprise an energy level more than the first radiation source, and combining first and second measured projection data to create a composite output including at least one image, the combining based in part on a spectral analysis of at least one of the first and second measured projection data.

Features that are described and/or illustrated with respect to one embodiment may be used in the same way or in a similar way in one or more other embodiments and/or in combination with or instead of the features of the other embodiments.

The descriptions of the invention do not limit the words used in the claims in any way or the scope of the claims or invention. The words used in the claims have all of their full ordinary meanings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of this invention. It will be appreciated that illustrated element boundaries (e.g., boxes, groups of boxes, or other shapes) in the figures represent one embodiment of boundaries. In some embodiments, one element may be designed as multiple elements or that multiple elements may be designed as one element. In some embodiments, an element shown as an internal component of another element may be implemented as an external component and vice versa. Furthermore, elements may not be drawn to scale.

FIG. 10 shows an illustration of an exemplary multimodal scan configuration projecting through an exemplary patient in a transaxial plane.

FIG. 11 shows an illustration of the MeV subsystem of the exemplary multimodal scan configuration shown in FIG. 10.

FIG. 12 shows an illustration of the keV subsystem of the exemplary multimodal scan configuration shown in FIG. 10.

FIG. 13 shows an illustration of the various FOV regions created by the multimodal scan configuration shown in FIG. 10 in a superimposed view.

FIG. 16 shows an illustration of the exemplary keV radiation source during the multimodal scan configuration shown in FIG. 15 projecting through the exemplary patient in a transaxial plane during an exemplary rotation.

FIG. 17 shows an illustration of the exemplary keV radiation source during the multimodal scan configuration shown in FIG. 15 projecting through the exemplary patient in the transaxial plane during another exemplary rotation.

FIG. 18 shows an illustration of the various FOV regions created by the keV radiation source shown in FIGS. 16 and 17 in a superimposed view.

DETAILED DESCRIPTION

Figure 1:
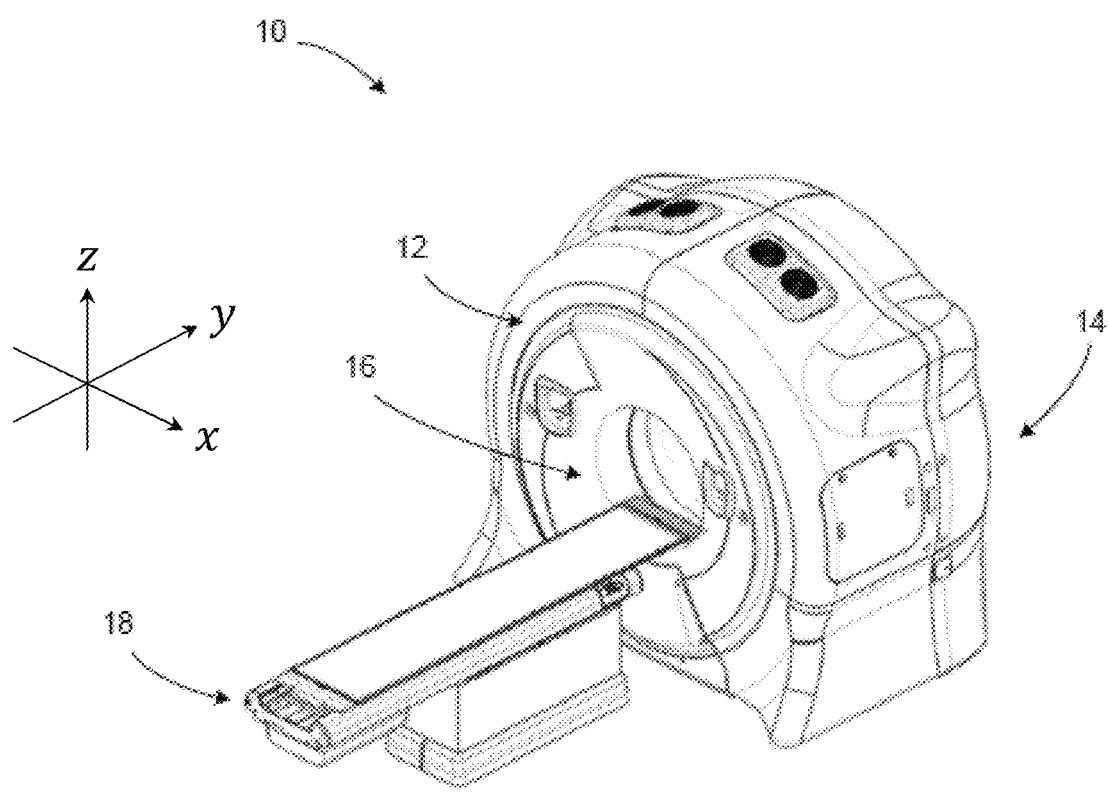
FIG. 1 is a perspective view of an exemplary multimodal radiotherapy apparatus in accordance with one aspect of the disclosed technology.

The following includes definitions of exemplary terms that may be used throughout the disclosure. Both singular and plural forms of all terms fall within each meaning.

"Component," as used herein can be defined as a portion of hardware, a portion of software, or a combination thereof. A portion of hardware can include at least a processor and a portion of memory, wherein the memory includes an instruction to execute. A component may be associated with a device.

"Logic," synonymous with "circuit" as used herein, includes but is not limited to hardware, firmware, software and/or combinations of each to perform a function(s) or an action(s). For example, based on a desired application or needs, logic may include a software-controlled microprocessor, discrete logic such as an application specific integrated circuit (ASIC), or other programmed logic device and/or controller. Logic may also be fully embodied as software.

"Processor," as used herein includes, but is not limited to, one or more of virtually any number of processor systems or stand-alone processors, such as microprocessors, microcontrollers, central processing units (CPUs), and digital signal processors (DSPs), in any combination. The processor may be associated with various other circuits that support operation of the processor, such as random access memory (RAM), read-only memory (ROM), programmable read-only memory (PROM), erasable programmable read-only memory (EPROM), clocks, decoders, memory controllers, or interrupt controllers, etc. These support circuits may be internal or external to the processor or its associated electronic packaging. The support circuits are in operative communication with the processor. The support circuits are not necessarily shown separate from the processor in block diagrams or other drawings.

"Signal," as used herein includes, but is not limited to, one or more electrical signals, including analog or digital signals, one or more computer instructions, a bit or bit stream, or the like.

"Software", as used herein, includes but is not limited to one or more computer readable and/or executable instructions that cause a computer, processor, logic, and/or other electronic device to perform functions, actions, and/or behave in a desired manner. The instructions may be embodied in various forms such as routines, algorithms, modules, or programs including separate applications or code from dynamically linked sources or libraries.

While the above exemplary definitions have been provided, it is Applicant's intention that the broadest reasonable interpretation consistent with this specification be used for these and other terms.

As is discussed in more detail below, embodiments of the disclosed technology relate to multimodal imaging/radiotherapy devices and methods. In some embodiments, a radiotherapy delivery device and method can make use of an integrated low-energy radiation source for imaging and a high-energy radiation source for treatment and/or imaging in conjunction with or as part of IGRT. In particular, for example, a radiotherapy delivery device and method can combine a low-energy collimated radiation source for imaging in a gantry using rotational (e.g., helical or step-and-shoot, with or without the ability to rotate continuously with the use of a slip-ring) image acquisition along with a high-energy radiation source for imaging and/or therapeutic treatment.

Complementary information and advantages can be exploited from a keV radiation source and an MeV radiation source. For example, the intrinsic contrast of soft tissues may be higher at low-energies, while there is no starvation of primary photons through wide or dense structures at high-energies. keV and MeV imaging data can be used to supplement each other to yield higher quality images. High quality volume imaging can be needed for visualization of targets and organs-at-risk (OARS), for adaptive therapy monitoring, and for treatment planning/re-planning. In some embodiments, the multimodal system can also be used for positioning, motion tracking, and/or characterization or correction capabilities.

The image acquisition methodology can include or otherwise make use of a multiple rotation scan, which may be, for example, a continuous scan (e.g., with a helical source trajectory about a central axis together with longitudinal movement of a patient support through a gantry bore), a non-continuous circular stop-and-reverse scan with incremental longitudinal movement of a patient support, step-and-shoot circular scans, etc.

In accordance with various embodiments, the multimodal apparatus collimates a radiation source, including, for example, into a cone beam or a fan beam using, for example, a beamformer (which may include a collimator) to limit the beam. In one embodiment, the collimated beam can be combined with a gantry that continuously rotates while the patient moves, resulting in a helical image acquisition.

In some embodiments, the time associated with increased scanning rotations to complete a high-quality volume image may be mitigated by high gantry rates/speed (e.g., using fast slip ring rotation, including, e.g., up to 10 revolutions per minute (rpm), up to 20 rpm, up to 60 rpm, or more rpm), high frame rates, and/or sparse data reconstruction techniques, to provide CT quality imaging on a radiation therapy delivery platform. Detectors (with various row/slice sizes, configurations, dynamic range, etc.), scan pitch, and/or dynamic collimation are additional features in various embodiments, including to selectively expose portions of the detector and selectively define active readout areas.

The multimodal apparatus and methods can provide selective and variable collimation of a radiation beam emitted by the source of radiation, including adjusting the radiation beam shape to expose less than the entire active area of an associated radiation detector (e.g., a radiation detector positioned to receive radiation from the x-ray radiation source). Also, exposing only a primary region of the detector to direct radiation allows shadowed regions of the detector to receive only scatter. In some embodiments, scatter measurements in the shadow region (and in some embodiments measurements in the penumbra region) of the detector can be used to estimate scatter in the primary region of the detector receiving projection data.

The multimodal apparatus and method can provide selective and variable detector readout areas and ranges, including adjusting the detector readout range to limit the active area of the detector for improved readout speed. For example, less than the available shadow region data may be read and used for scatter estimation. Combining selective readout with beamforming allows for various optimizations of scatter fitting techniques.

Some exemplary aspects of the apparatus that may implement the disclosed embodiments follow. It should be understood that the embodiments are not limited to the specific hardware and apparatuses disclosed herein. For example, any of the methods and algorithms disclosed herein may be implemented by the apparatuses disclosed in U.S. patent application Ser. No. 16/694,148, filed on Nov. 25, 2019, herein incorporated by reference in its entirety.

Figure 2A:
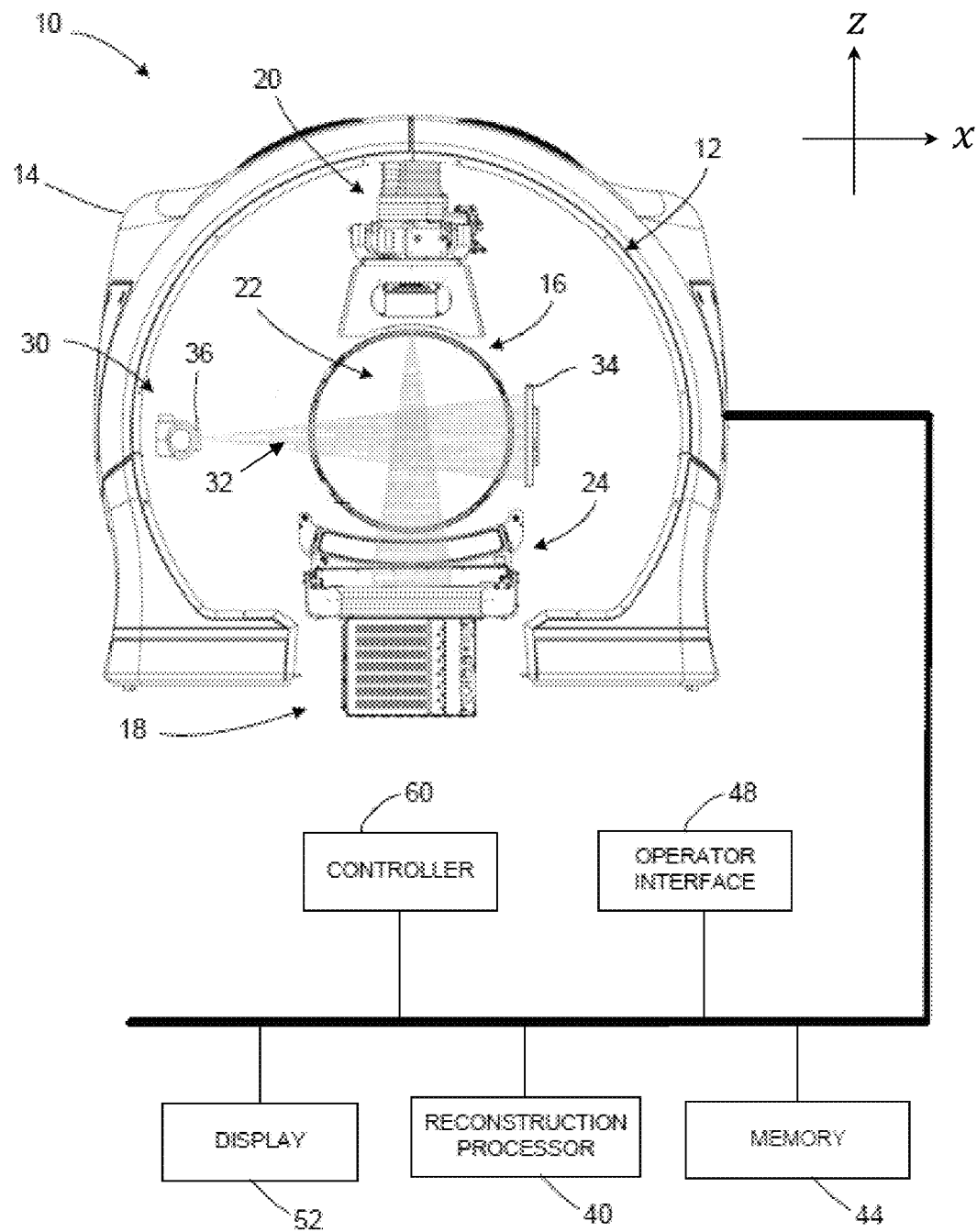
FIG. 2A is a diagrammatic illustration of an exemplary multimodal radiotherapy apparatus in accordance with one aspect of the disclosed technology.

With reference to FIG. 1 and FIG. 2A, a multimodal apparatus 10 is shown. It will be appreciated that the multimodal apparatus 10 may be associated with and/or integrated into a radiotherapy device (as shown in FIG. 2) that can be used for a variety of applications, including, but not limited to IGRT, for example, as an IGRT delivery system (e.g., IGRT delivery system 104 shown in FIG. 3 and discussed in detail below). The multimodal apparatus 10 includes a rotatable gantry system, referred to as gantry 12, supported by or otherwise housed in a support unit or housing 14. Gantry herein refers to a gantry system that comprises one or more gantries (e.g., ring or C-arm) capable of supporting one or more radiation sources and/or associated detectors as they rotate around a target. For example, in one embodiment, a first radiation source and its associated detector may be mounted to a first gantry of the gantry system and a second radiation source and its associated detector may be mounted to a second gantry of the gantry system. In another embodiment, more than one radiation source and associated detector(s) may be mounted to the same gantry of the gantry system, including, for example, where the gantry system is comprised of only one gantry. Various combinations of gantries, radiation sources, and radiation detectors may be combined into a variety of gantry system configurations to image and/or treat the same volume within the same apparatus. For example, keV and MeV radiation sources can be mounted on the same or different gantries of the gantry system and selectively used for imaging and/or treatment as part of an IGRT system. If mounted to different gantries, the radiation sources are able to rotate independently, but are still able to simultaneously image the same (or nearly the same) volume. A rotatable ring gantry 12 may be capable of 10 rpm or more, as mentioned above. The rotatable gantry 12 defines a gantry bore 16 into and through which a patient can be moved and positioned for imaging and/or treatment. In accordance with one embodiment, the rotatable gantry 12 is configured as a slip ring gantry to provide continuous rotation of radiation sources and associated radiation detector(s) while providing sufficient bandwidth for the high-quality imaging data received by the detector(s). A slip-ring gantry can eliminate gantry rotations in alternating directions in order to wind and unwind cables carrying the power and signals associated with the device. Such a configuration will allow for continuous helical computed tomography, including CBCT, even when integrated into an IGRT system. As mentioned above, a major issue with single rotation CBCT is insufficient sampling on all slices except for the central slice (the one containing the rotation). This can be overcome by helical trajectory cone-beam imaging.

A patient support 18 is positioned adjacent to the rotatable gantry 12 and configured to support a patient, typically in a horizontal position, for longitudinal movement into and within the rotatable gantry 12. The patient support 18 can move the patient, for example, in a direction perpendicular to the plane of rotation of the gantry 12 (along or parallel to the rotation axis of the gantry 12). The patient support 18 can be operatively coupled to a patient support controller for controlling movement of the patient and patient support 18. The patient support controller can be synchronized with the rotatable gantry 12 and sources of radiation mounted to the rotating gantry for rotation about a patient longitudinal axis in accordance with a commanded imaging and/or treatment plan. The patient support can also be moved in a limited range up and down, left and right once it is in the bore 16 to adjust the patient position for optimal treatment. Axes x, y, and z are shown, where, viewing from the front of the gantry 12, the x-axis is horizontal and points to the right, the y-axis points into the gantry plane, and the z-axis is vertical and points to the top. The x-, y-, and z-axes follow the right-hand rule.

As shown in FIG. 2A, the multimodal apparatus 10 includes a low-energy radiation source (e.g., keV) 30 coupled to or otherwise supported by the rotatable gantry 12. In this embodiment, the low-energy radiation source 30 is a source of imaging radiation and emits a radiation beam (indicated generally as 32) for generating high-quality images. In this embodiment, the source of imaging radiation is an x-ray source 30, configured as a kilovoltage (keV) source (e.g., a clinical x-ray source having a voltage in the range of about 20 keV to about 150 keV). In one embodiment, the keV source of radiation comprises a kilo-electron volt peak photon energy (keV) up to 150 keV. The imaging radiation source can be any type of transmission source suitable for imaging. For example, the imaging radiation source may be, for example, an x-ray generating source (including for CT) or any other way to produce photons with sufficient energy and flux (such as, e.g., a gamma-source (e.g., Cobalt-57, energy peak at 122 keV), an x-ray fluorescence source (such as fluorescence source through Pb k lines, two peaks @about 70 keV and @about 82 keV), etc.). References herein to x-ray, x-ray imaging, x-ray imaging source, etc. are exemplary for particular embodiments. Other imaging transmission sources can be used interchangeably in various other embodiments. An x-ray detector 34 (e.g., two-dimensional flat detector or curved detector) can be coupled to or otherwise supported by the rotatable gantry 12. The x-ray detector 34 is positioned to receive radiation from the x-ray source 30 and can rotate along with the x-ray source 30.

It will be appreciated that the x-ray detector 34 can take on a number of configurations without departing from the scope of the disclosed technology. As illustrated in FIG. 2A, the x-ray detector 34 can be configured as a flat-panel detector (e.g., a multi-row flat panel detector). In accordance with another exemplary embodiment, the x-ray detector 34 can be configured as a curved detector. The detector 34 can detect or otherwise measure the amount of radiation not attenuated and therefore infer what was in fact attenuated by the patient or associated patient ROI (by comparison to what was initially generated). The detector 34 can detect or otherwise collect attenuation data from different angles as the low-energy radiation source 30 rotates around and emits radiation toward the patient.

Although FIGS. 1 and 2A depict a multimodal apparatus 10 with a radiation source 30 mounted to a ring gantry 12, other embodiments may include other types of rotatable imaging apparatuses, including, for example, C-arm gantries and robotic arm-based systems. In gantry-based systems, a gantry rotates the imaging radiation source 30 around an axis passing through the isocenter. Gantry-based systems include C-arm gantries, in which the imaging radiation source 30 is mounted, in a cantilever-like manner, over and rotates about the axis passing through the isocenter. Gantry-based systems further include ring gantries, for example, rotatable gantry 12, having generally toroidal shapes in which the patient's body extends through a bore of the ring/toroid, and the imaging radiation source 30 is mounted on the perimeter of the ring and rotates about the axis passing through the isocenter. In some embodiments, the gantry 12 rotates continuously. In other embodiments, the gantry 12 utilizes a cable-based system that rotates and reverses repeatedly.

A collimator or beamformer assembly (indicated generally as 36) is positioned relative to the x-ray source 30 to selectively control and adjust a shape of a radiation beam 32 emitted by the x-ray source 30 to selectively expose a portion or region of the active area of the x-ray detector 34. The beamformer can also control how the radiation beam 32 is positioned on the x-ray detector 34. In one embodiment, the beamformer 36 could have one degree/dimension of motion (e.g., to make a thinner or fatter slit). In another embodiment, the beamformer 36 can have two degrees/dimensions of motion (e.g., to make various sized rectangles). In other embodiments, the beamformer 36 may be capable of various other dynamically-controlled shapes, including, for example, parallelograms. All of these shapes may be dynamically adjusted during a scan. In some embodiments, blocking portions of the beamformer can be rotated and/or translated.

The beamformer 36 can be controlled to adjust the shape of the radiation beam 32 emitted by the x-ray source 30 dynamically in a number of geometries, including, but not limited to, a fan beam or cone beam having a beam thickness (width) as low as one detector row width or including multiple detector rows, which may be only a portion of the detector's active area. In various embodiments, the thickness of the beam may expose several centimeters of a larger detector active area. For example, 3-4 centimeters (measured in the longitudinal direction in the detector plane) of a 5-6 centimeter detector may be selectively exposed to the imaging radiation 32. In this embodiment, 3-4 centimeters of projection image data may be captured with each readout, with about 1-2 centimeters of unexposed detector area on one or each side, which may be used to capture scatter data, as discussed below.

In other embodiments, more or less of a portion of the active detector may be selectively exposed to the imaging radiation. For example, in some embodiments, the beam thickness may be reduced down to about two centimeters, one centimeter, less than one centimeter, or ranges of similar sizes, including with smaller detectors. In other embodiments, the beam thickness may be increased to about 4 centimeters, 5 centimeters, greater than 5 centimeters, or ranges of similar sizes, including with larger detectors. In various embodiments, the ratio of exposed-to-active detector area may be 30-90% or 50-75%. In other embodiments, the ratio of exposed-to-active detector area may be 60-70%. However, various other exposed and active area sizes or ratios of exposed-to-active detector area may be suitable in other embodiments. The beam and detector can be configured so that the shadowed region of the detector (active but not exposed to direct radiation) is sufficient to capture scatter data beyond the penumbra region.

Various embodiments may include an optimization of the features that control selective exposure of the detector (e.g., beam size, beam/aperture center, collimation, pitch, detector readout range, detector readout center, etc.) such that the measured data is sufficient for primary (exposed) and shadowed regions, but also optimized for speed and dosage control. The beamformer 36 shape/position and detector 34 readout range can be controlled such that the radiation beam 32 from the x-ray source 30 covers as much or as little of the x-ray detector 34 based on the particular imaging task and scatter estimation process being carried out, including, for example, combinations of narrow and wide FOV scans. The apparatus 10 has the ability to acquire both single rotation cone beam and wide and narrow beam angle cone beam images, helical or other.

The beamformer 36 may be configured in a variety of ways that allow it to adjust the shape of the radiation beam 32 emitted by the x-ray source 30. For example, the beamformer 36 can be configured to include a set of jaws or other suitable members that define and selectively adjust the size of an aperture through which the radiation beam from the x-ray source 30 may pass in a collimated manner. In accordance with one exemplary configuration, the beamformer 36 can include an upper jaw and a lower jaw, where the upper and lower jaws are movable in different directions (e.g., parallel directions) to adjust the size of the aperture through which the radiation beam from the x-ray source 30 passes, and also to adjust the beam 32 position relative to the patient to illuminate only the portion of the patient to be imaged for optimized imaging and minimized patient dose.

In accordance with one embodiment, the shape of the radiation beam 32 from the x-ray source 30 can be changed during an image acquisition. Stated differently, in accordance with one exemplary implementation, the beamformer 36 leaf positions and/or aperture width can be adjusted before or during a scan. For example, in accordance with one embodiment, the beamformer 36 can be selectively controlled and dynamically adjusted during rotation of the x-ray source 30 such that the radiation beam 32 has a shape with sufficient primary/shadow regions and is adjusted to include only an object of interest during imaging (e.g., the prostate). The shape of the radiation beam 32 being emitted by the x-ray source 30 can be changed during or after a scan, depending on the desired image acquisition, which may be based on imaging and/or therapeutic feedback, as discussed in more detail below.

As shown in FIG. 2A, the multimodal apparatus 10 may be integrated with a radiotherapy device that includes a high-energy radiation source (e.g., MeV) 20 coupled to or otherwise supported by the rotatable gantry 12. In accordance with one embodiment, the high-energy radiation source 20 is configured as a source of therapeutic radiation, such as a high-energy source of radiation used for treatment of a tumor within a patient in a region of interest. In other embodiments, the high-energy radiation source 20 is also configured as a source of imaging radiation, or at least utilized as such. It will be appreciated that the source of therapeutic radiation can be a high-energy x-ray beam (e.g., MeV x-ray beam), and/or a high-energy particle beam (e.g., a beam of electrons, a beam of protons, or a beam of heavier ions, such as carbon) or another suitable form of high-energy radiation. In one embodiment, the high-energy radiation source 20 comprises a mega-electron volt peak photon energy (MeV) of 1 MeV or greater. In one embodiment, the high-energy x-ray beam has an average energy greater than 0.8 MeV. In another embodiment, the high-energy x-ray beam has an average energy greater than 0.2 MeV. In another embodiment, the high-energy x-ray beam has an average energy greater than 150 keV. Generally, the high-energy radiation source 20 has a higher energy level (peak and/or average, etc.) than the low-energy radiation source 30.

In one embodiment, the high-energy radiation source 20 is a LINAC producing therapeutic radiation (e.g., MeV) and the imaging system comprises an independent low-energy radiation source 30 producing relatively low intensity and lower energy imaging radiation (e.g., keV). In other embodiments, the therapeutic radiation source 20 could be a radioisotope, such as, for example, Co-60, which can generally have energy >1 MeV. The high-energy radiation source 20 can emit one or more beams of radiation (indicated generally by 22) toward a region-of-interest (ROI) within a patient supported on the patient support 18 in accordance with a treatment plan.

In various embodiments, the high-energy radiation source 20 is utilized as a source of therapeutic radiation and a source of imaging radiation. As discussed in detail below, sources of radiation 20, 30 may be used in conjunction with one another to provide higher quality and better utilized images. References to the therapeutic radiation source 20 herein are to distinguish the high-energy radiation source 20 from the low-energy radiation source 30, which may be used only for imaging. However, references to the therapeutic radiation source 20 include embodiments where the therapeutic radiation source 20 (high-energy radiation source) can be utilized for therapy and/or imaging. In other embodiments, at least one additional radiation source can be coupled to the rotatable gantry 12 and operated to acquire projection data at a peak photon energy distinct from the peak photon energies of sources of radiation 20, 30.

Detector 24 can be coupled to or otherwise supported by the rotatable gantry 12 and positioned to receive radiation 22 from the therapeutic radiation source 20. The detector 24 can detect or otherwise measure the amount of radiation not attenuated and therefore infer what was in fact attenuated by the patient or associated patient ROI (by comparison to what was initially generated). The detector 24 can detect or otherwise collect attenuation data from different angles as the therapeutic radiation source 20 rotates around and emits radiation toward the patient.

It will be further appreciated that the therapeutic radiation source 20 can include or otherwise be associated with a beamformer or collimator. The beamformer associated with the therapeutic radiation source 20 can be configured in a number of ways, similar to the beamformer 36 associated with the imaging source 30. For example, a beamformer can be configured as a multi-leaf collimator (MLC), which can include a plurality of interlaced leaves operable to move to one or more positions between a minimally-open or closed position and a maximally-open position. It will be appreciated that the leaves can be moved into desired positions to achieve a desired shape of a radiation beam being emitted by the radiation source. In one embodiment, the MLC is capable of sub-millimeter targeting precision.

The therapeutic radiation source 20 may be mounted, configured, and/or moved into the same plane or a different plane (offset) than the imaging source 30. In some embodiments, scatter caused by simultaneous activation of the radiation sources 20, 30 may be incrementally reduced by offsetting the radiation planes. In other embodiments, scatter can be avoided by interleaving the activations. For example, with simultaneous multimodal imaging, the acquisitions can be concurrent, without having concurrent individual pulses. In another embodiment, use of shadow-based scatter correction can be used, for example, to address the problem of MeV scatter on a keV detector.

When integrated with a radiotherapy device, multimodal apparatus 10 can provide images that are used to set up (e.g., align and/or register), plan, and/or guide a radiation delivery procedure (treatment). Typical set-up is accomplished by comparing current (in-treatment) images to pre-treatment image information. Pre-treatment image information may comprise, for example, CT data, cone-beam CT data, MRI data, PET data or 3D rotational angiography (3DRA) data, and/or any information obtained from these or other imaging modalities. In some embodiments, the multimodal apparatus 10 can track in-treatment patient, target, or ROI motion.

A reconstruction processor 40 can be operatively coupled to detector 24 and/or detector 34. In one embodiment, the reconstruction processor 40 is configured to generate patient images based on radiation received by the detectors 24, 34 from the radiation sources 20, 30. It will be appreciated that the reconstruction processor 40 can be configured to be used to carry out the methods described more fully below. The apparatus 10 can also include a memory 44 suitable for storing information, including, but not limited to, processing and reconstruction algorithms and software, imaging parameters, image data from a prior or otherwise previously-acquired image (e.g., a planning image), treatment plans, and the like.

The multimodal apparatus 10 can include an operator/user interface 48, where an operator of the apparatus 10 can interact with or otherwise control the apparatus 10 to provide input relating to scan or imaging parameters and the like. The operator interface 48 can include any suitable input devices, such as a keyboard, mouse, voice-activated controller, or the like. The apparatus 10 can also include a display 52 or other human-readable element to provide output to the operator of the apparatus 10. For example, the display 52 can allow the operator to observe reconstructed patient images and other information, such as imaging or scan parameters, related to operation of the apparatus 10.

As shown in FIG. 2A, the multimodal apparatus 10 includes a controller (indicated generally as 60) operatively coupled to one or more components of the apparatus 10. The controller 60 controls the overall functioning and operation of apparatus 10, including providing power and timing signals to the x-ray source 30 and/or the therapeutic radiation source 20 and a gantry motor controller that controls rotational speed and position of the rotatable gantry 12. It will be appreciated that the controller 60 can encompass one or more of the following: a patient support controller, a gantry controller, a controller coupled to the therapeutic radiation source 20 and/or the x-ray source 30, a beamformer controller, a controller coupled to the detector 24 and/or the x-ray detector 34, and the like. In one embodiment controller 60 is a system controller that can control other components, devices, and/or controllers.

In various embodiments, the reconstruction processor 40, the operator interface 48, the display 52, the controller 60 and/or other components may be combined into one or more components or devices.

The apparatus 10 may include various components, logic, and software. In one embodiment, the controller 60 comprises a processor, a memory, and software. By way of example and not limitation, a multimodal apparatus and/or radiotherapy system can include various other devices and components (e.g., gantries, radiation sources, collimators, detectors, controllers, power sources, patient supports, among others) that can implement one or more routines or steps related to imaging and/or IGRT for a specific application, wherein a routine can include imaging, image-based pre-delivery steps, and/or treatment delivery, including respective device settings, configurations, and/or positions (e.g., paths/trajectories), which may be stored in memory. Furthermore, the controller(s) can directly or indirectly control one or more devices and/or components in accordance with one or more routines or processes stored in memory. An example of direct control is the setting of various radiation source or collimator parameters (power, speed, position, timing, modulation, etc.) associated with imaging or treatment. An example of indirect control is the communication of position, path, speed, etc. to a patient support controller or other peripheral device. The hierarchy of the various controllers that may be associated with the apparatus can be arranged in any suitable manner to communicate the appropriate commands and/or information to the desired devices and components.

Moreover, those skilled in the art will appreciate that the systems and methods may be implemented with other computer system configurations. The illustrated aspects of the invention may be practiced in distributed computing environments where certain tasks are performed by local or remote processing devices that are linked through a communications network. For example, in one embodiment, the reconstruction processor 40 may be associated with a separate system. In a distributed computing environment, program modules may be located in both local and remote memory storage devices. For instance, a remote database, a local database, a cloud-computing platform, a cloud database, or a combination thereof can be utilized with apparatus 10.

Multimodal apparatus 10 can utilize an exemplary environment for implementing various aspects of the invention including a computer, wherein the computer includes the controller 60 (e.g., including a processor and a memory, which may be memory 44) and a system bus. The system bus can couple system components including, but not limited to the memory to the processor, and can communicate with other systems, controllers, components, devices, and processors. Memory can include read only memory (ROM), random access memory (RAM), hard drives, flash drives, and any other form of computer readable media. Memory can store various software and data, including routines and parameters, which may comprise, for example, a treatment plan.

The therapeutic radiation source 20 and/or x-ray source 30 can be operatively coupled to a controller 60 configured to control the relative operation of the therapeutic radiation source 20 and the x-ray source 30. For example, the x-ray source 30 can be controlled and operated simultaneously with the therapeutic radiation source 20. In addition, or alternatively, the x-ray source 30 can be controlled and operated sequentially with the therapeutic radiation source 20, depending on the particular treatment and/or imaging plan being implemented. For example, in various embodiments, the radiation sources 20, 30 can be operated such that the measured projection data from the radiation sources 20, 30 are acquired simultaneously (or essentially/nearly (quasi-) simultaneous, e.g., within about 50 ms of each other) or sequentially (e.g., separated by seconds, minutes, etc.)

It will be appreciated that radiation sources 20, 30 and detector(s) 24, 34 can be configured to provide rotation around the patient during an imaging and/or treatment scan in a number of ways. In one embodiment, synchronizing the motion and exposure of the source 20, 30 with the longitudinal motion of the patient support 18 can provide a continuous helical acquisition or scan of a patient image during a procedure. In addition to continuous rotation of the radiation sources 20, 30 and detector(s) 24, 34 (e.g., continuous and constant rotation of the gantry with constant patient motion speed), it will be appreciated that other variations can be employed without departing from the scope of the disclosed technology. For example, the rotatable gantry 12 and patient support can be controlled such that the gantry 12 rotates in a "back-and-forth" manner (e.g., alternating clockwise rotation and counterclockwise rotation) around a patient supported on the patient support (as opposed to continuously, as is described above) as the support is controlled to move (at a constant or variable speed) relative to the rotatable gantry 12. In another embodiment, with successive step-and-shoot circular scans, movement of the patient support 18 in the longitudinal direction (step) alternates with a scanning revolution by the rotatable gantry 12 (shoot) until the desired volume is captured. The multimodal apparatus 10 is capable of volume-based and planar-based imaging acquisitions. For example, in various embodiments, the multimodal apparatus 10 may be used to acquire volume images and/or planar images and execute the associated processing, including scatter estimation/correction methods described below.

Various other types of radiation source and/or patient support movement may be utilized to achieve relative motion of the radiation source and the patient for generation of projection data. Non-continuous motion of the radiation source and/or patient support, continuous but variable/non-constant (including linear and non-linear) movement, speed, and/or trajectories, etc., and combinations thereof may be used, including in combination with the various embodiments of apparatus 10 described above.

In one embodiment, the gantry 12 rotation speed, the patient support 18 speed, the beamformer shape, and/or the detector readout could all be constant during image acquisition. In other embodiments, one or more of these variables could change dynamically during image acquisition and/or treatment. The gantry 12 rotation speed, patient support 18 speed, beamformer shape, and/or detector readout can be varied to balance different factors, including, for example, image quality, image acquisition time, dosage, workflow, etc.

In other embodiments, these features can be combined with one or more other image-based activities or procedures, including, for example, patient set up, adaptive therapy monitoring, treatment planning, etc.

Multi-Energy Data Acquisition and Analysis

As discussed above, the authors show that using MeV and keV sourced x-rays together in multi-modal analysis can enhance imaging. Much of the enhancement depends on spectrally resolving the individual keV and MeV energy ranges. In particular, spectral resolution can reveal materials properties of imaged tissue through understanding the mechanism of x-ray/tissue interaction and its energy dependence.

Figure 2B:
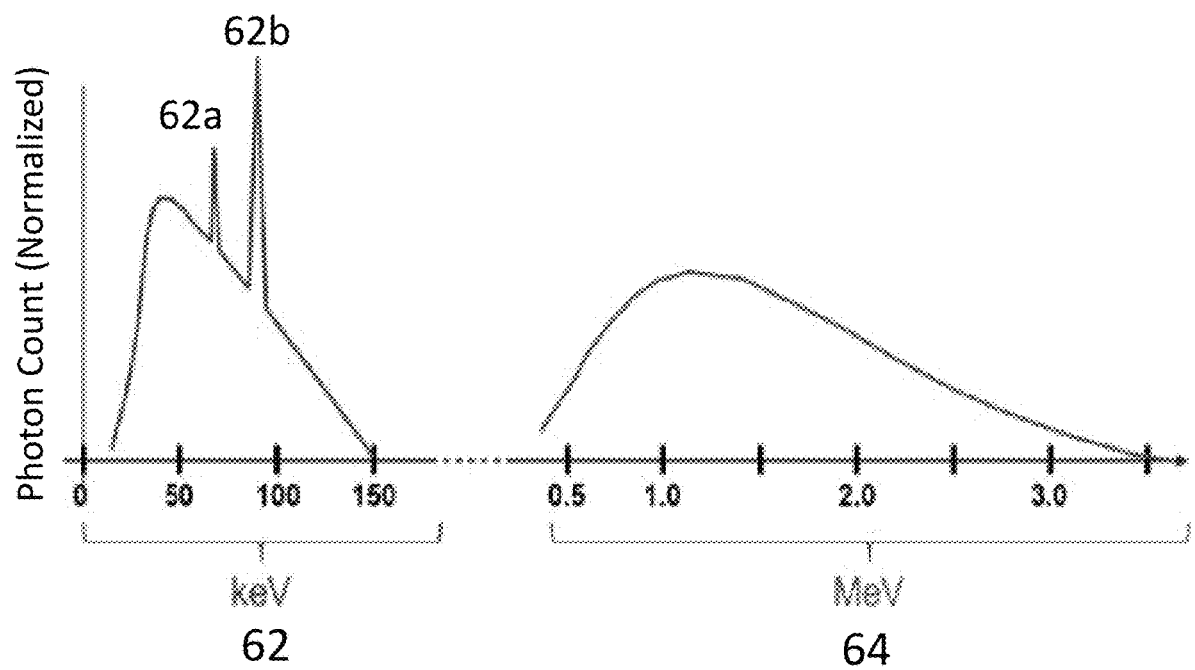
FIG. 2B is an illustration of MeV and keV photon energy ranges that may be used in spectral imaging via, for example, the apparatus in FIG. 2A.

FIG. 2B is an illustration of MeV 64 and keV 62 photon energy ranges that may be used in spectral imaging via, for example, the apparatus in FIG. 2A. The keV range 62 corresponds to detected x-ray photons ultimately deriving from low-energy radiation source 30 used primarily for imaging. Features 62a and 62b in the spectrum 62 represent characteristic lines of the tungsten anode used to generate the keV x-rays. The MeV range 64 corresponds to x-ray photons ultimately deriving from high-energy radiation source 20 that may be used in imaging and for radiotherapy. It is to be understood that other radiation sources can be used either in the keV or the MeV range. Some embodiments may include multiple MeV and/or keV sources, for example.

In spectral analysis, detected x-ray photons are resolved or sorted according to 1) their overall energy range (keV 62/MeV 64) and 2) their specific energy within the overall energy range. Energy resolution depends on the particular detection technique and apparatus. For example, each overall range keV/MeV may be ascertained based on the position of the detector with respect to the source. As shown in FIG. 2A, MeV x-rays 64 from source 20 are detected by detector 24. keV x-rays 62 from source 36 are detected by detector 34. The specific energy of each detected photon must be ascertained by the detector itself, as described in more detail below.

Once individual photon energies in a keV or MeV mode are detected, a detected spectrum may be built from the data. The spectrum is created by subdividing ranges keV 62 and MeV 64 into discreet energy segments. The energy segments can, for example, be used in a histogram to bin detected photons by energy, which will be discussed in more detail below. Doing so can create a useful detected x-ray photon energy distribution.

Figure 2C:
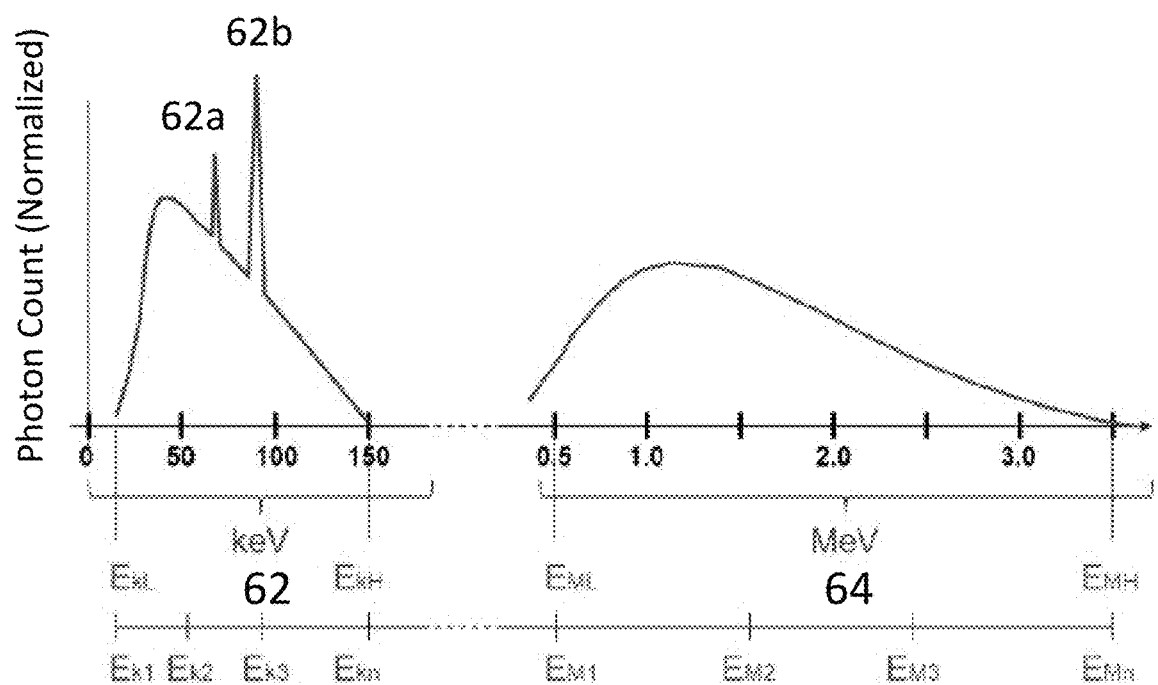
FIG. 2C is an illustration of spectral differentiation of the spectra shown in FIG. 2B.

FIG. 2C shows an exemplary division of keV and MeV ranges into sub-ranges or sub-divisions. The keV range 62 should cover from $E_{kL}$ to $E_{kH}$, (indices k for keV, "L" for low, "H" for High). Similarly, the MeV range 64 could be $E_{ML}$ to $E_{MH}$. In another example, keV 62 and MeV 64 ranges can further be decomposed (with the appropriate detection technology) into a series of sub-ranges, e.g. $E_{k1}$-$E_{k2}$, $E_{k2}$-$E_{k3}$, ... $E_{kn-1}$-$E_{kn}$, with a similar sub-division on the MeV range e.g. $E_{M1}$-$E_{M2}$, $E_{M2}$-$E_{M3}$, ... $E_{Mn-1}$-$E_{Mn}$. It is to be understood that these ranges are exemplary and any other suitable range may be used. Energy ranges can be chosen based on the specific application discussed below.

Figure 2D:
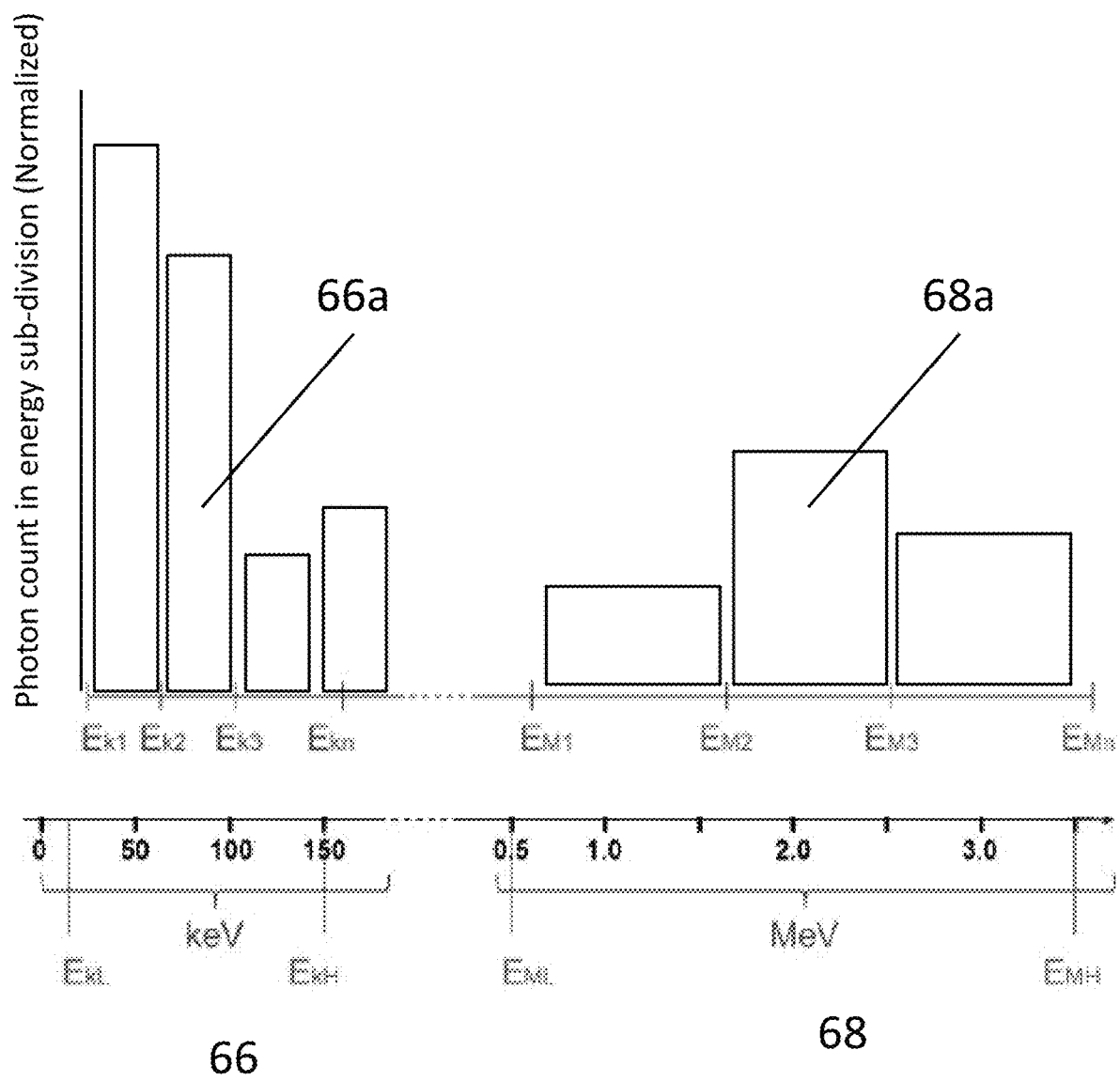
FIG. 2D shows histograms for spectral analysis based on the spectra in FIG. 2A.

FIG. 2D shows two exemplary histograms, one for the keV range 66 and one for the MeV range 68. Each bar in the histograms (e.g., bars 66a and 68a) represents a number of x-ray photons detected in the relevant energy range ($E_{k2}$-$E_{k3}$ for 66a and $E_{M2}$-$E_{M3}$ for 68b). The histograms 66 and 68 will be referred to below in the context of spectral analysis.

Types of X-Ray Detection in Spectral Analysis

Different x-ray detection methods lend themselves to multi-modal, spectral analysis. Two methods explored in the context of the present disclosure are energy integrating and energy discriminating technology. Detectors 24 and 34 in FIG. 2A may include either energy integrating or energy discriminating technology, or both. These particular methods are discussed in detail below. However, it is to be understood that concepts disclosed herein are general enough to apply to other detection methods not explicitly disclosed here. Moreover, detectors 24 and 34 are not limited to these technologies and can encompass any suitable detection technology.

Energy integrating detectors generate a continuous current based on detected x-ray flux. That continuous detector current depends on the energy distribution of detected x-rays contributing to it, as well details of the particular detector. For example, an energy integrating scintillator detector detects x-ray photons when they strike a scintillator to create visible light. The light can be turned into current via photodetector, such as a photodiode. The diode detection current is related both to the x-ray flux and energy. This is because high-energy x-rays cause a more intense scintillated light emission, resulting in a higher current generated by the diode. Because of this, high energy x-rays within a spectrum portion (e.g., $E_{kH}$ withing the keV 62 portion and $E_{MH}$ within the MeV 64 portion (FIG. 2C)), contribute more to a detection current than lower-energy x-rays (e.g., $E_{kL}$ withing the keV 62 portion and $E_{ML}$ within the MeV 64 portion (FIG. 2C)).

The incident x-ray beam generated by a radiotherapy apparatus comprises x-ray photons having a range of energies. This means that photons contributing to the detector current will also have a wide range of energy levels. Resolving the energy of incident photons in an energy integrating detector configuration is not trivial. A small amount of higher energy x-rays can create the same current as a greater amount of low energy x-rays. For this reason, energy integrating detection can be less useful in spectral analysis. It can still be useful, however, by employing different x-ray spectra for data acquisition such that the energy integrating detectors could capture information from different energy ranges of the same material (e.g., where each, different x-ray application is associated with a specific bin $E_{k1}$-$E_{k2}$, $E_{k2}$-$E_{k3}$, ... $E_{kn-1}$-$E_{kn}$ in either the keV 62 range or the corresponding bins in the MeV 64 range), which can be further utilized for spectral imaging.

In contrast, energy discriminating detection or spectral detection provides a more direct accounting for individual x-ray photon energy. Specifically, energy discriminating detectors detects each individual x-ray photon as a single event, rather than creating a continuous current from multiple detection events. Each individual photon can be assigned an energy level corresponding to a histogram binning discussed above (e.g., an energy level associated with one of bins $E_{k1}$-$E_{k2}$, $E_{k2}$-$E_{k3}$, ... $E_{kn-1}$-$E_{kn}$ in either the keV 66 histogram or the MeV 68 histogram). Thus the output of an energy discriminating detector can be used directly in spectral analysis.

In scintillation energy discriminating detection, energy level is determined from a measure of the amount of light created by when an individual x-ray photon strikes a scintillator. The scintillated light's intensity can be measured using methods of photodetection, including using a photodiode or other semiconductor device. In this case, the charge created by the photon/device interaction can be related to the energy of the photon Still other detection schemes are contemplated within the context of the present disclosure. For example, photon counting may also or alternatively be used. Photon counting can determine a flux rate of incident x-rays. In photon counting, photon detection events are individually counted, but the individual energy level of the counted photons is not assessed.

Energy Weighting

At least three x-ray interactions with tissue in the keV and MeV ranges can be exploited in the context of the present disclosure. These are: photoelectric effect interactions, Compton scattering, and pair production. The energy and mass dependence of each can be exploited to provide materials information not otherwise apparent from single model x-ray analysis. Each interaction is described briefly below with relation to its utility in multi modal image analysis.

Photoelectric Effect

The photoelectric effect is a principal way x-rays interact with matter. It dominates at the low end of the keV spectrum 62 (e.g., below 30 keV).

In the photoelectric effect, x-ray photon interaction with an inner shell electron in the target material removes the electron from its shell. The incident photon is absorbed and detected as an attenuation of the x-ray beam as it passes through the material (i.e., as an attenuation of the detected signal). When an outer shell electron fills the inter shell vacancy, either an x-ray photon or an Auger electron is emitted. If an x-ray photon is emitted, its energy will reflect the energy difference between inner and outer shells, characteristic of the material. Therefore, the detected photon can be used for materials characterization.

The probability of photoelectric absorption is $(Z/E)^3$, where Z is the atomic number of the tissue atom and E is the photon energy. The strong, third power dependence of absorption on the atomic number Z of tissue material provides significant information for material identification. This strong dependence also provides a means of differentiating photoelectric effect x-rays from those deriving from the other effects described herein that do not have such a strong Z dependence. Sporadic discontinuities for specific elements at specific energies caused by x-ray absorption edges also help identify those specific elements. These too can be exploited within the context of the present invention for that purpose.

Compton Effect Scattering

Compton scattering results from an inelastic collision of an x-ray photon and a charged particle. It dominates x-ray interaction with tissue for photons having an energy between 30 keV and 30 MeV.

In the context of the present disclosure, Compton scattering can be used in conjunction with the photoelectric effect for materials analysis. This is because the dependency on atomic number (Z) for these phenomena is so different. In contrast with the photoelectric effect's third power Z dependence, Compton attenuation essentially does not depend on atomic number. Therefore, the relative proportion of Compton and photoelectric scattering events can reveal materials properties of the tissue being interrogated.

Compton attenuation can also be distinguished from other sources by its characteristic energy dependence. The effect varies relatively little with energy in the keV range. Its attenuation, however, is inversely proportional to energy in the MeV range.

Pair Production

Pair production in x-ray analysis typically refers to a photon creating an electron/positron pair near a nucleus. It requires incident photon energies above 1.022 MeV. Its cross section surpasses the Compton Effect x-ray cross section at the high end of the treatment spectrum (e.g., above 2 MeV) and for high Z materials.

Pair production attenuation has a relatively strong mass dependence that lends itself to materials characterization, particularly for high Z materials at high energies. Specifically, its mass attenuation coefficient is approximately proportional to atomic number and increases as the logarithm of x-ray energy in the MeV range. The relatively strong Z dependence may allow for material discrimination between high- and low-atomic-number materials (e.g., bone from soft tissue).

Detection Schemes for Spectral Differentiation

Authors propose using a photon counting detection scheme to capitalize on photoelectric effect photons to improves materials characterization.

Photon counting detectors provide the sensitivity to relatively low energy (≤30 keV) photoelectric effect photons necessary to take advantage of their materials characterization advantages. This is because photon counting, unlike other techniques (e.g., energy integrating analysis), is not biased in favor of higher energy photons. Such bias would wash out the relatively low energy photoelectric effect contribution. In addition, a judicious choice of energy binning can isolate valuable low energy (keV) photons from less informative high energy photons, further preventing the high energy dominance over the relatively low energy photoelectric effect. In particular, binning MeV detection into a high and low-energy (e.g., bins centered around $E_{ML}$ and $E_{MH}$, FIG. 2C) can isolate the highest energy MeV photons. This arrangement is useful for sources that produce a high flux of MeV x-rays, but also include substantial numbers of keV photons whose differentiation from the MeV could lend itself to materials analysis.

Examined Cases and Options

Four separate cases A-D, or subdivision of keV and MeV ranges were examined and tested:

$$E_{[E_{ML}-E_{MH}]}+E_{[E_{kL}-E_{kH}]} \quad A$$

$$E_{[E_{M1}-E_{M2}]}+E_{[E_{M2}-E_{Mn}]}+E_{[E_{kL}-E_{kH}]} \quad B$$

$$E_{[E_{ML}-E_{MH}]}+E_{[E_{k1}-E_{k2}]}+E_{[E_{k2}-E_{kn}]} \quad C$$

$$E_{[E_{M1}-E_{M2}]}+E_{[E_{M2}-E_{Mn}]}+E_{[E_{k1}-E_{k2}]}+E_{[E_{k2}-E_{kn}]} \quad D$$

In case A, there are two bins, one for the entire MeV range ($E_{[EML-EMH]}$) and one for the entire keV range ($E_{[EkL-EkH]}$). In case B, the MeV range is decomposed into n sub-ranges ($E_{[M1-M2]}+E_{[M2-Mn]}$), while the keV range is not ($E_{[EkL-EkH]}$). In case C, the keV range is decomposed into n sub-ranges ($E_{[k1-k2]}+E_{[k2-kn]}$), while the MeV range is not ($E_{[EML-EMH]}$).

In case D, both the keV range ($E_{[k1-k2]}+E_{[k2-kn]}$) and MeV range ($E_{[M1-M2]}+E_{[M2-Mn]}$) are decomposed into n sub-ranges.

Energy Weighting in Image Analysis

Techniques for assessing how certain MeV/keV spectral combinations allow for high-quality decomposition of computed tomography images into multiple basis materials were examined. The basis materials include soft tissue and bone. The developed techniques improve visualization of certain anatomical fiducial points. They also allow for quantitative calculation of x-ray absorption coefficients used in radiotherapy dosimetry.

Specifically, an energy weighting analysis reliant on at least one of an energy-integrating detection system and information from an energy-discriminating system for enhancing information extraction from x-ray images of tissue collected by keV/MeV sources was derived. In particular, they observed how a combination of information extraction from multiple techniques can enhance image interpretation. For example, the ability to weight lower-energy x-rays more heavily than higher-energy x-rays can lead to higher contrast-to-noise ratios was observed. Single line-integral ideal SNR (all detected photons with optimal energy weighting) improved keV spectrum interpretation in nearly all tasks studied. These and other examples are discussed in more detail below.

Modeling is accomplished via a dual-energy decomposition of a single line through an imaged object into its line integral contributions from soft tissue and bone. The quality of this decomposition compares favorably to that obtained using a more conventional high- and low-energy kilovoltage pair commonly employed in commercial dual-energy CT Three of the detector types discussed above: energy-integrating detectors, photon-counting, and spectral photon-counting using the Cramer-Rao lower bound formalism (CRLB), as more specifically described in E. Roessl and C. Herrmann, "Cramér-Rao lower bound of basis image noise in multiple-energy x-ray imaging.," Phys Med Biol, vol. 54, no. 5, pp. 1307-1318, March 2009, herein incorporated by reference in its entirety. They calculate the lowest achievable variance on the material line integral estimates and use the ratio of the actual line integral to the square root of this variance as signal-to-noise ratio (SNRs) for assessing the potential quality of the decomposition.

The nature of the images from the keV and MeV sources (referred to herein as an "imaging chain") are so different that new optimization routines need to be developed for their combination. In particular, signal to noise in each keV/MeV imaging chain differ substantially. Each particular imaging task (e.g., achieving low contrast detectability of metal artifact-free guiding images) may require a different treatment. For example, the x-ray dose distribution among the different imaging chains/different energy ranges may need to be adjusted for each task. The modeling effort below sheds light on such optimization. It shows how it can be accomplished such that noise in combined keV and MeV imaging is within useful range. The model assumes equal splitting of dose from the keV and MeV spectra. This may not be an optimal division. The same formalism could provide guidance for dose splitting.

Single Line Integral Model

Figure 2E:
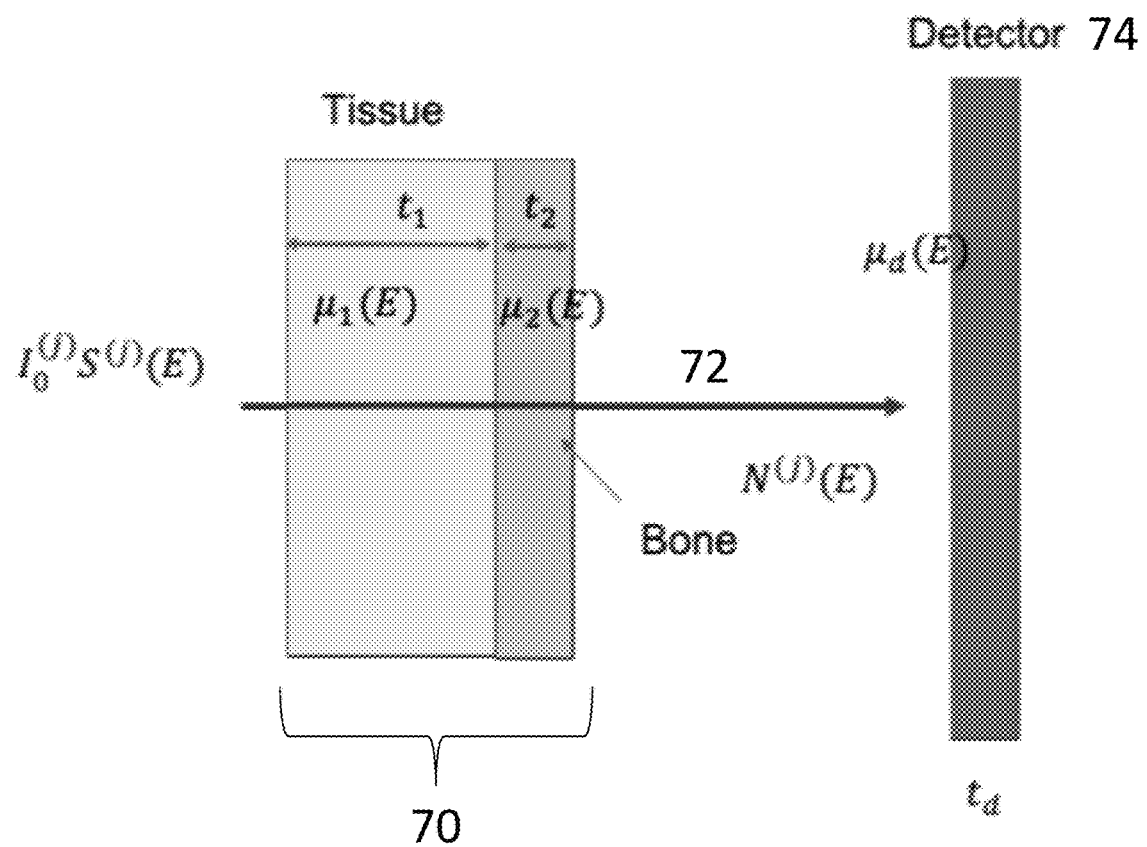
FIG. 2E calculation parameters and model for spectral analysis noise estimation.

FIG. 2E shows the model setup. The model in includes patient material 70 comprising a layer of soft tissue ("Tissue") and "Bone." Integration proceeds along the line path 72 through the patient material 70. The model predicts the x-ray detection at detector 74 after traversing the patient material 70. Detector 74 includes energy-integrating, photon-counting, and spectral photon-counting capabilities.

The model assumes Tissue to have a thickness of $t_1$ (cm) and a linear attenuation coefficient $\mu_1$ (E)(cm$^{-1}$). $\mu_1$ can be calculated by multiplying a tabulated mass attenuation coefficient for soft tissue:

$$\left[\frac{\mu}{\rho}(E)\right]_1 (cm^2/g)$$

by an assumed material density of the soft tissue material density $\rho_1$(g/cm$^3$):

$$\mu_1(E) = \left[\frac{\mu}{\rho}(E)\right]_1 \rho_1 \quad (1)$$

The Bone is assumed to have thickness $t_2$ (cm) and linear attenuation coefficient $\mu_2$(E)(cm$^{-1}$), which has the same form as pi in Equation 1. For compactness, we define the following parameter:

$$f_i(E) \equiv \left[\frac{\mu}{\rho}(E)\right]_i \quad (2)$$

where i=1, 2 for $\mu_1$ and $\mu_2$, respectively.

X-Ray Spectrum

As shown in FIG. 2E, patient material 70 is illuminated with a spectrum described by fluence $I_0^{(j)}$(cm$^{-2}$), which is the number of incident photons per cm$^2$ in the spectrum for the jth measurement.

$Z^{(j)}$(E) is the energy distribution of those photons in units of keV$^{-1}$. This spectrum is normalized such that:

$$\int Z^{(j)}(E)dE = 1$$

The differential dE has units of keV to make the integral unitless.

Number of Photons Transmitted Through Patient Material 70 and Incident on Detector 74

The number of photons of energy E incident on a detector pixel of area w (cm$^2$) is given by:

$N^{(j)}(E) = I_0^{(j)} Z^{(j)}(E) T(E) w^2$ where transmission is given by:

$T(E) = \exp[-\mu_1(E)t_1 - \mu_2(E)t_2]$

Using $f_i$ (Equation 2) to consolidate:

$T(E) = \exp[-f_1(E)\rho_1 t_1 - f_2(E)\rho_2 t_2]$

Defining for convenience:

$A_i \equiv \rho_i t_i$

This notation is consistent with the concept that the line integral through a uniform density of $\rho_1$(g/cm$^3$) and length $t_i$ is given by their product. Therefore:

$T(E) = \exp[-f_1(E)A_1 - f_2(E)A_2]$

Probability That Detector 74 Absorbs a Photon

The probability that a detector 74 in measurement j detects a photon of energy E is denoted $n_j$(E). This is given by:

$\eta_j(E) = 1 - \exp(-\mu_d(E)t_d)$ where $t_d$ is the thickness of detector 74 and $\mu_d$ (E) is the linear attenuation coefficient of the detector material:

$$\mu_d(E) = \left[\frac{\mu}{\rho}(E)\right]_d \rho_d$$

Response of Detector 74 to an Absorbed Photon

The response of detector 74 to an x-ray photon of energy E is denoted by $\psi_j$ (E). The subscript j denotes that detector 74 records multiple measurements for a given illumination of the object. Detector 74 incorporates elements of an energy integrating detector, an ideal photon counting detector, a spectral detector. The responses of each of these elements are explored below.

Energy Integrating Detector

In an energy-integrating detector, x-rays liberate electrons in proportion to their energy, giving rise to a measurable current. A more energetic x-ray will cause a larger signal. The response is:

$\psi_j(E) = \alpha E$ where $\alpha$ represents a constant of proportionality. The units of $\alpha$ depend on the units of the signal (e.g., amperes/keV). For convenience, we can take $\alpha=1$.

Ideal Photon Counting Detector

An ideal photon counting detector will increment one signal count when the energy of a detected photon is within the energy range or bin associated with the counter. This would generate the following detector signal:

$\psi_j(E) = 1$

Spectral Counting Detector

In a spectral photon counting detector, the energy of each detection event can be assigned a predetermined energy bin. The assignment is based on an estimate of the energy of the incoming photon. In an exemplary system with four bins (e.g., keV range 62 and MeV range 64 shown in FIG. 2C), this is generally represented as $[E_1, E_2]$, $[E_2, E_3]$, $[E_3, E_4]$, $[E_4, E_5]$. $E_5$ can be taken as infinite ($E_5=\infty$). Doing so creates a threshold for detected photons. In this situation, the detector signal is given by:

$\psi_j(E) = 1$, if $E \in [E_j, E_{j+1}]$ $= 0$, otherwise.

An average value of measurement j is given by:

$\lambda^{(j)} = w^2 I_0^{(j)} \int Z^{(j)}(E)\eta_j(E)\psi_j(E)\exp[-f_1(E)A_1 - f_2(E)A_2]dE$ (3a)

A spectral weighting factor S can distinguish between keV and MeV ranges:

$S_j(E) \equiv Z^{(j)}(E)\eta_j(E)\psi_j(E)$

The expectation value of the measurement is:

$\lambda^{(j)} = w^2 I_0^{(j)} \int S_j(E)\exp[-f_1(E)A_1 - f_2(E)A_2]dE$ (3b)

In dual-energy (keV and MeV) CT, two measurements $\lambda(j)$ are acquired using different spectral weightings $S_j$(E). This results in two non-linear equations (3a and 3b) that can be solved for two unknowns $A_1$ and $A_2$.

$\lambda^{(j)}$ will generally include some noise. $\lambda^{(j)}$ will be Poisson distributed for photon counting detectors. In energy integrating detectors, energy weighting means $\lambda^{(j)}$ will be a weighted sum of Poisson random variables, which is not Poisson.

Lower Bound on Variance of $A_i$ Estimates

The Cramer-Rao lower bound (CRLB), as described in more detail in: Kay S M 1993 Fundamentals of statistical signal processing Estimation Theory vol 1 (Englewood Cliffs, N.J.: Prentice Hall), herein incorporated by reference in its entirety, gives a good estimate of variance in the estimates of $A_i$. One would expect to achieve this lower bound according to maximum likelihood estimation. Assuming $\lambda^{(j)}$ are Poisson distributed:

$$\sigma_{A_1}^2 = \frac{(m_{12}^2/\lambda_2) + (m_{22}^2/\lambda_2)}{(m_{11}m_{22} - m_{12}m_{21})^2}$$

and:

$$\sigma_{A_2}^2 = \frac{(m_{11}^2/\lambda_2) + (m_{21}^2/\lambda_1)}{(m_{11}m_{22} - m_{12}m_{21})^2}$$

where:

$$m_{ji} = \frac{\partial \ln \lambda_j}{\partial A_i} = \frac{w^2 I_0^{(j)} \int S_j(E) \exp[-f_1(E)A_1 - f_2(E)A_2][-f_i(E)] dE}{w^2 I_0^{(j)} \int S_j(E) \exp[-f_1(E)A_1 - f_2(E)A_2] dE}$$

In estimating noise, two principal sources in the measurement acquired by an energy integrating detector are considered. The first derives from the fact that Poissonian photon-counting statistics govern the number of x-rays actually absorbed in the detector. Each such x-ray contributes to the signal $\lambda^{(j)}$ in proportion to its energy with constant of proportionality $\alpha$. The weighted sum of Poisson random variables is not Poisson. However, it follows a compound Poisson distribution. In addition, there may be electronic readout noise, which can be modeled as additive zero-mean Gaussian electronic noise with variance $\sigma e^2$. The readout noise is independent of the compound Poisson noise. The sum of a compound Poisson and a Gaussian distribution can be approximated as a Gaussian with mean and variance matching the first two moments of the actual distribution. This is an especially good approximation when the number of detected x-rays per channel exceeds ten, which is likely.

Overall, the mean measurement for a given spectral weighting j is:

$$M_j = \alpha w^2 I_0^{(j)} \int E S_j(E) \exp[-f_1(E)A_1 - f_2(E)A_2] dE$$

which is the same as $\lambda^{(j)}$ above (Equation 3) with the extra factor of E in the integral and the multiplicative constant $\alpha$.

The model assumes that variance of the overall Gaussian will be given by the sum of the variance due to the compound Poisson and that due to the readout noise:

$$\sigma_j^2 = \alpha^2 w^2 I_0^{(j)} \int E^2 S_j(E) \exp[-f_1(E)A_1 - f_2(E)A_2] dE + \sigma_e^2$$

In the above expression, both $\alpha$ and E are squared. This is because all other terms, at a given E, give the mean of the Poisson random variable corresponding to the number of x-rays detected at E. Then $\alpha$ and E multiply that Poisson random variable.

In this context, the CRLB states that the variance of the kth material line integral estimate will be greater than or equal to the kth diagonal element of the inverse Fisher information matrix ($\mathcal{F}_{kk}^{-1}$), as described in more detail in Kay S M 1993 Fundamentals of statistical signal processing Estimation Theory vol 1 (Englewood Cliffs, N.J.: Prentice Hall), herein incorporated by reference in its entirety:

$$\sigma_{A_k}^2 \geq \mathcal{F}_{kk}^{-1}$$

As shown in E. Roessl and C. Herrmann, "Cramér-Rao lower bound of basis image noise in multiple-energy x-ray imaging.," Phys Med Biol, vol. 54, no. 5, pp. 1307-1318, March 2009, herein incorporated by reference in its entirety, for uncorrelated Gaussian noise, $\mathcal{F}^{-1}$ is the inverse of the matrix with elements:

$$\mathcal{F}_{\alpha\beta} = E\left[-\frac{\partial^2 \mathcal{L}}{\partial A_\alpha \partial A_\beta}\right] \tag{4}$$

$$= \sum_{j=1}^{2} \frac{1}{\sigma_j^2} \frac{\partial M_j}{\partial A_\alpha} \frac{\partial M_j}{\partial A_\beta} + \frac{1}{2}\sum_{j=1}^{2} \frac{1}{(\sigma_j^2)^2} \frac{\partial \sigma_j^2}{\partial A_\alpha} \frac{\partial \sigma_j^2}{\partial A_\beta}$$

Now:

$$\frac{\partial M_j}{\partial A_i} = -\alpha w^2 I_0^{(j)} \int f_i(E) E S_j(E) \exp[-f_1(E)A_1 - f_2(E)A_2] dE$$

i.e., the derivative will also pull out a factor of $-f_i(E)$.
Finally:

$$\frac{\partial \sigma_j^2}{\partial A_i} = -\alpha^2 w^2 I_0^{(j)} \int f_i(E) E^2 S_j(E) \exp[-f_1(E)A_1 - f_2(E)A_2] dE$$

i.e., the derivative will add a factor of $-f_i(E)$. The model can assume no readout noise (i.e., $\sigma_e = 0$ and $\alpha = 1$).

We construct a 2×2 matrix $\mathcal{F}_{\alpha\beta}$ using the Equation 4 above. We can use diagonal elements of the inverse of $\mathcal{F}_{\alpha\beta}$ as the CRLBs of $\sigma_{A_1}^2$ and $\sigma_{A_2}^2$. The final figures of merit (FOM) will be:

$$SNR_1 = A_1/\sigma_{A_1}^2 \tag{5a}$$

$$SNR_2 = A_2/\sigma_{A_2}^2 \tag{5b}$$

Equations (5a) and (5b) can be evaluated for a variety of detectors, spectra, material pairs, and material amounts. The key comparison will be between the FOMs achieved with a typical 80 keV-140 keV spectral pair used in dual energy CT, versus a megavoltage spectrum combined with a keV spectrum such as 120 keV.

Combined MeV/keV SNR Estimates

Spectra:

The example SNR estimates that follow consider combinations of 4 spectra: 1) a low-energy kilovoltage spectrum ("80 keV" or "80 kVp"), 2) 140 keV ("140 keV" or "140 kVp"), 3) a 6 MeV treatment spectrum ("6 MeV" or "6 MV"), and 4) a "detuned" spectrum more suitable for imaging ("detuned").

Figure 2F:
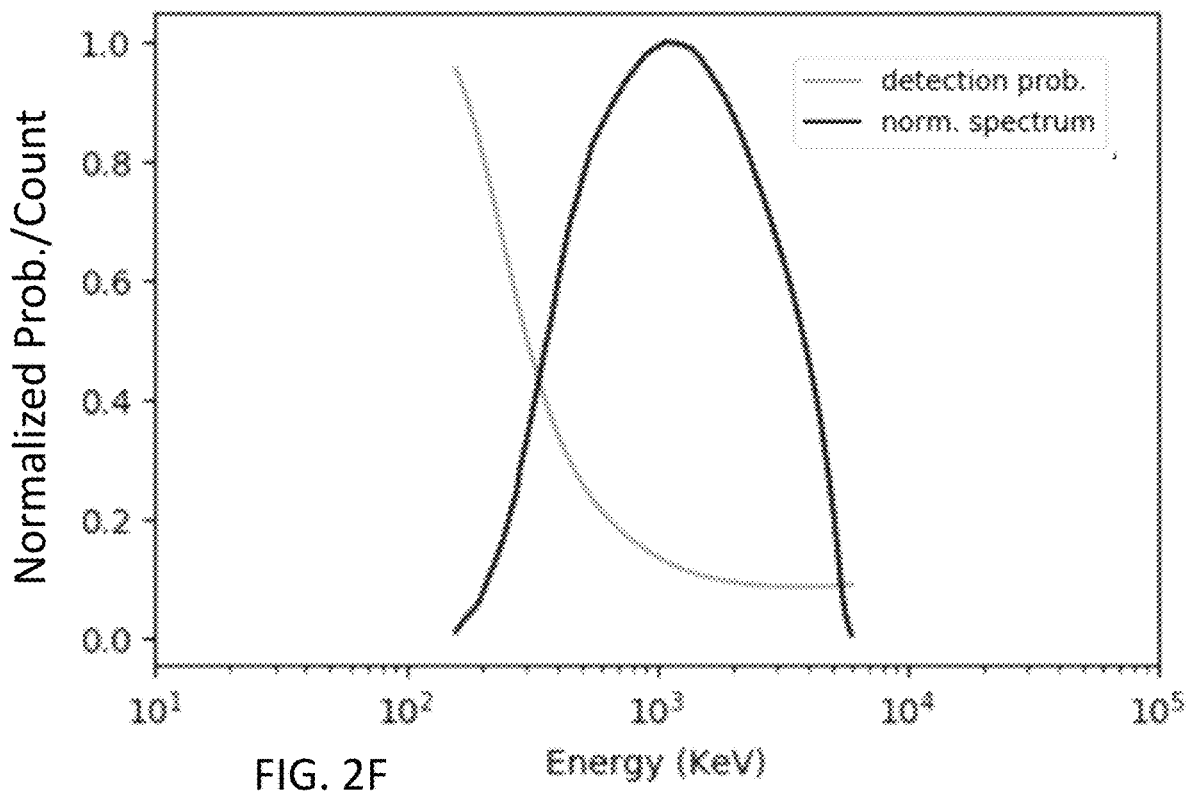
FIG. 2F shows both the normalized spectrum and detection probably vs. energy of a 6 MeV treatment beam.
Figure 2G:
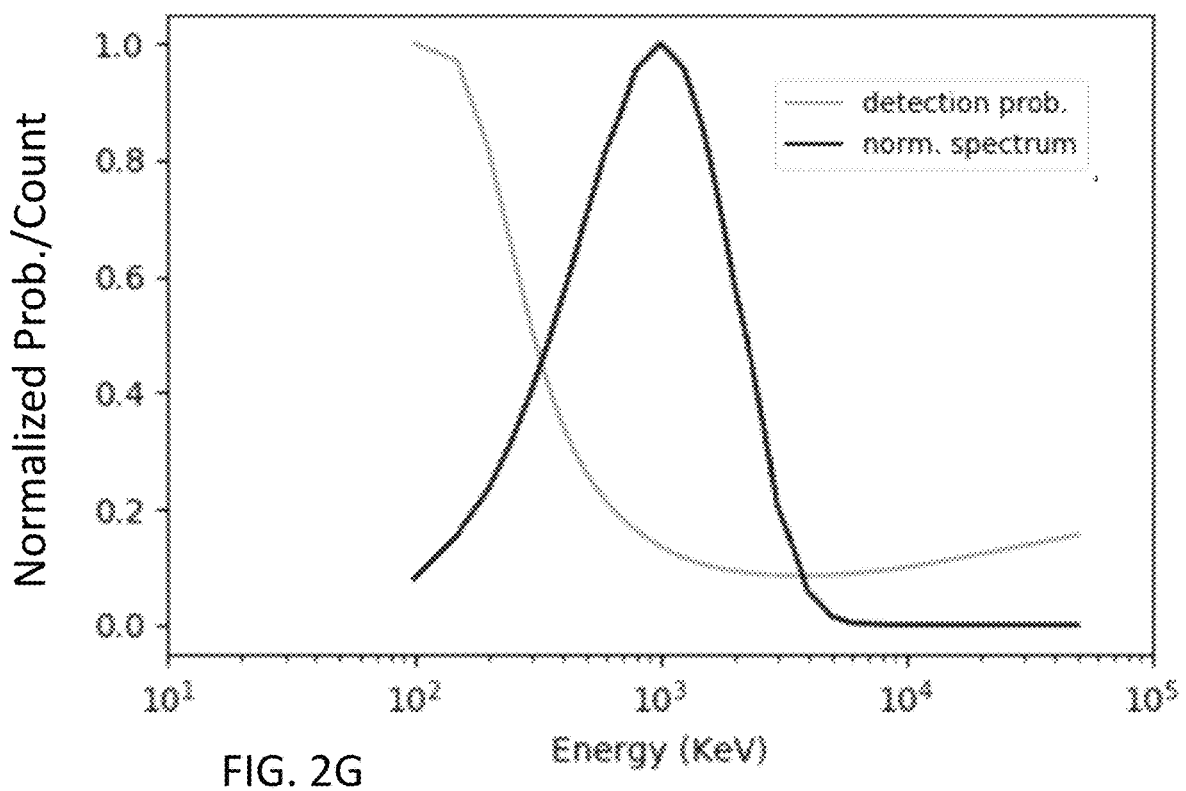
FIG. 2G shows the normalized spectrum and detection probably for a detuned beam.

FIG. 2F shows both the normalized spectrum and detection probably vs. energy of the 6 MeV treatment beam. For comparison, FIG. 2G shows the normalized spectrum and detection probably for the detuned beam. The "detuned" spectrum represents a spectrum from an MeV treatment source that has settings more appropriate for imaging than treatment. In particular, detuned settings include running the MV source such that photons produced would have less than 1 MeV, generally close to 0.5 MeV. Authors have determined that x-rays from the MeV source in this range are more suitable for MeV imaging.

In the calculations, the incident beams were scaled to deliver the same radiation dose. Specifically, radiation flux from each of the four sources was scaled to deliver the same dose to the center of a 40 cm diameter cylinder of water. As discussed below, this is likely a good approximation of soft tissue dose. Since MeV x-rays provide a higher dose per photon, this scaling means fewer MeV photons than keV photons are detected and available for imaging. More specifically, the scaling reduces the fluence of the 6 MeV and detuned x-rays in bone and soft tissue to at least an order of magnitude less than the 140 keV x-rays.

Model Specifics:

In the calculations, the soft tissue density was estimated at $\rho_1=1.0$ g/cm$^3$ and the bone density was $\rho_2=1.85$ g/cm$^3$. The distance of the line integral in soft tissue was 40 cm. As discussed in more detail below, the line integral distance in bone varied between 1 cm and 5 cm, depending on the particular calculation.

Results:

Ratios of the line integrals through each material to the standard deviations of the estimates of those line integral are calculated according to equations 5a and 5b. These are denoted $SNR_t=A_t/\sigma_t$ for soft tissue and $SNR_b=A_b/\sigma_b$ for bone.

When the values of $SNR_t$ and $SNR_b$ are higher, this means that the relative noise is lower. Therefore, higher $SNR_t$ and $SNR_b$ indicates a better potential image quality. If $SNR_t$ and $SNR_b$ from a large number of line integrals are fed into a tomographic reconstruction algorithm to form images of bone and soft tissue separately, higher $SNR_t$ and $SNR_b$ will yield better images.

Results were obtained by combining two of the four different spectra discussed above. All six possible combinations were explored. $SNR_t$ and $SNR_b$ for these combinations is given in Table 1 below. The two spectra in the combination are indicated as "Spectrum 1" and "Spectrum 2" in Table 1. Calculations for Table 1 were made with a model having 1 cm of the line integral dedicated to bone and 40 cm dedicated to soft tissue.

TABLE 1

Signal to noise estimates for 6 different spectral combinations when the detector is in photocounting mode and the model has 1 cm of bone and 40 cm of soft tissue.

| Spectral Combination | Spectrum 1 | Spectrum 2 | $SNR_t$ ($A_t/\sigma_t$) | $SNR_b$ ($A_b/\sigma_b$) |
|---|---|---|---|---|
| 1 | 6 MV | detuned | 1.0 | 0.045 |
| 2 | 6 MV | 80 kVp | 64 | 4.7 |
| 3 | 6 MV | 140 kVp | 41 | 2.4 |
| 4 | detuned | 80 kVp | 83 | 6.0 |
| 5 | detuned | 140 kVp | 53 | 3.1 |
| 6 | 80 kVp | 140 kVp | 120 | 7.7 |

Table 1 shows best potential imaging performance (i.e., highest $SNR_t$ and $SNR_b$) in the case of the 80 kVp/140 kVp (i.e., spectral combination 6). It also shows that highest energy combination 1 has the least potential for good imaging performance. Below we discuss why these results are expected and can be taken as a confirmation of the modeling technique.

With regard to combination 6, 80 kVp/140 kVp is a current imaging standard in CT imaging. The benefits of this combination are well known in the art. Therefore, its best performance in Table 1 is expected. As the standard, $SNR_t$ and $SNR_b$ of combination 6 will be compared to the other five spectral combinations 1-5.

With regard to combination 1, this results from the combination of the two MV spectra. That combination 1 shows the lowest values for both $SNR_t$ and $SNR_b$, is expected because this combination has the lowest detected signal due to the dose scaling described above. More specifically, since photon flux is scaled according to dose, 6 MV and detuned sources have the lowest photon contribution to the detected signal. Spectral combination 1 combines those two lowest photon signals and, therefore, has the lowest signal to noise.

Surprisingly, the results for combinations 2-5 indicate reasonably good potential for imaging. Generally, an SNR above 1 may have some imaging value. Both $SNR_t$ and $SNR_b$ are higher than 1 for each of combinations 2-5.

Somewhat unexpectedly, combination 4, including both the detuned and 80 kVp spectra, is the second highest in terms of SNR, after the standard combination 6. In fact, combination 4's $SNR_t$ is nearly 70% that of standard combination 6. Combination 4's $SNR_b$ is nearly 78% standard combination 6's $SNR_b$. These results strongly suggest potential for combination 4 to provide useful imaging data, at least in the photon counting regime.

Because of the difference in operation explained above, photon counting detectors are expected to provide more useful imaging and spectral information from higher energy sources than energy integrating detectors. This is because photon counting detectors do not weight in favor of higher energy x-rays, the x-rays that tend to be less useful for imaging information. These expectations are partially borne out in model results for the energy integrating detection scheme shown in Table 2 below.

TABLE 2

Signal to noise estimates for 6 different spectral combinations when the detector is in energy integrating mode and the model has 1 cm of bone and 40 cm of soft tissue.

| Spectral Combination | Spectrum 1 | Spectrum 2 | $SNR_t$ ($A_t/\sigma_t$) | $SNR_b$ ($A_b/\sigma_b$) |
|---|---|---|---|---|
| 1 | 6 MV | detuned | 1.0 | 0.047 |
| 2 | 6 MV | 80 kVp | 49 | 3.5 |
| 3 | 6 MV | 140 kVp | 27 | 1.5 |
| 4 | Detuned | 80 kVp | 61 | 4.4 |
| 5 | Detuned | 140 kVp | 34 | 1.9 |
| 6 | 80 kVp | 140 kVp | 120 | 7.9 |

As shown in Table 2, the overall trend in the data for energy integrating mode mirror those for the photo counting mode in Table 1. Again combination 6, the 80 kVp/140 kVp standard, has the highest $SNR_t$ and $SNR_b$. Since the spectra in combination 6 are both relatively low energy, switching the detector from photon counting to integrating mode does not substantially degrade its resolution. Again we see that combination 1, the high energy 6 MV and detuned (MV) spectra, has the lowest SNR. Like for combination 6, SNR for combination 1 is also not dramatically affected by the change in detector mode. Since all photons in combination 1 are high energy, the difference between detection schemes should have less effect. Also the SNR for combination 1 was likely near minimum even in the case of photon counting. Therefore, switching to energy integrating was not likely to push SNR substantially lower.

Again SNR for combinations 2-5 is reasonably high when compared standard combination 6. However, Table 2 shows a consistent decrease in resolution for these values in energy integrating mode vs. photon counting mode (Table 1). This is because energy integrating up-weights the highest energy photons, the least informative for imaging. The lowest energy photons are the most informative for discriminating bone and soft tissue.

Table 2 shows that the SNR for combination 4 (including both the detuned and 80 kVp spectra) is again the second highest in terms of SNR. This is despite a slight decrease in SNR from photon counting case (Table 1). Here combination 4's resolution is still quite high. In particular, its $SNR_b$ is several times greater than 1. In fact, its $SNR_t$ is more than 50% the highest value for standard combination 6. Its value for $SNR_b$ is nearly 56% the highest value for standard combination 6. These results strongly suggest potential for combination 4 to provide useful imaging data, even in the energy integrating regime.

Table 3 presents results when an energy integrating detector is used with additional bone added to the model. In this case, the model has 5× as much bone (i.e., 5 cm of bone in 40 cm of soft tissue).

TABLE 3

Signal to noise estimates for 6 different spectral combinations when the detector is in energy integrating mode and the model has 5 cm of bone and 40 cm of soft tissue.

| Spectral Combination | Spectrum 1 | Spectrum 2 | $SNR_t$ $(A_t/\sigma_t)$ | $SNR_b$ $(A_b/\sigma_b)$ |
|---|---|---|---|---|
| 1 | 6 MV | detuned | 0.88 | 0.20 |
| 2 | 6 MV | 80 kVp | 35 | 11 |
| 3 | 6 MV | 140 kVp | 17 | 4.4 |
| 4 | detuned | 80 kVp | 41 | 13 |
| 5 | detuned | 140 kVp | 20 | 5.3 |
| 6 | 80 kVp | 140 kVp | 43 | 12 |

Table 3 shows that, expectedly, increasing the amount of bone in the model decreases $SNR_t$ and increases $SNR_b$ for all combinations. Again we see that combination 6 (the imaging standard: 80 kVp/140 kVp) still has the highest SNR. Combination 1 has the lowest. The reasons are the same as those described above in the context of Tables 1 and 2.

Interestingly, combination 4 (detuned/80 kVp) has the second highest $SNR_t$ and the highest $SNR_b$. SNR of combinations 4 and 6 differ by only 5-8%, far less than in any case explored above. This suggests that, as the amount of bone increases, the relative resolution of combination 4 increases to near parity with that of the standard combination 4. It suggests that combination 4 may even be more accurate than the standard combination 6 as the amount of bone is increased further. With regard to the remaining high energy combinations (i.e., combinations 2, 3, and 5), they all show an increase in SNR relative to combination 6 as the amount of bone is increased.

The above results should be caveated by the following observation. The dose matching performed for kVp and MV contributions may not hold as the amount of bone is increased. Authors are currently exploring the effect of dose matching on these results.

Dose matching notwithstanding, the above results show definitively that a combined spectrum using MV and kVp x-rays (i.e., combination 4 of detuned and 80 kVp) can provide useful imaging, at least in terms of SNR. They further suggest that images with this and other high energy spectral combinations may provide imaging pathways when the x-ray beam encounters a high percentage of highly absorbing material (e.g., bone).

Prostate Imaging Example

The inventors tested the above-described methodologies on a computer generated cardiac-torso phantom model 78 including bone, prostate, and other soft tissue. A phantom model is a known computational, virtual model of human anatomy and physiology. The inventors used phantom 78 to show the difference between imaging capabilities of 120 keV, 6 MeV treatment, and detuned x-ray beams for these different types of tissue. Phantom 78 included parameterized organ models for a specified for an average patient.

The 120 keV beam showed contrast between bone, prostate and other soft tissue in phantom 78. In particular, there was some contrast at the prostate. However, the contrast was moderate and the prostate was difficult to differentiate from its surroundings. The image from the 120 keV beam also shows evidence of high contrast near the bone. It showed evidence of bone-based beam hardening. The beam hardening manifests as streaks emanating from the bony anatomy and leading to artifactual variability in the soft tissue regions as well as loss of contrast in some areas. The modeling applied only a water-based beam hardening correction that appeared to be insufficient for bone. The reconstruction was modeled as noiseless.

Also modeled was the image of phantom 78 using a noiseless 6 MeV treatment beam (FIG. 2F). The results showed contrast between the prostate and surrounding tissue was improved over the 120 keV case. The 6 MeV image showed no sign of beam hardening.

Phantom 78 was also imaged with x-rays from the detuned beam (FIG. 2G). The 6 MeV and detuned images exhibit similar contrast and a similar lack of beam hardening effects. Comparison of the images of the prostate from the 120 keV and 6 MeV beams showed improved contrast for the 6 MeV image. Prostate contrast in the detuned image was slightly better than for the 6 MeV beam.

The modeling results show, unexpectedly, that prostate contrast is higher for the MeV beams than for the 120 keV beam. They also show how MeV beams can provide imaging information with relatively little effects from beam hardening and good contrast between bone and soft tissue. More generally, the SNR and image models combined show how MeV spectra benefit more from photon counting detection than does keV. They also show how MeV beams can outperform keV for detection of high Z materials (e.g., bone) in strongly absorbing backgrounds.

Figure 3:
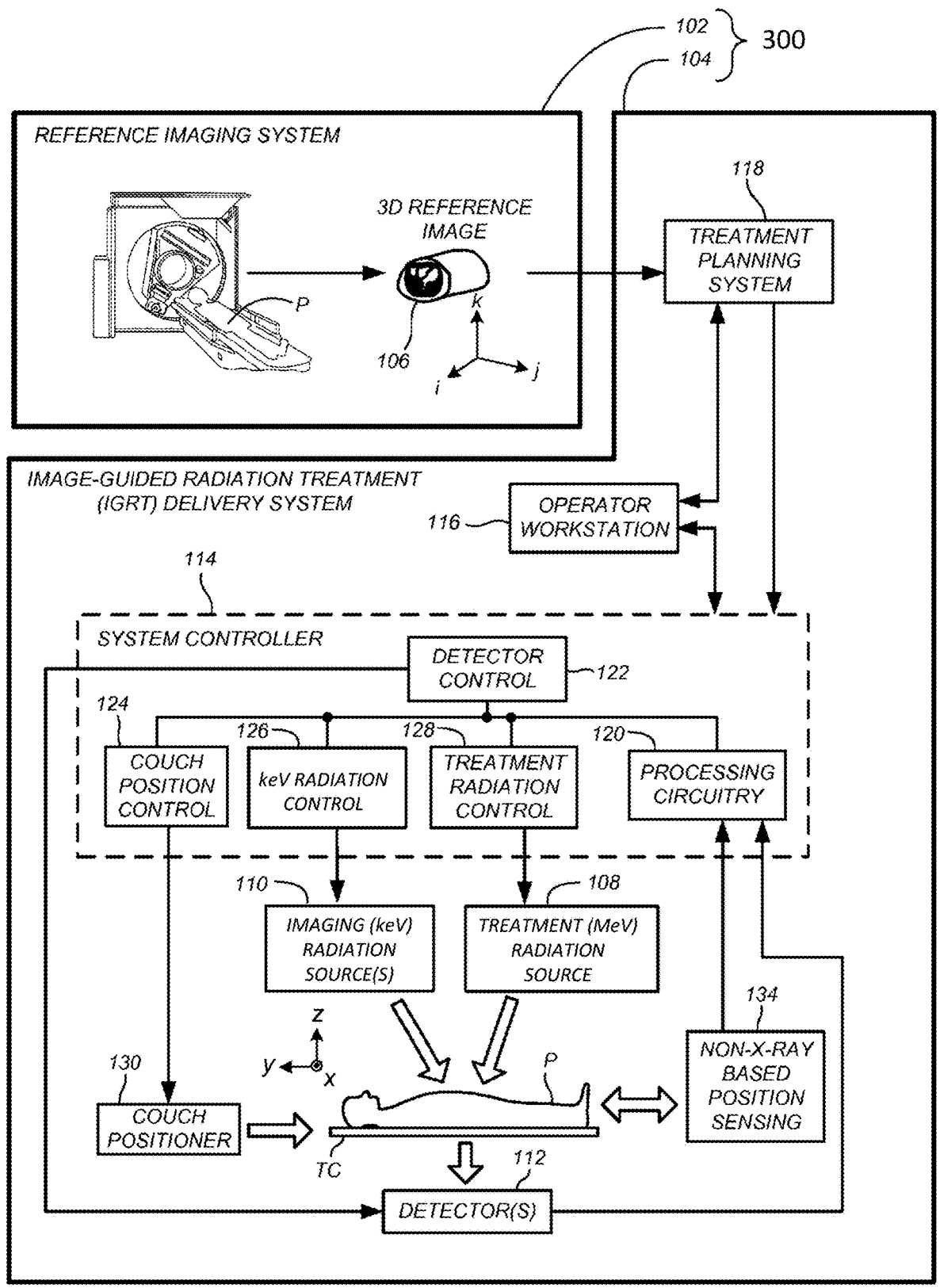
FIG. 3 illustrates an exemplary radiation treatment environment.

FIG. 3 illustrates an exemplary radiation treatment environment 300. The radiation treatment environment 300 includes a reference imaging system 102 and an IGRT system 104. The IGRT system 104 may comprise, for example, the multimodal apparatus 10 and its various components and devices as described above.

In one embodiment, the reference imaging system 102 can include a high precision volumetric imaging system such as, for example, a CT system or a MRI system. In view of cost and workflow considerations in many clinical environments, the reference imaging system 102 is often a general purpose tool used for a variety of different purposes in the clinic or hospital environment, and is not specifically dedicated to the IGRT system 104 or environment 300. Rather, the reference imaging system 102 may be located in its own separate room or vault and is purchased, installed, and/or maintained on a separate and more generalized basis than the IGRT system 104. Accordingly, for the embodiment of FIG. 3, the reference imaging system 102 is illustrated as being distinct from the IGRT system 104. In other embodiments, the reference imaging system 102 may be considered as an integral component of the IGRT system 104. For example, the multimodal apparatus 10 has the capability to act as the reference imaging system 102 and the IGRT system 104.

In this embodiment, IGRT system 104 comprises a high-energy radiation treatment (MeV) source 108 that selectively applies high-energy x-ray treatment radiation to a target volume of a patient P positioned on a patient support or treatment couch TC. The MeV source 108 applies the treatment radiation under the control of system controller 114, and in one embodiment, more particularly a treatment radiation control subsystem 128. System controller 114 further comprises processing circuitry 120, a detector controller 122, a couch position controller 124, and a keV radiation controller 126, each programmed and configured to achieve one or more of the functionalities described further herein. One or more imaging (keV) radiation sources 110 selectively emit relatively low-energy x-ray imaging radiation under the control of keV radiation controller 126, the imaging radiation being captured by one or more detectors 112. One or more of the detectors 112 can capture high-energy x-ray treatment radiation from MeV source 108 that has propagated through the target volume.

Each keV radiation source 110 and the MeV radiation source 108 have a precisely measurable and/or precisely determinable geometry relative to the (x, y, z) coordinate system of the IGRT system 104 and/or treatment room since they are dynamically moveable.

A couch positioner 130 can be actuated by the couch position controller 124 to position the couch TC. In some embodiments, a non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. IGRT system 104 further includes an operator workstation 116 and a treatment planning system 118.

In common clinical practice, treatment planning is performed on a pre-acquired treatment planning image or prior image data 106 generated by the reference imaging system 102. The pre-acquired treatment planning image 106 is often a high resolution three-dimensional CT image acquired substantially in advance (e.g., one to two days in advance) of the one or more radiation treatment fractions that the patient will undergo. As indicated in FIG. 3 by the illustration of an (i, j, k) coordinate system for the pre-acquired treatment planning image 106, which is in contrast to the (x, y, z) treatment room coordinate system illustrated for the treatment room of the IGRT system 104, there is generally no pre-existing or intrinsic alignment or registration between the treatment planning image 106 coordinate system and the treatment room coordinate system. During the treatment planning process, a physician typically establishes a coordinate system (e.g., i, j, k in treatment planning image 106) within the treatment planning image, which may also be referred to herein as the planning image coordinate system or planning image reference frame. A radiation treatment plan is developed in the planning image coordinate system that dictates the various orientations, sizes, durations, etc., of the high-energy treatment radiation beams to be applied by the MeV source 108 during each treatment fraction. Accurate delivery of therapeutic radiation to a target requires aligning the planning image coordinate system with the treatment room coordinate system, as the entire delivery and tracking system (if present) is calibrated to the treatment room coordinate system. It will be appreciated that this alignment does not need to be exact and further appreciated that couch adjustment or beam delivery adjustment can be used to account for offsets in the alignment between the two coordinate systems.

In one embodiment, immediately prior to each treatment fraction, under image guidance via the keV imaging radiation source(s) 110, including according to one or more of the embodiments described further herein below, image-based pre-delivery steps may be performed. For example, the patient can be physically positioned or aligned such that the planning image coordinate system (defined, for example and not by way of limitation, by a physician while creating a treatment plan on a CT image or planning image) is positioned into an initial alignment with the treatment room coordinate system, hereinafter termed an initial treatment alignment or initial treatment position. This alignment is commonly referred to as patient set up or patient alignment. Depending on the location of the target volume, the target volume can vary in position and orientation and/or can undergo volumetric deformations due to patient movement and/or physiological cycles such as respiration. As used herein, the term in-treatment alignment variation or in-treatment position variation is used to refer to the variations in position, orientation, and/or volumetric shape by which the current state of the target volume differs from the initial treatment alignment. By virtue of a known relationship between the treatment planning coordinate system and the treatment room coordinate system, the term in-treatment alignment variation can also be used to refer to the variations in position, orientation, or volumetric shape by which the current state of the target volume differs from that in the treatment planning coordinate system. More generally, the term initial treatment alignment or initial treatment position refers herein to the particular physical pose or disposition (including position, orientation and volumetric shape) of the body part of the patient upon patient setup at the outset of the treatment fraction.

A non x-ray based position sensing system 134 may also be provided. This non x-ray based position sensing system 134 may include, for example, external markers affixed in some manner to a patient's chest which move in response to respiration, which can precisely determine target location. Other mechanisms for monitoring respiration may also be used. Other non-respiratory position sensing systems 134 may also be used, including, for example, quasi static positioning, EKG for cardiac gating, etc. System 134 can correlate motion of the external markers with target motion, as determined from, for example, mono or stereoscopic x-ray projections. Non x-ray based position sensing system 134, therefore, can permit system controller 114 to monitor external marker motion, use the correlation model to precisely predict where the target will be located in real time (e.g., ~60 Hz), and direct the treatment beam to the target. As treatment of the moving target progresses, additional x-ray images may be obtained and used to verify and update the correlation model.

As used herein, "registration" of medical images refers to the determination of a mathematical relationship between corresponding anatomical or other (e.g. fiducial) features appearing in those medical images. Registration can include, but is not limited to, the determination of one or more spatial transformations that, when applied to one or both of the medical images, would cause an overlay of the corresponding anatomical features. The spatial transformations can include rigid-body transformations and/or deformable transformations and can, if the medical images are from different coordinate systems or reference frames, account for differences in those coordinate systems or reference frames. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Registration of images may be implemented between the reference imaging system 102 and the IGRT delivery system 104 and/or between the data and/or images derived from the various modalities of the multimodal IGRT delivery system 104, including the low energy source(s) 110 and the high energy source 108 (and their associated detectors 112). In particular, referring back to apparatus 10, registration may be implemented between data and/or images derived from radiation sources 20, 30 and detectors 24, 34.

Dual-source system (e.g., keV-MeV) imaging, including in the context of IGRT, can address and solve several problems and limitations of typical imaging systems used in these environments. Generally, combining a data acquisition from a keV subsystem and a data acquisition from a MeV subsystem can yield various improvements. For example, in some embodiments keV projection data can be used to complete MeV projection data and vice versa. In other embodiments, MeV projection data can be used for ROI keV imaging. In yet other embodiments, data from both modalities can be used to complement each other. The methods can be significant for obese patient scans, ROI imaging, etc., for improved image quality (e.g., reduced x-ray scatter and thus enhanced contrast of soft tissues).

In one embodiment, for example, projection data corresponding to a targeted ROI acquired using a primary imaging system can be combined with additional projection data acquired using a secondary imaging system that correspond to regions outside of the scan FOV of the primary imaging system. In one embodiment, projection data from the secondary imaging system can then be used to estimate the missing or incomplete data outside the scan FOV of the primary imaging system, which is necessary for image reconstruction. For example, for an obese patient scan, an MeV subsystem can be used to acquire the central region of the patient (which is laterally truncated) and a keV subsystem can be used to acquire the peripheral region of the patient. The keV projection data can then be used to help estimate the missing MeV projection data for improved quality of image reconstruction.

Several other exemplary embodiments will be discussed in detail below. Each of these embodiments may use one or more exemplary scan configurations.

Figure 4:
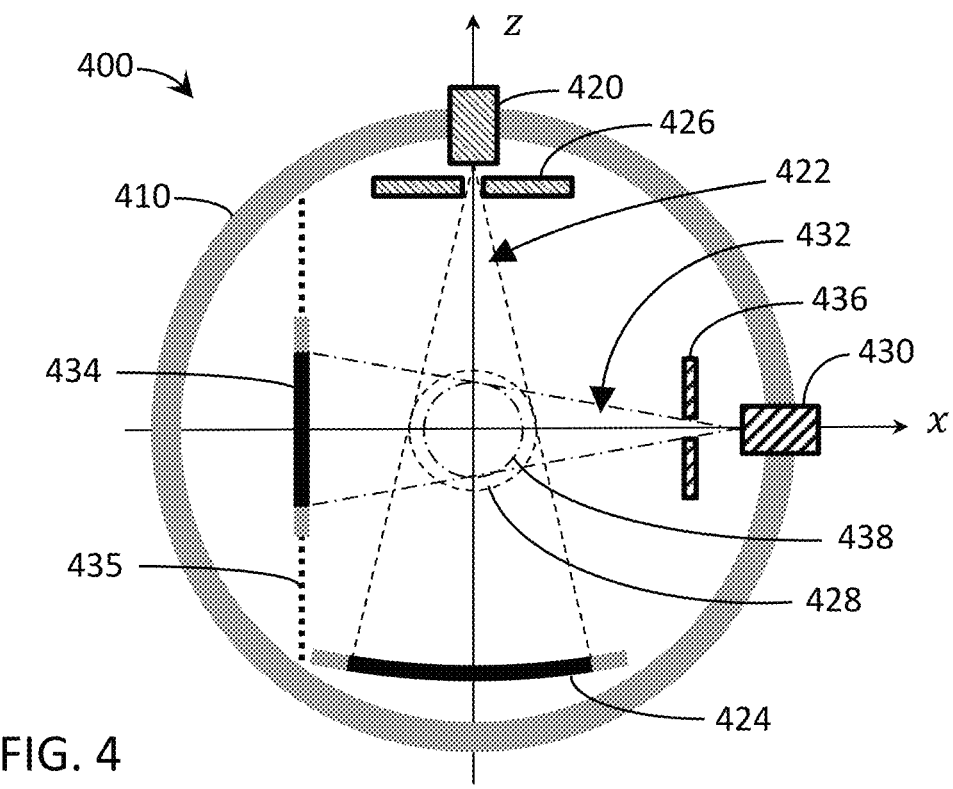
FIG. 4 shows an illustration of an exemplary multimodal scan configuration.

In one embodiment, FIG. 4 shows an illustration of an exemplary multimodal scan configuration 400. Looking into the front of the ring gantry 410, FIG. 4 shows a high energy radiation source 420 (e.g., MeV) and a low energy radiation source 430 (e.g., keV) mounted to the ring gantry 410. Radiation sources 420, 430 are shown mounted orthogonal to each other, but other embodiments can include other angular relationships and additional radiation sources and/or detectors. High energy radiation source 420 is shown projecting radiation through a collimator or beamformer 426 to create radiation beam 422 projecting onto a portion of detector 424. In this configuration, high energy radiation source 420 has transaxial FOV 428. Low energy radiation source 430 is shown projecting radiation through a beamformer 436 to create radiation beam 432 projecting onto a portion of detector 434. In this configuration, low energy radiation source 430 has transaxial FOV 438. Detector 434 is shown centered within its range 435. In this manner, the radiation sources 420, 430 will project radiation through an overlapping transaxial FOV. In this embodiment, the multimodal scan configuration 400 shows the high energy FOV 428 with a larger transaxial FOV than the low energy FOV 438.

Figure 5:
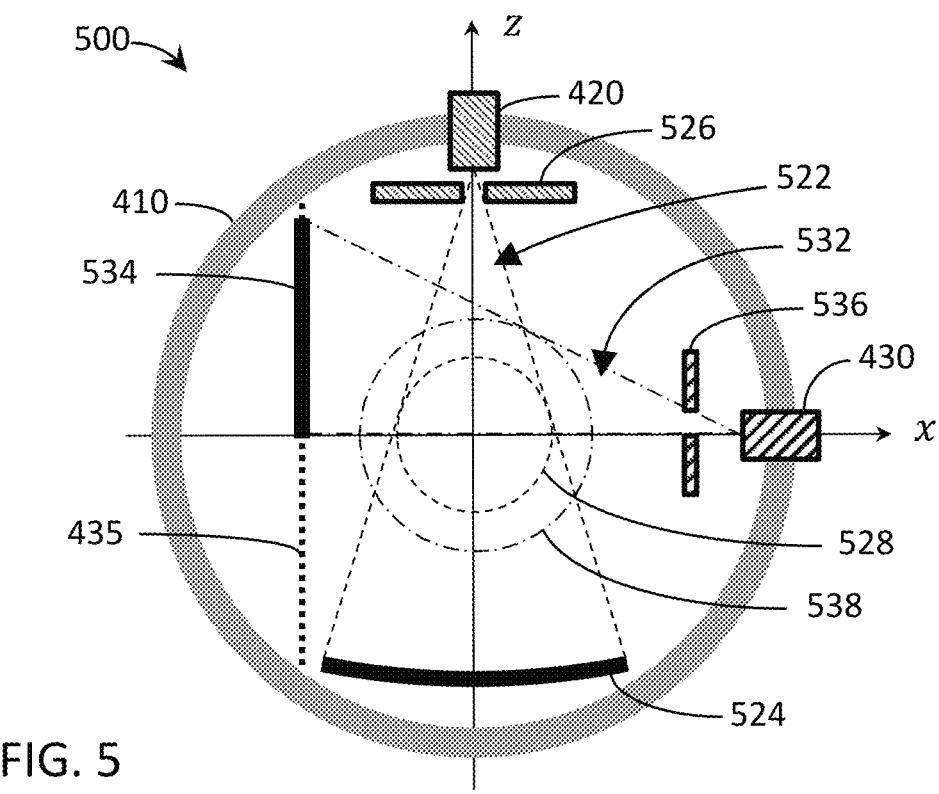
FIG. 5 shows an illustration of another exemplary multimodal scan configuration.

In another embodiment, FIG. 5 shows an illustration of another exemplary multimodal scan configuration 500. Looking into the front of the ring gantry 410, FIG. 5 also shows the high energy radiation source 420 and the low energy radiation source 430 mounted orthogonally to the ring gantry 410. High energy radiation source 420 is shown projecting radiation through a beamformer 526 to create radiation beam 522 projecting onto detector 524. In this configuration, high energy radiation source 420 has transaxial FOV 528. Low energy radiation source 430 is shown projecting radiation through a beamformer 536 to create radiation beam 532 projecting onto offset detector 534. In this configuration, low energy radiation source 430 has transaxial FOV 538 with at least 180 degrees of rotation. In this manner, the radiation sources 420, 430 will also project radiation through an overlapping transaxial FOV. In this embodiment, the multimodal scan configuration 500 shows the low energy FOV 538 with a larger transaxial FOV than the high energy FOV 528.

In these and other embodiments, multimodal systems can consist of two or more sub-imaging systems, for example, MeV (e.g., MeVCT) and keV (e.g., keVCT). The MeV imaging system consists of a MeV radiation source (e.g., 420) and a MeV radiation detector (e.g., 424) and the keV imaging system consists of a keV radiation source (e.g., 430) and a keV radiation detector (e.g., 434). Respective beamformers (e.g., 426 and/or 436) may also be included in the subsystems. The MeV and keV imaging systems are not necessarily co-planar. For example, a small longitudinal distance between the two subsystems may be allowed. The keV system can be about 90 degrees apart from the MeV system.

In some embodiments, the MeV detector can be fixed, resulting in a fixed scan FOV, whereas the keV detector is translatable along a line in the gantry plane such that the corresponding scan FOV of the keV imaging system is flexible, as shown above in FIGS. 4-5. Such a flexible scan FOV can be implemented with an actuatable beamformer to avoid unnecessary x-ray dose to the patient. The systems may also include other pre- and post-patient filters.

Various factors, including, for example, beamformer configurations, radiation source angles, detector positions, etc. may be used to control the respective FOVs (e.g., transaxial and axial) of the radiation sources. In some embodiments, the radiation sources 420, 430 may be physically offset in the longitudinal direction (along the y-axis) and may scan the patient at different times (temporally offset).

Figure 6:
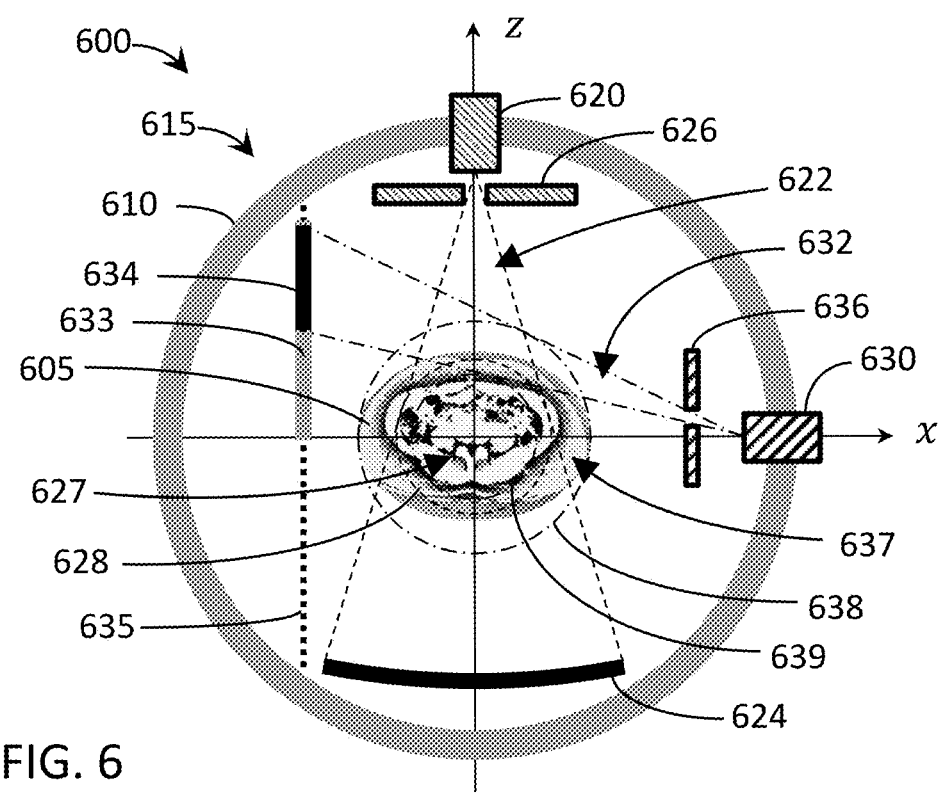
FIG. 6 shows an illustration of an exemplary multimodal scan configuration projecting through an exemplary large patient in a transaxial plane.

In one embodiment, FIG. 6 shows an illustration of an exemplary multimodal scan configuration 600 projecting through an exemplary large patient 605 in a transaxial plane 615. This embodiment may be applicable to imaging large patients that extend beyond a MeV system transaxial FOV and/or to reduce the x-ray dose to the patient. Looking into the front of the ring gantry 610, FIG. 6 shows a MeV radiation source 620 and a keV radiation source 630 mounted orthogonally to the ring gantry 610.

The MeV radiation source 620 is shown projecting radiation through a beamformer 626 to create radiation beam 622 projecting onto detector 624. In this configuration, the MeV radiation source 620 has a transaxial FOV within central region 627 bounded by 628.

The keV radiation source 630 is shown projecting radiation through a beamformer 636 to create radiation beam 632 projecting onto offset detector 634. Flat panel detector 634 is shown offset within its range 635 and with unexposed area 633 (due to beamformer 636). In this configuration, the keV radiation source 630 has a transaxial FOV in a peripheral region 637 bounded by 638 and 639 with at least 180 degrees of rotation.

In this manner, the radiation sources 620, 630 will project radiation through an adjacent or overlapping transaxial FOV (i.e., where the central region 627 and the peripheral region 637 overlap). In some embodiments, a bowtie filter (not shown) may be utilized to enable a larger dynamic range of the detector 634.

Figure 7:
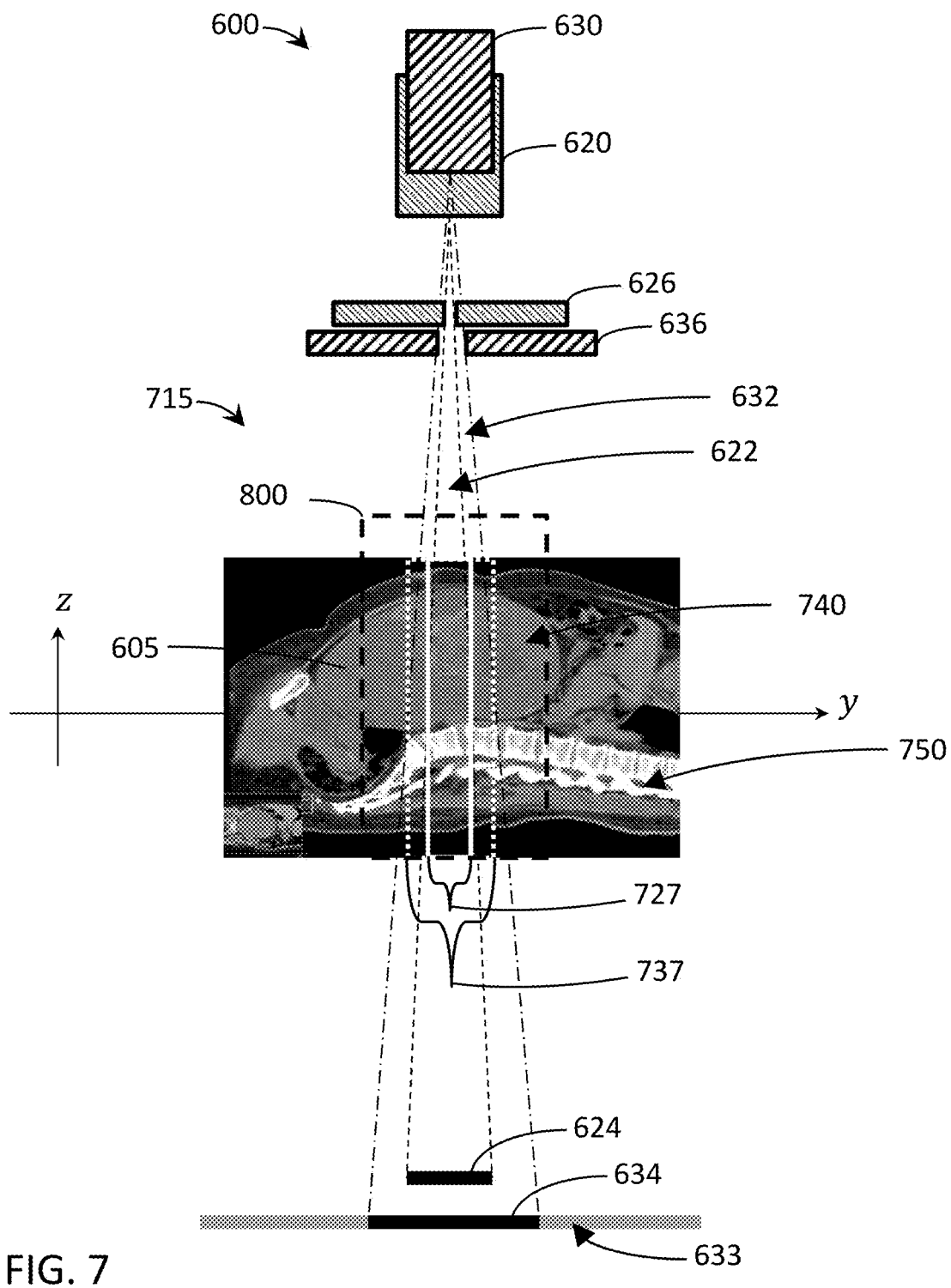
FIG. 7 shows another illustration of the exemplary multimodal scan configuration shown in FIG. 6 projecting through the exemplary large patient in an axial plane with a superimposed view of the radiation systems.

FIG. 7 shows another illustration of the exemplary multimodal scan configuration 600 projecting through the exemplary large patient 605 in an axial (longitudinal) plane 715 with a superimposed view of the radiation systems. Looking into the side of the ring gantry (not shown), FIG. 7 shows the position of the MeV radiation source 620 and the keV radiation source 630 rotated and superimposed in the same axial plane 715. Radiation sources 620, 630 are not necessarily mounted in the same plane and are not typically mounted against each other (e.g., they may be mounted to the gantry system 90 degrees apart), but are shown superimposed in FIG. 7 to show an exemplary overlap of their respective views and features. Other embodiments can include other angular relationships and additional radiation sources and/or detectors.

The MeV radiation source 620 is shown projecting radiation through beamformer 626 to create radiation beam 622 projecting onto detector 624. In this configuration, the MeV radiation source 620 has axial FOV 727. The keV radiation source 630 is shown projecting radiation through beamformer 636 to create radiation beam 632 projecting onto a portion of detector 634. In this configuration, the keV radiation source 630 has axial FOV 737. Detector 634 is shown with shadowed region 633, which is blocked from direct radiation by beamformer 636. Detectors may have shadowed regions in axial and/or transaxial directions. In this manner, the radiation sources 620, 630 will project radiation through an overlapping axial FOV.

Figure 8:
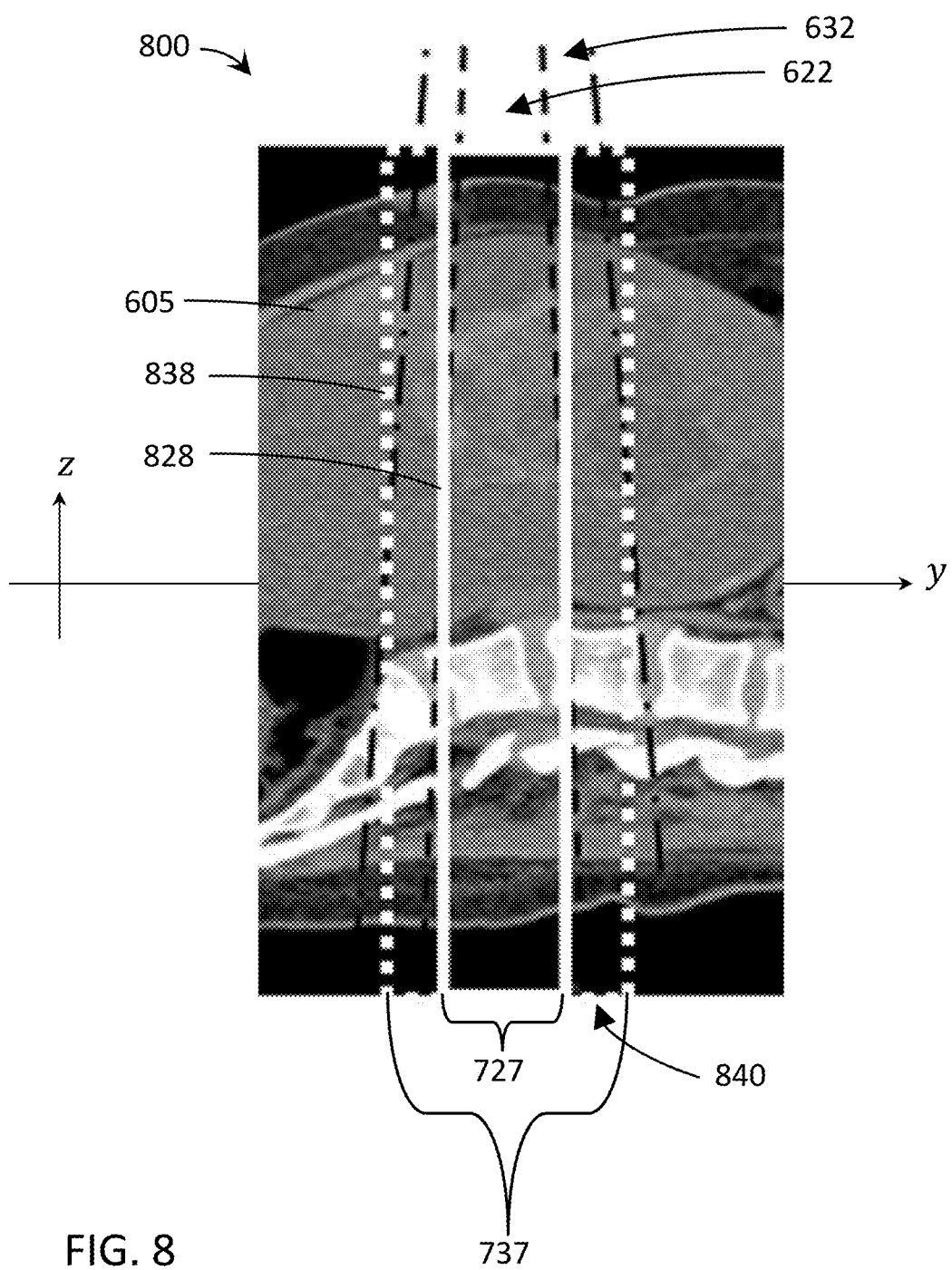
FIG. 8 shows an illustration of a zoomed-in portion of the target shown in FIG. 7.

FIG. 8 shows a zoomed-in portion 800 of the axial plane 715 shown in FIG. 7. Radiation beams 622, 632 are shown passing through patient 605. The MeV system axial FOV region 727 is bounded by 828 and the keV system axial FOV region 737 is bounded by 838, providing overlapping imaging data. Here, the keV system axial FOV 737 provides imaging data beyond the MeV system axial FOV 727, shown as region 840.

As mentioned above, this configuration can be designed for large field-of-view (LFOV) MeV imaging, including for imaging large or obese patients. It can use both MeV and keV subsystems of a multimodal system. In one embodiment, as shown in the transaxial plane 615 of FIG. 6, the MeV system is used to acquire projection data corresponding to the central region 627 of the scanned patient 605. The MeV projection data are truncated due to the large size of the patient 605 and limited transaxial FOV 628 of the MeV detector 624. The keV system is used to acquire projection data corresponding to the peripheral region 637 of the scanned patient 605. The keV projection data are also truncated inside of boundary 639, which is within the central region 627 boundary 628. It is required that there is overlap between the keV and MeV projection data at the same angular position (which may correspond to different timings). The design of the two subsystems is also shown in the axial (longitudinal) direction in FIGS. 7-8.

Multimodal imaging can be used to analyze the image in FIG. 7. For example, image aberrations (not shown) may occur where the keV beam traverses softer tissue (740) in the vicinity of bone 750. In particular, separate MeV and KeV image data may be acquired simultaneously or in sequence. The MeV image will have greater contrast when imaging dense tissue like bone 750. A composite image using both MeV and keV detection data can be generated. Such a composite image may, for example, use the MeV portion to provide contrast for the portions of the image including bone 750. Portions of the image including soft tissue (e.g., tissue 740) may be contributed by the keV detector signal. The latter will have far greater contrast in soft tissue regions. Determining the relative locations of soft tissue 740 and bone 750 in the image can be done automatically, for example, via a spectral analysis of photons contributing to each. As discussed in more detail below, the spectral analysis can be used to determine the materials composition of the bone region 750, in particular. This can be accomplished via all of the ways disclosed here (e.g., via using energy binning to compare the relative proportions of photoelectric effect, Compton scattering, and/or pair production range photons).

The following flow charts and block diagrams illustrate exemplary configurations and methodologies associated with the multimodal radiation systems described above. The exemplary methodologies may be carried out in logic, software, hardware, or combinations thereof. In addition, although the procedures and methods are presented in an order, the blocks may be performed in different orders, including series and/or parallel. Further, additional steps or fewer steps may be used.

Figure 9:
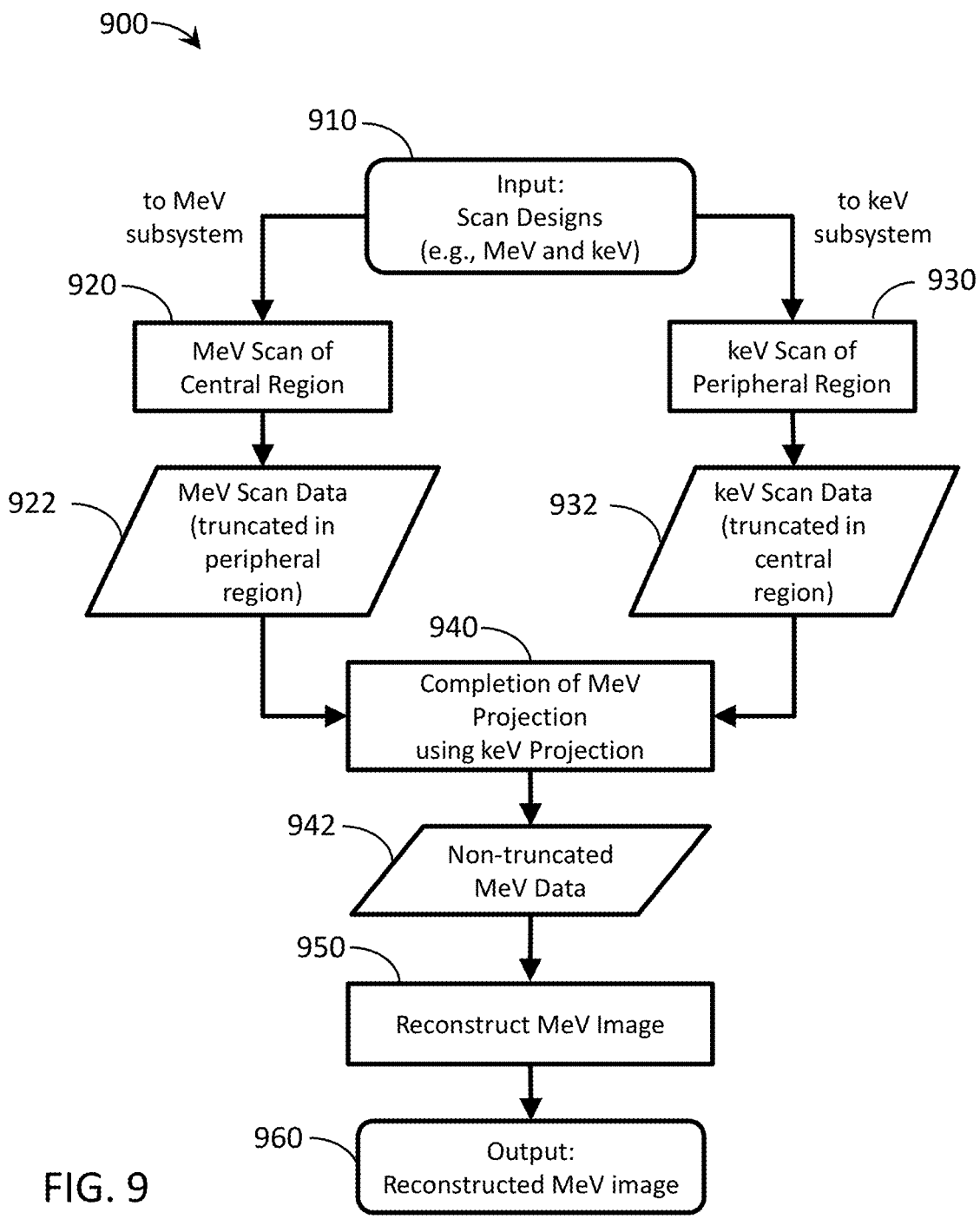
FIG. 9 is a flow chart depicting an exemplary method of combining scan data from multiple radiation modalities to approximate missing MeV projection data using keV projection data.

FIG. 9 is a flow chart depicting an exemplary method 900 of combining scan data from multiple radiation modalities, such as those described above, to approximate missing MeV projection data in a peripheral region using keV projection data. At step 910, the method 900 determines a scan configuration, including scan designs for each modality of the multimodal system. A MeV scan of a central region is executed at step 920. A keV scan of a peripheral region is executed at step 930. As described above, the respective scans produce MeV scan data 922 (truncated in the peripheral region) and keV scan data 932 (truncated in the central region). Next, at step 940, the method 900 makes use of or combines the keV scan data 932 to complete the MeV scan data 922 to form a complete MeV projection or non-truncated MeV data 942. Then, at step 950, the method 900 processes the non-truncated MeV data 942, for example, to reconstruct a MeV image. At step 960, the reconstructed MeV image can be output.

Image reconstruction 950 may include spectral analysis of the collected data via any of the methods and algorithms described above. For example, spectral analysis and binning (e.g., according to the energy bins for spectra 62 and 64 shown in FIG. 2C and/or the histograms 66 and 68 in FIG. 2D) may be used in materials analysis and identification. One such technique is to use binning to isolate lower energy photoelectric range x-ray photons to examine the atomic number (Z) dependence. As discussed above in the context of FIG. 7, this can help distinguish bone 750 from softer tissue 740 for further image analysis. Once these areas are differentiated, the same or similar spectral analysis can select certain areas of the image (e.g., bone 750) such that they are contributed, in an MeV/keV composite image, from an optimal or better x-ray energy range (e.g., the MeV). Similar analysis can be performed to optimize the source for soft tissue 740 areas of the image. In addition, spectral information may be used to correct other defects or features. For example, iodinated contrast may be removed using spectral information. It may also include differential image sourcing, as discussed in the context of FIG. 8 (e.g., using spectral information to associate portions of an image with a certain type of tissue, then use an appropriate energy range of x-ray photons for that portion in order to improve image qualities such as contrast).

Other techniques include using spectral analysis to differentiate between x-ray photon contributions from the photoelectric effect, Compton scattering, and/or pair production. Since each effect, as described above, has a different Z dependence, their relative abundance in detected signals can yield materials-specific information. The different photoelectric, Compton scattering, and pair production contributions can be determined by comparing the energy dependence of these signals, as described above.

In another embodiment, FIG. 10 shows an illustration of an exemplary multimodal scan configuration 1000 projecting through an exemplary patient 1005 in a transaxial plane 1015. This embodiment may be applicable to imaging to reduce the x-ray dose to the patient, reduce x-ray scatter, and/or improve keV image quality, especially, for example, in terms of soft tissue visibility. Looking into the front of the ring gantry 1010, FIG. 10 shows a MeV radiation source 1020 and a keV radiation source 1030 mounted orthogonally to the ring gantry 1010.

The MeV radiation source 1020 is shown projecting radiation through a beamformer 1026 to create radiation beam 1022 projecting onto detector 1024. Detector 1024 is shown with shadowed region 1023, which is blocked from direct radiation by beamformer 1026. In this configuration, the MeV radiation source 1020 has a transaxial FOV within intermediate region 1027 bounded by 1028 and 1029. FIG. 11 shows an illustration of the MeV subsystem 1100 of exemplary multimodal scan configuration 1000.

The keV radiation source 1030 is shown projecting radiation through a beamformer 1036 with two apertures to create radiation beam(s) 1032 projecting onto offset detector portions 1034 and 1044. The flat panel detector is shown offset within its range 1035 and with unexposed area 1033 (due to beamformer 1036). In this configuration, the keV radiation source 1030 has a transaxial FOV in a peripheral region 1037 bounded by 1038 and 1039 with at least 180 degrees of rotation relative to the point of interest and in a central region 1047 bounded by 1048. In some embodiments, the central region 1047 may include a target region of the patient. FIG. 12 shows an illustration of the keV subsystem 1200 of exemplary multimodal scan configuration 1000. While this embodiment includes both the keV central region 1047 and the keV peripheral region, other embodiments need not include both. For example, another embodiment includes only the central region 1047 (with one keV aperture).

In this manner, the radiation sources 1020, 1030 will project radiation through an adjacent or overlapping transaxial FOV (i.e., where the MeV intermediate region 1027 overlaps with the keV peripheral region 1037 and the keV central region 1047). FIG. 13 shows an illustration of the MeV FOV intermediate region 1027 and the keV FOV peripheral region 1037 and central region 1047 created by the multimodal scan configuration 1000 in a superimposed view 1300. In particular, the MeV FOV intermediate region 1027 and the keV FOV central region 1047 overlap at region 1310 (shaded) and the MeV FOV intermediate region 1027 and the keV FOV peripheral region 1037 overlap at region 1312 (shaded).

As mentioned above, this configuration can be designed for keV region-of-interest (ROI) imaging, including to reduce the x-ray dose, reduce x-ray scatter, and/or improve keV image quality. In other embodiments, a similar configuration can be used for MeV ROI imaging. It can use both MeV and keV subsystems of a multimodal system. In one embodiment, as shown in the transaxial plane 1015 of FIGS. 10 and 12, the keV subsystem 1200 provides two scan FOVs 1037, 1047. The central region 1047 is located at the center and the peripheral region 1037 is a donut shape located at the periphery. The central region 1047 can be the target ROI for the patient, whereas the peripheral region 1037 can be for auxiliary purposes. The two scan FOVs 1037, 1047 are disconnected and thus are missing projection data between the two scan FOVs 1037, 1047 that are needed for exact image reconstruction. In one embodiment, an estimate of those missing keV data can be based on the available keV projection data via, e.g., interpolation. The keV projection data of the peripheral region 1037 is important for this estimation of missing data because it will provide the range information of the patient. However, as mentioned above, in one more simplified ROI embodiment, the peripheral region 1037 is not used.

In this embodiment, the keV beamformer 1036 portion corresponding to the peripheral scan FOV 1037 may be adaptive to the patient shape to save dose (and may involve usage of prior CT data). The MeV projection data may or may not be needed, depending on the application. In one embodiment, as shown in the transaxial plane 1015 of FIGS. 10 and 11, the MeV subsystem 1100 can provide projection data in a scan FOV 1027 that can compensate or complement the keV scan FOVs 1037, 1047, such that it will provide information for better keV data completion. Note that a bowtie filter may be involved to enable larger dynamic range of the flat panel detector.

Figure 14:
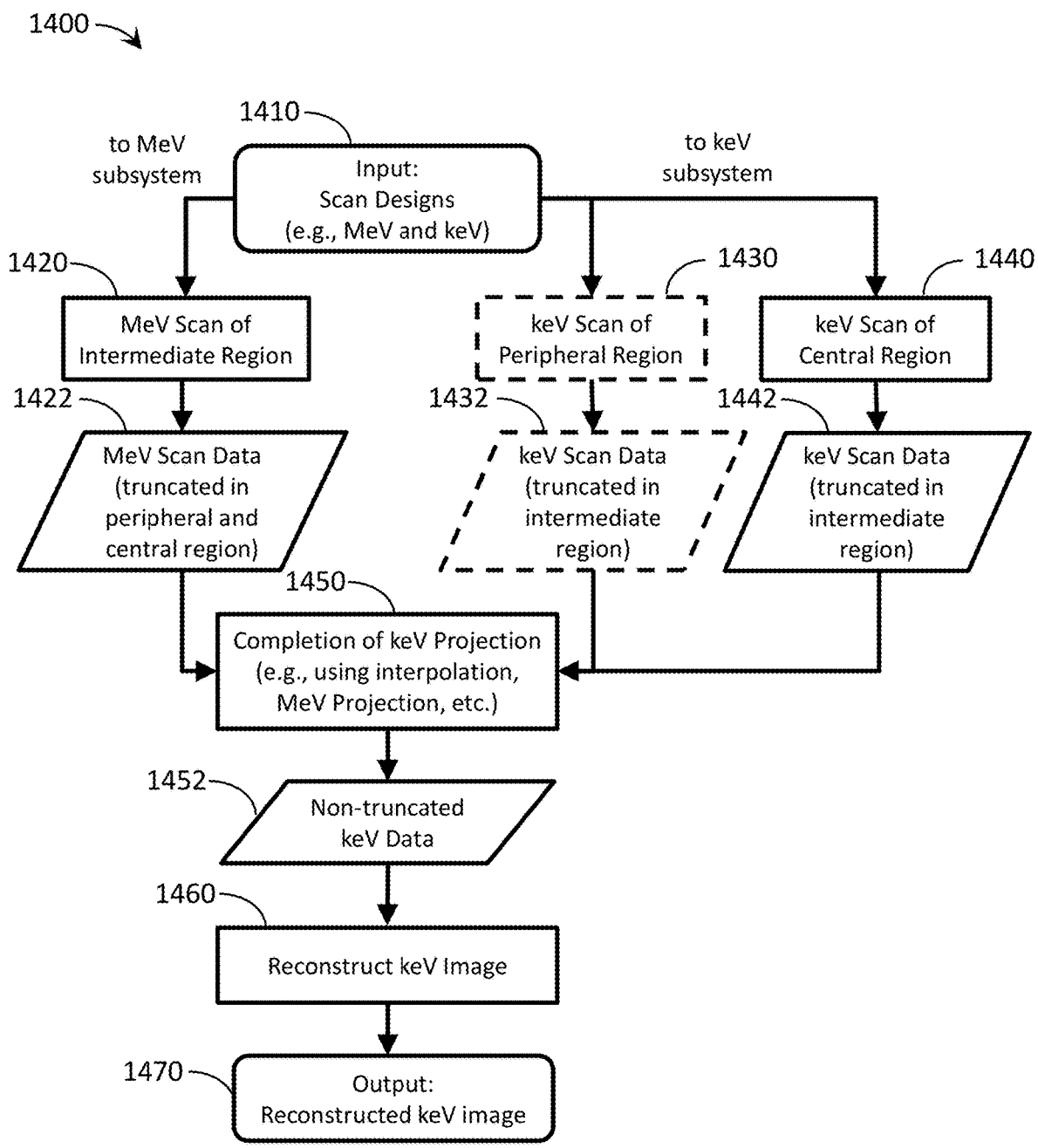
FIG. 14 is a flow chart depicting an exemplary method of combining scan data from multiple radiation modalities to approximate missing keV projection data using MeV projection data.

FIG. 14 is a flow chart depicting an exemplary method 1400 of combining scan data from multiple radiation modalities, such as those described above, to approximate missing keV projection data in an intermediate region using MeV projection data. At step 1410, the method 1400 determines a scan configuration, including scan designs for each modality of the multimodal system. A MeV scan of an intermediate region is executed at step 1420. A keV scan of a peripheral region is executed at step 1430 (if embodiment with peripheral region included). A keV scan of a central region is executed at step 1440. As described above, the respective scans produce MeV intermediate scan data 1422 (truncated in the peripheral and central region), keV peripheral scan data 1432 (truncated in the intermediate region), and keV central scan data 1442 (truncated in the intermediate region). keV projection data is missing between the keV peripheral and central regions. Next, at step 1450, the method 1500 makes use of or combines the MeV scan data 1422 to complete the keV scan data 1432, 1442 to form a complete keV projection or non-truncated keV data 1452. Step 1450 may also include interpolation of the keV scan data 1432, 1442 (e.g., optimized with the MeV scan data 1422), prior CT data (pCT) if available, etc., in addition to or instead of the use of the MeV scan data 1422. Registration, rebinning, and/or other processes (e.g., attenuation constant normalization, scatter correction, scaling, etc.) may also be involved with step 1450. In embodiments without the keV peripheral scan 1430, keV data 1432 is not available and is not used. Then, at step 1460, the method 1400 processes the non-truncated keV data 1452, for example, to reconstruct a keV image. At step 1470, the reconstructed keV image can be output.

In an embodiment where MeV scan data 1422 (e.g., via step 1420) and/or pCT data are available, use of those data can be made to improve the estimation of the missing keV data at step 1450. Usage of the estimated data can be mainly for the global filtration operators involved in the reconstruction. In some embodiments, it may be recommended to only perform image reconstruction in the ROI region.

As mentioned above, in some embodiments, the beamformer 1036 portion corresponding to the keV peripheral scan FOV 1037 can be adaptive to follow the patient shape to further reduce patient dose. The rough patient shape can be estimated, for example, by pCT, scout views, adaptive feedback from projections, etc. In some embodiments, the beamformer 1036 portion corresponding to the central scan FOV 1047 can be adaptive to a non-central ROI to provide flexibility of ROI selection. Other embodiments may employ a combination of both adaptive techniques.

The MeV subsystem 1100 can be used to provide a scatter- and/or dose-reduced scan 1420 with a scan FOV 1027 that is located between the keV peripheral and central scan FOVs 1037, 1047, to provide more accurate estimation of the missing keV projection data. This process (e.g., at step 1450) may involve registration, rebinning, and/or mapping between the MeV and keV data. Available pCT data can be used to improve the estimation accuracy of the missing keV projection data. This process (e.g., at step 1450) may involve registration, rebinning, and/or mapping between the pCT and the keV data.

As discussed above in the context of element 950 in FIG. 9, image reconstruction 1460 may include spectral analysis of the collected data via any of the methods and algorithms described above. This includes binning and/or creating a histogram according to the energy bins for spectra 62 and 64 shown in FIG. 2C and/or the histograms 66 and 68 in FIG. 2D. As discussed above, these techniques may be used in materials analysis and identification (e.g., by isolating photoelectric range x-ray photons to examine the atomic number (Z) dependence). Among other things, this can select certain areas (e.g., soft tissue or bone) of the image for contributions from certain energies in the x-ray spectra in order to optimize presentation of the composite image. Spectral analysis can also differentiate between x-ray photon contributions from the photoelectric effect, Compton scattering, and/or pair production. The relative dependence on Z and energy can facilitate materials characterization and image optimization according to any of the analytical techniques described, referenced, or implied herein.

Figure 15:
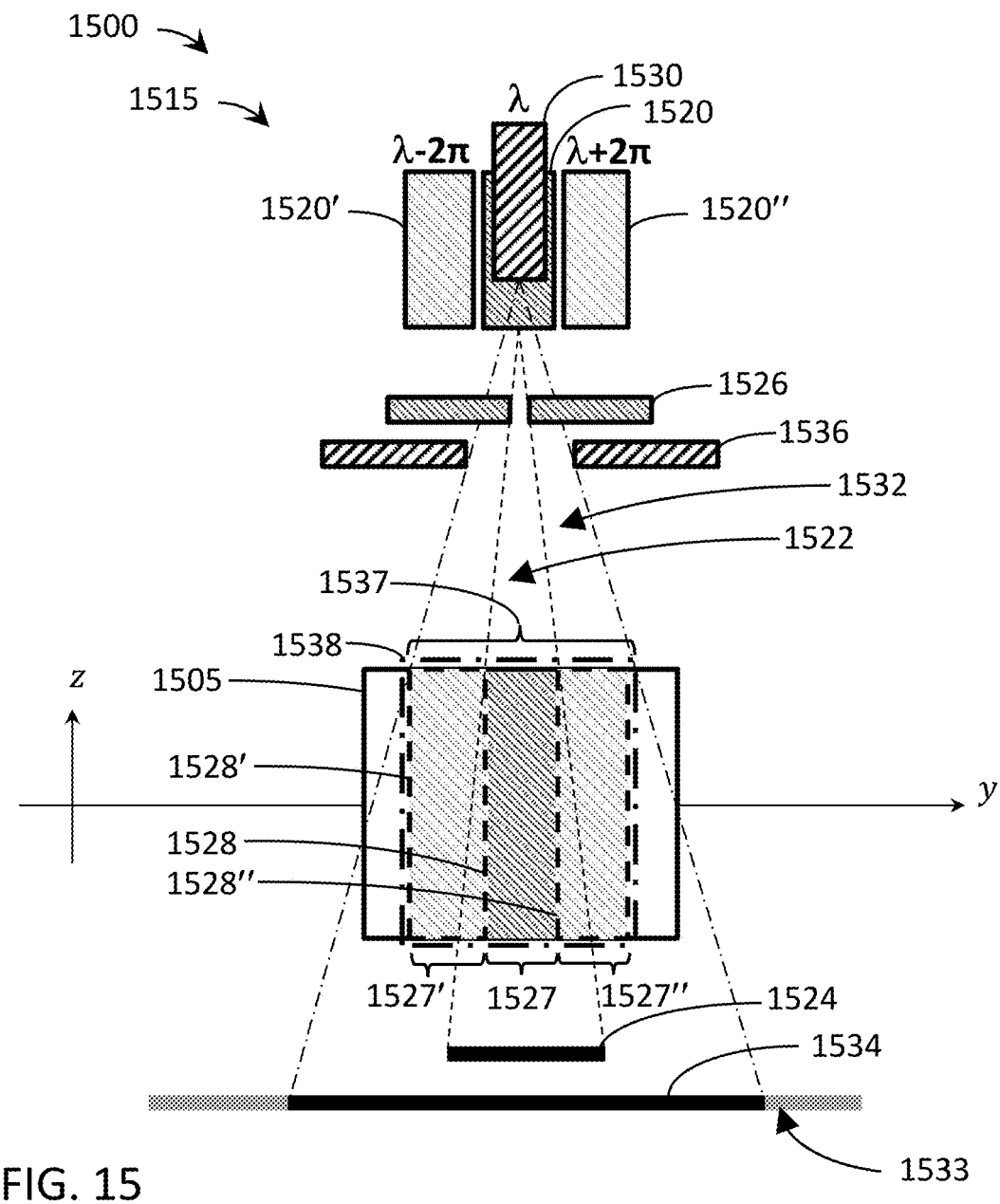
FIG. 15 shows an illustration of an exemplary multimodal scan configuration projecting through an exemplary patient in an axial plane with a superimposed view of the radiation systems.

In another embodiment, FIG. 15 shows an illustration of an exemplary multimodal scan configuration 1500 projecting through an exemplary patient 1505 in an axial (longitudinal) plane 1515 with a superimposed view of the radiation systems. This embodiment may be applicable for scalable FOV (SFOV) dual-energy imaging, which provides a variety of options, including, for example, SFOV configurations for IGRT. This embodiment is an example of both scalable transaxial FOV and scalable axial FOV. Generally, a wider keV axial FOV can allow for better modeling of the MeV projections over finite cell dimensions. This may be important for a wide single-row MeV detector, improving slice thickness of the multimodal image. Looking into the side of the ring gantry (not shown), FIG. 15 shows the position of the MeV radiation source 1520 and the keV radiation source 1530 rotated and superimposed in the same axial plane 1515. Radiation sources 1520, 1530 are not necessarily mounted in the same plane and are not typically mounted against each other (e.g., they may be mounted to the gantry 90 degrees apart), but are shown superimposed in FIG. 15 to show an exemplary overlap of their respective views and features. Other embodiments can include other angular relationships and additional radiation sources and/or detectors.

The MeV radiation source 1520 is shown projecting radiation through beamformer 1526 to create radiation beam 1522 projecting onto detector 1524. In this configuration, the MeV radiation source 1520 has axial FOV 1527 bounded by 1528 at an angular position λ. During a prior rotation, the MeV radiation source, designated as 1520', has a neighboring axial FOV 1527' bounded by 1528' at an angular position λ−2π radians (a difference of one complete revolution). During a subsequent rotation, the MeV radiation source, designated as 1520", has a neighboring axial FOV 1527" bounded by 1528" at an angular position λ+2π radians. Prime notation (') is used to indicate that a component of the system has moved or changed in comparison to its non-prime or other prime form or position. For example, "1520," "1520'," and "1520"," all refer to the MeV radiation source 1520, but at different angular positions.

The keV radiation source 1530 is shown projecting radiation through beamformer 1536 to create radiation beam 1532 projecting onto a portion of detector 1534. In this configuration, the keV radiation source 1530 has axial FOV 1537 bounded by 1538. Detector 1534 is shown with shadowed region 1533, which is blocked from direct radiation by beamformer 1536. Detectors may have shadowed regions in axial and/or transaxial directions.

In this manner, the radiation sources 1520, 1530 will project radiation through an overlapping axial FOV (e.g., axial MeV FOVs 1527'+1527+1527"=axial keV FOV 1537). In this embodiment, MeV radiation source 1520 requires three revolutions whereas the keV radiation source requires one revolution to accumulate the same axial FOV width. As mentioned above, the superimposed view of the radiation sources 1520, 1530 in FIG. 15 is only for illustration purposes. The keV and MeV subsystems can arrive at the illustrated angular position at different timings. Also, at this angular position, they may have different longitudinal positions. The keV subsystem provides a much larger longitudinal scan FOV 1537 than the MeV subsystem FOV 1527, which provides additional time for the keV subsystem to complete a larger in-plane (transaxial) scan FOV, for example, during multiple rotations, as discussed below.

FIGS. 16 and 17 show illustrations of the exemplary keV radiation source 1530 during the multimodal scan configuration 1500 projecting through the exemplary patient 1505 in a transaxial plane 1615 during different rotations.

Looking into the front of the ring gantry 1610, FIG. 16 shows keV radiation source 1530 mounted to the ring gantry 1610 during rotation A. The keV radiation source 1530 is shown projecting radiation through the beamformer 1536 to create radiation beam 1532 projecting onto offset detector 1534. Flat panel detector 1534 is shown offset within its range 1635 and with unexposed area 1533 (due to beamformer 1536). Detectors may have shadowed regions in axial and/or transaxial directions. In this configuration during rotation A, the keV radiation source 1530 has a transaxial FOV in a peripheral region 1537 bounded by 1538 and 1539 with at least 360 degrees of rotation.

FIG. 17 shows keV radiation source 1530 mounted to the ring gantry 1610 during rotation B. The keV radiation source 1530 is shown projecting radiation through the beamformer 1536' to create radiation beam 1532' projecting onto offset detector 1534'. Flat panel detector 1534' is shown centered within its range 1635 and with unexposed area 1533' (due to beamformer 1536'). In this configuration during rotation B, the keV radiation source 1530 has a transaxial FOV in a central region 1537' bounded by 1538'. The central region 1537' may correspond to a target ROI of the patient 1505. In embodiments where the target ROI is away from the isocenter, dynamic collimation of the beamformer 1536' will be required.

In this manner, radiation source 1530 will project radiation through adjacent or overlapping transaxial FOVs (i.e., where the peripheral region 1537 and the central region 1537' overlap). The peripheral keV scan FOV 1537 (donut shaped) corresponds to an off-centered detector position 1534, whereas the central keV scan FOV 1537' (disk shaped) corresponds to a centered detector position 1534'. The union of the two keV scan FOVs 1537, 1537' results in a complete and large keV scan FOV. In this embodiment, keV transaxial FOVs 1537, 1537', during rotations A and B, respectively, overlap at region 1810 as shown in the superimposed view 1800 of FIG. 18. In different embodiments, the keV radiation source 1530 can be on or off as the beamformer 1536 transitions between projecting to the peripheral region 1537 and the central region 1537' in the transaxial plane 1615 of the patient 1505.

The transaxial views 1615, 1615' shown in FIGS. 16 and 17, during rotations A and B, can coincide with the axial view 1515 at the various angular positions ($\lambda-2\pi$, $\lambda$, and $\lambda+2\pi$) shown in FIG. 15. FOVs have temporally coincident axial and transaxial characteristics that are shown separately in the different views of the figures. For example, the keV radiation source 1530 FOV 1537 encompasses the axial characteristics shown in FIG. 15 and the transaxial characteristics shown in FIGS. 16 and 17 at the same time, during various revolutions.

In this embodiment, the keV detector 1534 can be much larger than the MeV detector 1524 in the longitudinal direction (e.g., as shown in FIG. 15). By using a much larger longitudinal keV scan FOV 1537 than the MeV scan FOV 1527, the keV subsystem has more time to provide a larger in-plane (transaxial) scan FOV.

In some embodiments, a key design parameter can be how much larger should the illuminated keV detector 1534 be than the smaller MeV detector 1524. For example, let H be the MeV detector width at the iso-center. Let sH be the illuminated keV detector width at the iso-center, with s being a scalar larger than 1. In one embodiment, the criteria to determine the value of s is such that: at any rotation angle, any point that 1) is inside the target in-plane scan FOV; and 2) is visible by the MeV radiation source 1520, should be visible by the keV radiation source 1530 at any azimuth angle at least once. This requirement can be achieved by a combination of moving the keV detector 1534 and use of a dynamic beamformer 1536. In this embodiment, it is also important to make sure that the movement of the keV detector 1534 and the keV beamformer 1536 are both continuous.

FIGS. 15-18 demonstrate an exemplary embodiment that satisfies this requirement. In this embodiment, the axial (longitudinal) keV FOV 1537 is about 3 times larger than the axial MeV FOV 1527. At one rotation angle ($\lambda$), as shown in FIG. 15, the current MeV illuminated portion of the object (indicated by the boundary 1528) is visible at the same azimuth angle by the previous ($\lambda-2\pi$), current ($\lambda$), and next rotations ($\lambda+2\pi$), shown as 1528', 1528, and 1528", respectively. During these three rotations, one rotation (e.g., Rotation A as shown in FIG. 16) is dedicated to the peripheral keV scan with keV FOV 1537, and another rotation (e.g., Rotation B as shown in FIG. 17) is dedicated to the central keV scan with keV FOV 1537'. The (left) edge of one rotation can be used to make sure that the transition between the peripheral region 1537 and the central region 1537' is smooth. This configuration 1500 can be used to provide both MeV and keV projection data in the same ROI, enabling dual energy imaging for the ROI.

In this embodiment, the two keV scan FOVs 1537, 1537' shown in FIGS. 16-18 may not be acquired consecutively. A period of time can be required to translate the detector from one position to another. However, as mentioned above, since the keV subsystem provides a much larger axial FOV 1537 than the MeV subsystem FOV 1527, additional time is available for the keV subsystem to complete a larger transaxial scan FOV during the same time period required for the full axial MeV scan. For example, in one embodiment: step 1—first full rotation (rotation index 0→1.0), a first keV scan full rotation (e.g., Rotation B shown in FIG. 17 with the keV beamformer focusing on the central transaxial FOV) can coincide with a first MeV scan full rotation (e.g., $\lambda-2\pi$ rotation shown in FIG. 15); step 2—the next half rotation (rotation index 1.0→1.5), translating the keV beamformer and/or the keV detector to the peripheral transaxial region can coincide with a first half of a second MeV scan rotation (e.g., first half of $\lambda$ rotation shown in FIG. 15); step 3—the next full rotation (rotation index 1.5→2.5), a second keV scan full rotation (e.g., Rotation A shown in FIG. 16 with the keV beamformer focusing on the peripheral transaxial FOV) can coincide with a second half of the second MeV scan rotation (e.g., second half of $\lambda$ rotation shown in FIG. 15) and a first half of a third MeV scan rotation (e.g., first half of $\lambda+2\pi$ rotation shown in FIG. 15); step 4—the next half rotation (rotation index 2.5→3.0), translating the keV beamformer and/or the keV detector back to the central transaxial region can coincide with a second half of the third MeV scan rotation (e.g., second half of $\lambda+2\pi$ rotation shown in FIG. 15). These four steps can be repeated as a cycle. In this manner, complete axial and transaxial coverage can be achieved from dual energy sources 1520, 1530 during an overlapping time period (e.g., during three full rotations). As discussed above, the timing of the keV and MeV scans of the same region can be somewhat offset due to the mounted position of the radiation sources 1520, 1530 within the ring gantry 1610.

Figure 19:
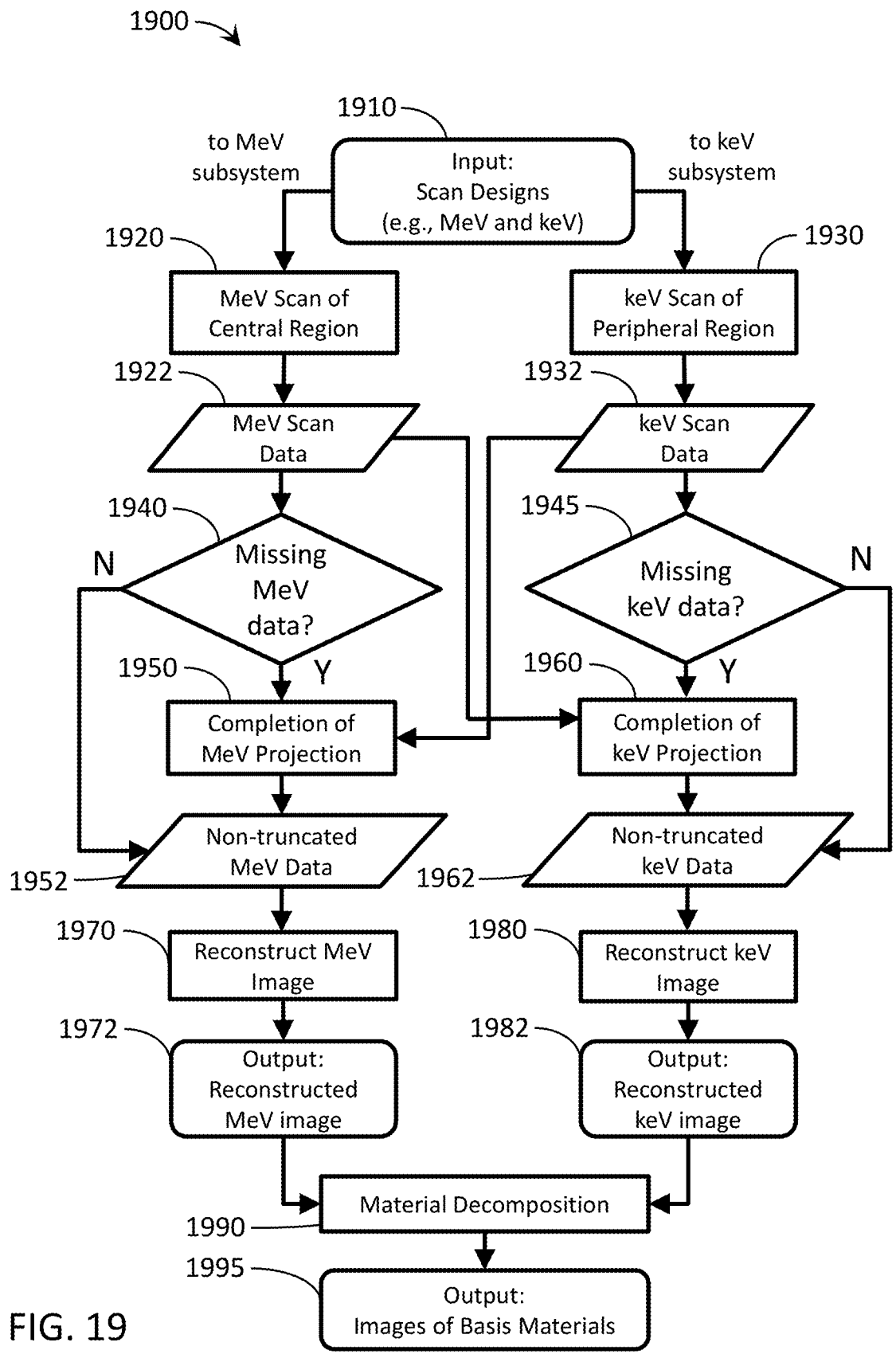
FIG. 19 is a flow chart depicting an exemplary method of combining scan data from multiple radiation modalities to approximate missing MeV and/or keV projection data based on corresponding projection data from another modality.

FIG. 19 is a flow chart depicting an exemplary method 1900 of combining scan data from multiple radiation modalities, such as those described above, to approximate missing MeV and/or keV projection data based on corresponding projection data from another modality. At step 1910, the method 1900 determines a scan configuration, including scan designs for each modality of the multimodal system. An exemplary MeV scan of a central region is executed at step 1920. An exemplary keV scan of a peripheral region is executed at step 1930. As described above, the respective scans produce MeV scan data 1922 (which may be truncated in the peripheral region) and keV scan data 1932 (which may be truncated in the central region).

At step 1940, the method 1900 determines whether the MeV scan data 1922 is missing projection data. If yes, at step 1950, the method 1900 makes use of or combines the keV scan data 1932 to complete (e.g., estimate) the MeV scan data 1922 to form a complete MeV projection or non-truncated MeV data 1952. If the MeV scan data 1922 is not missing projection data, then the MeV scan data 1922 is non-truncated MeV data 1952. Then, at step 1970, the method 1900 processes the non-truncated MeV data 1952, for example, to reconstruct a MeV image. At step 1972, the reconstructed MeV image can be output.

At step 1945, the method 1900 determines whether the keV scan data 1932 is missing projection data. If yes, at step

1960, the method 1900 makes use of or combines the MeV scan data 1922 to complete (e.g., estimate) the keV scan data 1932 to form a complete keV projection or non-truncated keV data 1962. If the keV scan data 1932 is not missing projection data, then the keV scan data 1932 is non-truncated keV data 1962. Then, at step 1980, the method 1900 processes the non-truncated keV data 1962, for example, to reconstruct a keV image. At step 1982, the reconstructed keV image can be output. Data estimation during method steps 1950 and/or 1960 may involve registration, rebinning, mapping, and/or other processes as described above.

The method 1900 may also include step 1990, which makes use of a material decompensation engine to decompose the reconstructed images into basis materials. In one embodiment, the output image(s) is used for material decomposition within an overlapped region of the keV radiation source and the MeV radiation source transaxial FOVs, resulting in basis material images. Then, at step 1995, images of basis materials can be output.

As discussed above in the context of element 950 in FIG. 9 and element 1460 in FIG. 14, the materials decomposition 1990 and output 1995 steps may include spectral analysis of the collected data via any of the methods and algorithms described above. This includes binning and/or creating a histogram according to the energy bins for spectra 62 and 64 shown in FIG. 2C and/or the histograms 66 and 68 in FIG. 2D. These techniques may be used in materials analysis and identification (e.g., by isolating photoelectric range x-ray photons to examine the atomic number (Z) dependence). They can select certain areas (e.g., soft tissue or bone) of the image for contributions from certain energies in the x-ray spectra in order to optimize presentation of the composite image (e.g., improve contrast and/or remove iodinated contrast). Spectral analysis can also differentiate between x-ray photon contributions from the photoelectric effect, Compton scattering, and/or pair production. The relative dependence on Z and energy can facilitate materials characterization and image optimization according to any of the analytical techniques described, referenced, or implied herein.

Although specific embodiments have been described, it should be appreciated that both transaxial and axial FOVs are scalable for each radiation source of a multimodal system in various combinations in other embodiments. (I.e., each modality of the multimodal system can have a scalable transaxial and/or axial FOV.) In some embodiments, the FOVs of the same and/or different modalities may be the same (e.g., transaxially and/or axially). In still further embodiments, the FOVs may be adjacent but not overlap, may have space between, may be banded such that one FOV is within the other without overlap, etc., and combinations thereof.

In some embodiments, one or more of the radiation sources may be used for sparse data, may utilize different resolutions, speeds, trajectories, frequencies, power levels, dosages, FOVs, etc. In any event, data from two or more radiation modalities can be used in combination to improve image quality, speed, dosing, workflow, treatment accuracy/precision, etc.

In various embodiments, the exemplary scan configurations (e.g., 400, 500, 600, 1000, 1500) and methods (e.g., 900, 1400, 1900) described above and those described below may be implemented using multimodal apparatus 10, including via radiation treatment environment 300.

In some embodiments, the scan configuration includes a helical scan trajectory. A helical fan-beam MeV CT (MeVCT) acquisition geometry can provide several advantages, including, for example, a wide transverse view (e.g., about 40 cm at the isocenter), capable of providing sufficient data for exact and stable image reconstruction, and decreased scatter fraction in projection images. These features can improve the quality of the reconstructed image over clinical state-of-the-art cone-beam MeVCTs. In particular, for example, a source of these advantages is the fan-collimated MeV treatment/imaging beam and the fact that the MeV source and detectors are mounted on a continuously rotating slip-ring system that is capable of imaging from all directions, as described above. In operation, the system (e.g., apparatus 10) can image continuously over more than $2\pi$ radians, moving the source and detector in a helical trajectory with respect to a patient on a translating couch without stopping to unwind cabling or resorting to atypical imaging trajectories.

In various embodiments, the multimodal apparatus 10 can include N-tuple source and detector CT systems (where N sources and N or another number of detectors are positioned such that their respective projection image data can be acquired simultaneously) with sources providing multi-energetic (e.g., low energy and high energy) projection data. Combining the use of fan-beam imaging geometries (e.g., using helical scan trajectories) with simultaneous multi-energetic keV/MeV imaging devices yields the advantages described herein. Typical existing systems are limited to cone-beam imaging geometries for either keV or MeV sources individually, which have noticeable disadvantages over fan-beam imaging geometries, as described above.

In various embodiments, high energy MeV fan-beam projections and low energy keV fan-beam or cone-beam projections can be acquired in simultaneous CT reconstructions. In some embodiments, the MeV projections can be used as a priori information to amend artifacts of the keVCT, or used in a dual-energy CT reconstruction for quantitative imaging and material separation. Furthermore, multi leaf collimator (MLC)-modulated MeV projection data is always available during treatment and may be leveraged in keVCT reconstructions concurrent with treatment delivery. Electron density images obtained from dual-energy reconstructions can be used in both online and offline dosimetry applications.

In some embodiments, the above methods can be executed simultaneously or in an interleaved manner based on a preferred workflow. For example, a multimodal scan can be performed and the resulting scan data utilized for two or more of the various features and benefits described above.

When the above apparatus and methods are used in the projection domain, it can be applied on each projection view, where each projection view is a planar image. Various embodiments can utilize different scan geometries, detector positioning (including offset detectors), and/or beamformer window shapes.

As is discussed above, aspects of the disclosed technology can be utilized in a radiotherapy device and methods that make use of multimodal radiation sources, including integrated low energy (e.g., keV) and high energy (e.g., MeV) sources for use in conjunction with or as part of IGRT. In accordance with one embodiment, the image acquisition methodology can include or otherwise makes use of a helical source trajectory (e.g., a continuous source rotation about a central axis together with longitudinal movement of a patient support through a gantry bore) or a circular scan, together with fast slip ring rotation, for example, to provide keV CT imaging on a radiation therapy delivery platform.

In some embodiments, it will be appreciated that any potential increased scan time associated with multiple beam rotations to complete a volume image can be mitigated or otherwise offset by high keV frame rates, high gantry rates, and/or sparse data reconstruction techniques. It will be further appreciated that the above-described provision of a selectively controllable collimator/beamformer allows for a system where a user can trade off or otherwise vary image acquisition time versus image quality, depending on the specific application and/or clinical need. It also will be appreciated that the radiotherapy delivery device can be controlled to provide half- or single-rotation cone beam CT scans (with potential reduced image quality due to scatter) with fast image acquisition time (e.g., for motion tracking), as well as circular or continuous helical acquisition with a narrow/slit fan beam with longer acquisition time, but increased image quality due to reduced scatter. One or more optimization processes are also applicable to all of the above embodiments to determine scan designs, determine beam positioning, determine readout range, estimate scatter, etc.

Although the disclosed technology has been shown and described with respect to a certain aspect, embodiment or embodiments, it is obvious that equivalent alterations and modifications will occur to others skilled in the art upon the reading and understanding of this specification and the annexed drawings. In particular regard to the various functions performed by the above described elements (components, assemblies, devices, members, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary aspect, embodiment or embodiments of the disclosed technology. In addition, while a particular feature of the disclosed technology may have been described above with respect to only one or more of several illustrated aspects or embodiments, such feature may be combined with one or more other features of the other embodiments, as may be desired and advantageous for any given or particular application.

While the embodiments discussed herein have been related to the systems and methods discussed above, these embodiments are intended to be exemplary and are not intended to limit the applicability of these embodiments to only those discussions set forth herein. While the present invention has been illustrated by the description of embodiments thereof, and while the embodiments have been described in some detail, it is not the intention of the applicant to restrict or in any way limit the scope of the appended claims to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general inventive concept.

The invention claimed is:

1. A radio therapy system comprising:
   a first x-ray source configured to:
      produce first x-ray photons in a first energy range suitable for imaging;
      project the first x-ray photons onto an area designated for imaging;
   a second x-ray source configured to:
      produce second x-ray photons in a second energy range higher energy than the first energy range;
      produce third x-ray photons in a third energy range higher energy than the first energy range;
      project the second x-ray photons onto the area designated for imaging;
      project the third x-ray photons onto an area designated for treatment;
   an analytical portion configured to:
      collect first data relating to the transmission of the first x-ray photons through the area designated for imaging;
      collect second data relating to the transmission of the second x-ray photons through the area designated for imaging; and
      combine the first and second data to create a composite output including at least one image, the combining based in part on a spectral analysis of at least one of the first and second data.

2. The radio therapy system of claim 1, wherein the first energy range is between 40 keV and 150 keV.

3. The radio therapy system of claim 1, wherein the second energy range is between 400 keV and 6 MeV.

4. The radio therapy system of claim 1, wherein the combining the first and second data comprises at least one of:
   sorting the second data into at least two categories based on a detected energy of the second x-ray photons; and
   identifying a material in the at least one image based on the at least two categories.

5. The radio therapy system of claim 1, wherein the area designated for imaging and the area designated for treatment overlap.

6. The radio therapy system of claim 4, wherein the identifying a material is based on analyzing a lower energy category of the at least two categories.

7. The radio therapy system of claim 6, wherein the lower energy category overlaps with an energy range relating to the photoelectric effect.

8. The radio therapy system of claim 1, wherein the combining the first and second data comprises at least one of:
   sorting the first data and second into at least two categories based on a detected energy of the first x-ray photons and a detected energy of the second x-ray photons;
   determining a relative proportion of Compton effect and photoelectric effect range photons represented by the at least two categories; and
   identifying a material in the at least one image based on the relative proportion of Compton effect and photoelectric effect range photons.

9. The radio therapy system of claim 1, wherein collecting second data relating to the transmission of the first x-ray photons comprises:
   determining an energy for each of the detected second x-ray photons; and
   building a first histogram representing the number of detected photons within segments of the second energy range.

10. The radio therapy system of claim 1, wherein collecting first data relating to the transmission of the first x-ray photons comprises:
   determining an energy for each of the detected first x-ray photons; and
   building a second histogram representing the number of detected photons within segments of the first energy range.

11. The radio therapy system of claim 1, wherein the first and second x-ray sources are positioned such that they project the first x-ray photons at an angle that differs from the projected second x-ray photons by approximately 90 degrees.

12. The radio therapy system of claim 1, where the first and second x-ray sources are coplanar.

13. The radio therapy system of claim 1, where the first and second x-ray sources are apart in the axial direction.

14. A multimodal imaging apparatus, comprising:
a rotatable gantry system positioned at least partially around a patient support;
a first radiation source coupled to the rotatable gantry system, the first radiation source configured for imaging radiation;
a first beamformer configured to adjust a shape of a first radiation beam emitted by the first radiation source;
a second radiation source coupled to the rotatable gantry system, the second radiation source configured for imaging radiation and therapeutic radiation, wherein the second radiation source comprises an energy level more than the first radiation source;
a second beamformer configured to adjust a shape of a second radiation beam emitted by the second radiation source; and
at least one radiation detector coupled to the rotatable gantry system and positioned to receive radiation from at least one of the first radiation source or the second radiation source;
wherein the apparatus is configured to:
acquire first measured projection data associated with a first region of a patient from the first radiation source and second measured projection data associated with a second region of the patient from the second radiation source during a scan; and
combine the first and second measured projection data to create a composite output including at least one image, the combining based in part on a spectral analysis of at least one of the first and second measured projection data.

15. The apparatus of claim 14, wherein the first source of radiation comprises a kilo-electron volt peak photon energy (keV) up to 150 keV and the second source of radiation comprises a mega-electron volt peak photon energy (MeV) of 1 MeV or greater.

16. The apparatus of claim 14, wherein the combining the first and second measured projection data comprises at least one of:
sorting the second measured projection data into at least two categories based on a detected energy of x-ray photons contributing to the second measured projection data; and
identifying a material in the at least one image based on the at least two categories.

17. The apparatus of claim 16, wherein the identifying a material is based in part on at least one of:
determining a relative proportion of Compton effect and photoelectric effect range photons represented by the at least two categories; and
determining a relative proportion of Compton effect and pair production range photons represented by the at least two categories.

18. A method of acquiring projection data from a multimodal imaging apparatus, comprising:
receiving first measured projection data associated with a first region of a patient from a first radiation source, the first radiation source configured for imaging radiation;
receiving second measured projection data associated with a second region of the patient from a second radiation source, the second radiation source configured for imaging radiation and therapeutic radiation, wherein the second radiation source comprises an energy level more than the first radiation source; and
combining first and second measured projection data to create a composite output including at least one image, the combining based in part on a spectral analysis of at least one of the first and second measured projection data.

* * * * *